(12) United States Patent
Gorenstein et al.

(10) Patent No.: US 8,658,614 B2
(45) Date of Patent: Feb. 25, 2014

(54) APTAMER-CONTAINING COMPOSITIONS AND METHODS FOR TARGETING E-SELECTIN

(75) Inventors: David G. Gorenstein, Houston, TX (US); Takemi Tanaka, Philadelphia, PA (US); Anoma Somasunderam, Galveston, TX (US); Aman Mann, Houston, TX (US)

(73) Assignee: The University of Texas Health Science Center, Houston, TX (US)

( * ) Notice: Subject to any disclaimer, the term of this patent is extended or adjusted under 35 U.S.C. 154(b) by 134 days.

(21) Appl. No.: 13/209,866

(22) Filed: Aug. 15, 2011

(65) Prior Publication Data

US 2012/0039810 A1    Feb. 16, 2012

Related U.S. Application Data

(60) Provisional application No. 61/373,456, filed on Aug. 13, 2010, provisional application No. 61/373,459, filed on Aug. 13, 2010, provisional application No. 61/373,461, filed on Aug. 13, 2010.

(51) Int. Cl.
*A61K 48/00* (2006.01)
*C07H 21/02* (2006.01)
*C07H 21/04* (2006.01)

(52) U.S. Cl.
USPC ..... 514/44 A; 536/23.1; 536/24.3; 536/24.33; 536/24.5

(58) Field of Classification Search
USPC .......................................... 536/24.5; 514/44
See application file for complete search history.

(56) References Cited

U.S. PATENT DOCUMENTS

| | | |
|---|---|---|
| 4,131,651 A | 12/1978 | Shah et al. |
| 4,657,760 A | 4/1987 | Kung et al. |
| 4,914,088 A | 4/1990 | Glonek et al. |
| 5,206,344 A | 4/1993 | Katre et al. |
| 5,225,212 A | 7/1993 | Martin et al. |
| 5,278,151 A | 1/1994 | Korb et al. |
| 5,294,607 A | 3/1994 | Glonek et al. |
| 5,578,586 A | 11/1996 | Glonek et al. |
| 5,612,057 A | 3/1997 | Lanza et al. |
| 5,858,399 A | 1/1999 | Lanza et al. |
| 6,423,493 B1 | 7/2002 | Gorenstein et al. |
| 6,867,289 B1 | 3/2005 | Gorenstein et al. |
| 7,179,894 B2 | 2/2007 | Gorenstein et al. |
| 7,338,762 B2 | 3/2008 | Gorenstein et al. |
| 7,576,037 B2 | 8/2009 | Engelhardt et al. |
| 7,713,517 B2 | 5/2010 | Annapragada et al. |

OTHER PUBLICATIONS

Mann et al. (PLOS One, 2010 vol. 5, Issue 9:1-11).*

* cited by examiner

*Primary Examiner* — Terra Cotta Gibbs
(74) *Attorney, Agent, or Firm* — Conley Rose, P.C.

(57) ABSTRACT

An isolated nucleic acid molecule that selectively binds to an E-selectin protein comprises a contiguous 29-30 nucleotide sequence that includes at least one monothiophosphate or a dithiophosphate modified nucleotide. Also disclosed are methods of inhibiting an E-selectin mediated interaction with a natural E-selectin ligand, and methods of targeting an imaging agent or therapeutic agent to a target tissue bearing E-selectin.

20 Claims, 21 Drawing Sheets

Figure 1

| SEQ ID NO: | SEQUENCE IDENTIFIER | SEQUENCE |
|---|---|---|
| SEQ ID NO: 37 | 10-1 | ATCCACTCTCCCGTTCACTTCTCCTCAC |
| SEQ ID NO: 38 | 10-14 | TCTCCCTCCTTCTCCTCTCCTCGCTTCACC |
| SEQ ID NO: 39 | 10-4 | TCCCCGTCCTTTCTCTTCCCTTCCCCTCGG |
| SEQ ID NO: 40 | 10-26 | TTCCCGCACTCCTCCATCCTCCCTTCACAC |
| SEQ ID NO: 41 | 10-9 | CCCTCCCCTATACCACTGTCAACTTCCACT |
| SEQ ID NO: 42 | 10-2 | ACCCTACTACACCATCTCACCTCAACCCTC |
| SEQ ID NO: 43 | 10-6 | CCTCCACTCCTCCCTTCACTCTACCCACCC |
| SEQ ID NO: 44 | 10-20 | GCCTTCTCCTGGACTCCACTTCACTCCGTG |
| SEQ ID NO: 45 | 10-13 | CCTGCACCTCCACCCTACACACTAAACGCG |
| SEQ ID NO: 46 | 10-10 | TCCTCTCCTCTCGTGTATCCACTCCACACA |
| SEQ ID NO: 47 | 10-7 | GCCCTACACTCACCCTCACCCAGACACACC |
| SEQ ID NO: 48 | 10-31 | GCCCACACCTCCAACACACGCGCCTCCGC |
| SEQ ID NO: 49 | 10-30 | TCCTTCCCAGTTCCATCTTATCCTCCTCGG |

Figure 3

| SEQ ID NO: | Sequence Motif | Sequence identifier |
|---|---|---|
| SEQ ID NO: 18 | ACT(T/C)C(T/A)C(T/C)TCAC | (1,20) |
| SEQ ID NO: 50 | TCCTC | (1,4,14,6,25,26,10,20) |
| SEQ ID NO: 51 | TCCCGTT | (1,4,6,26) |
| SEQ ID NO: 52 | TCCCC(T/G) | (4,9,25) |
| SEQ ID NO: 53 | ACCC (T/A)( A/C) | (2,6,13,7) |
| SEQ ID NO: 54 | ACT( A/T/C) C | (1,26,6,20,20,13,10) |
| SEQ ID NO: 55 | TCCC(G/T) | (1,14,4,26,6,30) |
| SEQ ID NO: 56 | ATCC | (1,26,25,10) |
| SEQ ID NO: 57 | CCCGT(T/C) | (1,4,25) |
| SEQ ID NO: 58 | CTTC(T/A) | (1,14,26,6,20,30) |

Figure 4

| SEQ ID NO: | Sequence Identifier | ΔG (Kcal/mol) | Relative Binding | Relative Specificity |
|---|---|---|---|---|
| SEQ ID NO: 1 | TA-1 | 10.72 | +++ | +++ |
| SEQ ID NO: 20 | TA-20 | 7.98 | ++ | + |
| SEQ ID NO: 31 | TA-31 | 8.64 | + | + |
| SEQ ID NO: 14 | TA-14 | 6.31 | ~ | ~ |
| SEQ ID NO: 4 | TA-4 | 7.25 | ~ | ~ |
| SEQ ID NO: 26 | TA-26 | 5.86 | ~ | ~ |
| SEQ ID NO: 9 | TA-9 | 3.62 | ~ | ~ |
| SEQ ID NO: 25 | TA-25 | 6.25 | ~ | ~ |
| SEQ ID NO: 2 | TA-2 | 3.78 | ~ | ~ |
| SEQ ID NO: 6 | TA-6 | 6.24 | ~ | ~ |
| SEQ ID NO: 13 | TA-13 | 4.68 | ~ | ~ |
| SEQ ID NO: 10 | TA-10 | 6.09 | ~ | ~ |
| SEQ ID NO: 7 | TA-7 | 5.49 | ~ | ~ |
| SEQ ID NO: 30 | TA-30 | 6.07 | ~ | ~ |

Figure 5

SEQ ID NO:1

(a-d = SEQ ID NO: 20)

(a-d = SEQ ID NO: 31)

A

5'-CGCTCGGATCGATAAGCTTCG-ATCCCACTCTCCCGTTCACTTCTCCTCAC-GTCACGGATCCTCTAGAGCACTG-3'.

B (A and B = SEQ ID NO: 1)

SEQUENCE LISTING

```
<160> NUMBER OF SEQ ID NOS: 60

<210> SEQ ID NO 1
<211> LENGTH: 73
<212> TYPE: DNA
<213> ORGANISM: Artificial sequence
<220> FEATURE:
<223> OTHER INFORMATION: Binds E-selectin

<400> SEQUENCE: 1
cgctcggatc gataagcttc gatcccactc tcccgttcac ttctcctcac gtcacggatc      60
ctctagagca ctg                                                         73

<210> SEQ ID NO 2
<211> LENGTH: 73
<212> TYPE: DNA
<213> ORGANISM: Artificial sequence
<220> FEATURE:
<223> OTHER INFORMATION: Binds E-selectin

<400> SEQUENCE: 2
cgctcggatc gataagcttc gaccctacta caccatctca cctcaaccct cgtcacggat      60
ccttagagca ctg                                                         73

<210> SEQ ID NO 3
<211> LENGTH: 74
<212> TYPE: DNA
<213> ORGANISM: Artificial sequence
<220> FEATURE:
<223> OTHER INFORMATION: Binds E-selectin

<400> SEQUENCE: 3
cgctcggatc gataagcttc ggtcgccccc tacactccac atcaagccgc cgtcacggat      60
cctctagagc actg                                                        74

<210> SEQ ID NO 4
<211> LENGTH: 73
<212> TYPE: DNA
<213> ORGANISM: Artificial sequence
<220> FEATURE:
<223> OTHER INFORMATION: Binds E-selectin
```

-continued

```
<400> SEQUENCE: 4
cgctcggatc gataagcttc gtccccgtcc tttctcttcc cttcccctcg ggcacgggtc    60
ctctagagca ctg                                                      73

<210> SEQ ID NO 5
<211> LENGTH: 74
<212> TYPE: DNA
<213> ORGANISM: Artificial sequence
<220> FEATURE:
<223> OTHER INFORMATION: Binds E-selectin

<400> SEQUENCE: 5
cgctcggatc gataagcttc gtcctccccc cctcttaccc tctcctgtac cgtcacggat    60
cctctagagc actg                                                     74

<210> SEQ ID NO 6
<211> LENGTH: 74
<212> TYPE: DNA
<213> ORGANISM: Artificial sequence
<220> FEATURE:
<223> OTHER INFORMATION: Binds E-selectin

<400> SEQUENCE: 6
cgctcggatc gataagcttc gcctccactc ctcccttcac tctacccacc cgtcacggat    60
cctctagagc actg                                                     74

<210> SEQ ID NO 7
<211> LENGTH: 74
<212> TYPE: DNA
<213> ORGANISM: Artificial sequence
<220> FEATURE:
<223> OTHER INFORMATION: Binds E-selectin

<400> SEQUENCE: 7
cgctcggatc gataagcttc ggccctacac tcaccctcac ccagacacac cgtcacggat    60
cctctagagc actg                                                     74

<210> SEQ ID NO 8
<211> LENGTH: 74
<212> TYPE: DNA
<213> ORGANISM: Artificial sequence
<220> FEATURE:
<223> OTHER INFORMATION: Binds E-selectin

<400> SEQUENCE: 8
cgctcggatc gataagcttc gcccttccac tctaccttcg cctctgcaca cgtcacggat    60
cctctagagc actg                                                     74

<210> SEQ ID NO 9
<211> LENGTH: 73
<212> TYPE: DNA
<213> ORGANISM: Artificial sequence
<220> FEATURE:
<223> OTHER INFORMATION: Binds E-selectin

<400> SEQUENCE: 9
cgctcggatc gataagcttc gccctcccct ataccactgt caacttccac tgtcacggat    60
cctctagagc act                                                      73

<210> SEQ ID NO 10
<211> LENGTH: 74
```

```
<212> TYPE: DNA
<213> ORGANISM: Artificial sequence
<220> FEATURE:
<223> OTHER INFORMATION: Binds E-selectin

<400> SEQUENCE: 10
cgctcggatc gataagcttc gtcctctcct ctcgtgtatc cactccacac agtcacggat      60
cctctagagc actg                                                       74

<210> SEQ ID NO 11
<211> LENGTH: 73
<212> TYPE: DNA
<213> ORGANISM: Artificial sequence
<220> FEATURE:
<223> OTHER INFORMATION: Binds E-selectin

<400> SEQUENCE: 11
cgctcggatc gataagcttc ggggctcttc ctcctcaatt cacctcacac agtcacggat      60
cctctagagc act                                                        73

<210> SEQ ID NO 12
<211> LENGTH: 74
<212> TYPE: DNA
<213> ORGANISM: Artificial sequence
<220> FEATURE:
<223> OTHER INFORMATION: Binds E-selectin

<400> SEQUENCE: 12
cgctcggatc gataagcttc gtcctttcct tctcttctcc ttccatctaa cgtcacggat      60
cctctagagc actg                                                       74

<210> SEQ ID NO 13
<211> LENGTH: 74
<212> TYPE: DNA
<213> ORGANISM: Artificial sequence
<220> FEATURE:
<223> OTHER INFORMATION: Binds E-selectin

<400> SEQUENCE: 13
cgctcggatc gataagcttc gcctgcacct ccaccctaca cactaaacgc ggtcacggat      60
cctctagagc actg                                                       74

<210> SEQ ID NO 14
<211> LENGTH: 74
<212> TYPE: DNA
<213> ORGANISM: Artificial sequence
<220> FEATURE:
<223> OTHER INFORMATION: Binds E-selectin

<400> SEQUENCE: 14
cgctcggatc gataagcttc gtctccctcc ttctcctctc ctcgcttcac cgtcacggat      60
cctctagagc actg                                                       74

<210> SEQ ID NO 15
<211> LENGTH: 73
<212> TYPE: DNA
<213> ORGANISM: Artificial sequence
<220> FEATURE:
<223> OTHER INFORMATION: Binds E-selectin

<400> SEQUENCE: 15
cgctcggatc gataagcttc gttctcttcc cctctccacg ccacccgaac gtcacggatc      60
ctctagagca ctg                                                        73
```

<210> SEQ ID NO 16
<211> LENGTH: 74
<212> TYPE: DNA
<213> ORGANISM: Artificial sequence
<220> FEATURE:
<223> OTHER INFORMATION: Binds E-selectin

<400> SEQUENCE: 16
cgctcggatc gataagcttc gtctcctcca tttcccttca attcccacct cgtcacggat    60
cctctagagc actg                                                      74

<210> SEQ ID NO 17
<211> LENGTH: 74
<212> TYPE: DNA
<213> ORGANISM: Artificial sequence
<220> FEATURE:
<223> OTHER INFORMATION: Binds E-selectin

<400> SEQUENCE: 17
cgctcggatc gataagcttc gcccttcacc ccatctcccc ttcaccttca cgtcacggat    60
cctctagagc actg                                                      74

<210> SEQ ID NO 18
<211> LENGTH: 12
<212> TYPE: DNA
<213> ORGANISM: Artificial sequence
<220> FEATURE:
<223> OTHER INFORMATION: E-selectin binding aptamer sequence motif

<400> SEQUENCE: 18
actycwcytc ac                                                        12

<210> SEQ ID NO 19
<211> LENGTH: 74
<212> TYPE: DNA
<213> ORGANISM: Artificial sequence
<220> FEATURE:
<223> OTHER INFORMATION: Binds E-selectin

<400> SEQUENCE: 19
cgctcggatc gataagcttc gcccctctcc acttctactc tataccctct cgtcacggat    60
cctctagagc actg                                                      74

<210> SEQ ID NO 20
<211> LENGTH: 74
<212> TYPE: DNA
<213> ORGANISM: Artificial sequence
<220> FEATURE:
<223> OTHER INFORMATION: Binds E-selectin

<400> SEQUENCE: 20
cgctcggatc gataagcttc ggccttctcc tggactccac ttcactccgt ggtcacggat    60
cctctagagc actg                                                      74

<210> SEQ ID NO 21
<211> LENGTH: 74
<212> TYPE: DNA
<213> ORGANISM: Artificial sequence
<220> FEATURE:
<223> OTHER INFORMATION: Binds E-selectin

<400> SEQUENCE: 21
cgctcggatc gataagcttc gcctcccact tccacatcca cccactcgaa cgtcacggat    60

```
cctctagagc actg                                                        74

<210> SEQ ID NO 22
<211> LENGTH: 74
<212> TYPE: DNA
<213> ORGANISM: Artificial sequence
<220> FEATURE:
<223> OTHER INFORMATION: Binds E-selectin

<400> SEQUENCE: 22
cgctcggatc gataagcttc gacctcccct ccttcactcc atctccaccc cgtcacggat       60
cctctagagc actg                                                        74

<210> SEQ ID NO 23
<211> LENGTH: 74
<212> TYPE: DNA
<213> ORGANISM: Artificial sequence
<220> FEATURE:
<223> OTHER INFORMATION: Binds E-selectin

<400> SEQUENCE: 23
cgctcggatc gataagcttc gtctccccct tccatttcca ctttcccct cgtcacggat        60 cctctagagc actg                                                        74

<210> SEQ ID NO 24
<211> LENGTH: 74
<212> TYPE: DNA
<213> ORGANISM: Artificial sequence
<220> FEATURE:
<223> OTHER INFORMATION: Binds E-selectin

<400> SEQUENCE: 24
cgctcggatc gataagcttc gtccttctct ccatcaccct cccaccttcc ggtcacggat       60
cctctagagc actg                                                        74

<210> SEQ ID NO 25
<211> LENGTH: 74
<212> TYPE: DNA
<213> ORGANISM: Artificial sequence
<220> FEATURE:
<223> OTHER INFORMATION: Binds E-selectin

<400> SEQUENCE: 25
cgctcggatc gataagcttc gccctcccct cctccatcca ttccccgtca cgtcacggat      60
cctctagagc actg                                                        74

<210> SEQ ID NO 26
<211> LENGTH: 74
<212> TYPE: DNA
<213> ORGANISM: Artificial sequence
<220> FEATURE:
<223> OTHER INFORMATION: Binds E-selectin

<400> SEQUENCE: 26
cgctcggatc gataagcttc gttcccgcac tcctccatcc tcccttcaca cgtcacggat      60
cctctagagc actg                                                        74

<210> SEQ ID NO 27
<211> LENGTH: 74
<212> TYPE: DNA
<213> ORGANISM: Artificial sequence
<220> FEATURE:
<223> OTHER INFORMATION: Binds E-selectin
```

```
<400> SEQUENCE: 27
cgctcggatc gataagcttc gcccttcccc ttcttctcct ctaccgcaca cgtcacggat    60
cctctagagc actg                                                     74

<210> SEQ ID NO 28
<211> LENGTH: 74
<212> TYPE: DNA
<213> ORGANISM: Artificial sequence
<220> FEATURE:
<223> OTHER INFORMATION: Binds E-selectin

<400> SEQUENCE: 28
cgctcggatc gataagcttc gtcccttta c cccgcctcta catcccgcct cgtcacggat    60
cctctagagc actg                                                     74

<210> SEQ ID NO 29
<211> LENGTH: 67
<212> TYPE: DNA
<213> ORGANISM: Artificial sequence
<220> FEATURE:
<223> OTHER INFORMATION: Binds E-selectin

<400> SEQUENCE: 29
cgctcggatc gataagcttc gtccgtctat accccacact cgccgtcacg gatcctctag    60
agcactg                                                             67

<210> SEQ ID NO 30
<211> LENGTH: 74
<212> TYPE: DNA
<213> ORGANISM: Artificial sequence
<220> FEATURE:
<223> OTHER INFORMATION: Binds E-selectin

<400> SEQUENCE: 30
cgctcggatc gataagcttc gtccttccca gttccatctt atcctcctcg ggtcacggat    60
cctctagagc actg                                                     74

<210> SEQ ID NO 31
<211> LENGTH: 74
<212> TYPE: DNA
<213> ORGANISM: Artificial sequence
<220> FEATURE:
<223> OTHER INFORMATION: Binds E-selectin

<400> SEQUENCE: 31
cgctcggatc gataagcttc ggccccacac ctccaacaca cgcgcctccg cgtcacggat    60
cctctagagc actg                                                     74

<210> SEQ ID NO 32
<211> LENGTH: 73
<212> TYPE: DNA
<213> ORGANISM: Artificial sequence
<220> FEATURE:
<223> OTHER INFORMATION: Binds E-selectin

<400> SEQUENCE: 32
cgttgggatg gataagtttg gaccctcctc gttcccttt t ctcctttcac gtcacggatc    60
ctctagagca ctg                                                      73

<210> SEQ ID NO 33
<211> LENGTH: 74
```

```
<212> TYPE: DNA
<213> ORGANISM: Artificial sequence
<220> FEATURE:
<223> OTHER INFORMATION: Binds E-selectin

<400> SEQUENCE: 33
cgctcggatc gataagcttc gacctcctac cccatcaatc tccacaccta ggtcacggat      60
cctctagagc actg                                                         74

<210> SEQ ID NO 34
<211> LENGTH: 74
<212> TYPE: DNA
<213> ORGANISM: Artificial sequence
<220> FEATURE:
<223> OTHER INFORMATION: Binds E-selectin

<400> SEQUENCE: 34
cgctcggatc gataagcttc gtcccttcca ccatccacaa ctctacccaa cgtcacggat      60
cctctagagc actg                                                         74

<210> SEQ ID NO 35
<211> LENGTH: 75
<212> TYPE: DNA
<213> ORGANISM: Artificial sequence
<220> FEATURE:
<223> OTHER INFORMATION: Binds E-selectin

<400> SEQUENCE: 35
cgctcggatc gataagcttc gtcctttcat tccttacct gctagactcc acgtcacgga       60
tcctctagag cactg                                                        75

<210> SEQ ID NO 36
<211> LENGTH: 74
<212> TYPE: DNA
<213> ORGANISM: Artificial sequence
<220> FEATURE:
<223> OTHER INFORMATION: Binds E-selectin

<400> SEQUENCE: 36
cgctcggatc gataagcttc gccccccgac cacgctcatg ccgtctaccc cgtcacggat      60
cctctagagc actg                                                         74

<210> SEQ ID NO 37
<211> LENGTH: 29
<212> TYPE: DNA
<213> ORGANISM: Artificial sequence
<220> FEATURE:
<223> OTHER INFORMATION: Nucleotides 22-50 of SEQ ID NO.: 1

<400> SEQUENCE: 37
atcccactct cccgttcact tctcctcac                                         29

<210> SEQ ID NO 38
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 14

<400> SEQUENCE: 38
tctccctcct tctcctctcc tcgcttcacc                                        30

<210> SEQ ID NO 39
<211> LENGTH: 30
```

```
<212> TYPE: DNA
<213> ORGANISM: Artificial sequence
<220> FEATURE:
<223> OTHER INFORMATION: Nucleotides 22-51 of SEQ ID NO.: 4

<400> SEQUENCE: 39
tccccgtcct ttctcttccc ttccctcgg                                            30

<210> SEQ ID NO 40
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 26

<400> SEQUENCE: 40
ttcccgcact cctccatcct cccttcacac                                           30

<210> SEQ ID NO 41
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 9

<400> SEQUENCE: 41 ccctcccta taccactgtc aacttccact                                            30

<210> SEQ ID NO 42
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 2

<400> SEQUENCE: 42
accctactac accatctcac ctcaaccctc                                           30

<210> SEQ ID NO 43
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 6

<400> SEQUENCE: 43
cctccactcc tcccttcact ctacccaccc                                           30

<210> SEQ ID NO 44
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 20

<400> SEQUENCE: 44
gccttctcct ggactccact tcactccgtg                                           30

<210> SEQ ID NO 45
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 13

<400> SEQUENCE: 45
cctgcacctc caccctacac actaaacgcg                                           30
```

-continued

```
<210> SEQ ID NO 46
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 10

<400> SEQUENCE: 46
tcctctcctc tcgtgtatcc actccacaca                                    30

<210> SEQ ID NO 47
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 7

<400> SEQUENCE: 47
gccctacact caccctcacc cagacacacc                                    30

<210> SEQ ID NO 48
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 31

<400> SEQUENCE: 48
gccccacacc tccaacacac gcgcctccgc                                    30

<210> SEQ ID NO 49
<211> LENGTH: 30
<212> TYPE: DNA
<213> ORGANISM: Artificial sequence
<220> FEATURE:
<223> OTHER INFORMATION: Nucleotides 22-51 of SEQ ID NO.: 30

<400> SEQUENCE: 49
tccttcccag ttccatctta tcctcctcgg                                    30

<210> SEQ ID NO 50
<211> LENGTH: 5
<212> TYPE: DNA
<213> ORGANISM: Artificial sequence
<220> FEATURE:
<223> OTHER INFORMATION: E-selectin binding aptamer sequence motif;
      nucleotides 13-17 of SEQ ID NO.: 38

<400> SEQUENCE: 50 tcctc                                                               5

<210> SEQ ID NO 51
<211> LENGTH: 7
<212> TYPE: DNA
<213> ORGANISM: Artificial sequence
<220> FEATURE:
<223> OTHER INFORMATION: E-selectin binding aptamer sequence motif;
      nucleotides 10-16 of SEQ ID NO.: 37

<400> SEQUENCE: 51 tcccgtt                                                             7

<210> SEQ ID NO 52
<211> LENGTH: 6
<212> TYPE: DNA
<213> ORGANISM: Artificial sequence
```

```
<220> FEATURE:
<223> OTHER INFORMATION: E-selectin aptamer binding motif; nucleotides
      1-6 or 22-27 of SEQ ID NO.: 39

<400> SEQUENCE: 52 tcccck                                                                    6

<210> SEQ ID NO 53
<211> LENGTH: 6
<212> TYPE: DNA
<213> ORGANISM: Artificial sequence
<220> FEATURE:
<223> OTHER INFORMATION: E-selectin aptamer binding motif; nucleotides
      1-6 or 25-30 of SEQ ID NO.: 42

<400> SEQUENCE: 53 acccwm                                                                    6

<210> SEQ ID NO 54
<211> LENGTH: 5
<212> TYPE: DNA
<213> ORGANISM: Artificial sequence
<220> FEATURE:
<223> OTHER INFORMATION: E-selectin aptamer binding motif; nucleotides
      18-22 of SEQ ID NO.: 37 or nucleotides 8-12 of SEQ ID NO.: 40 or
      nucleotides 6-10 of SEQ ID NO.: 42

<400> SEQUENCE: 54 acthc                                                                     5

<210> SEQ ID NO 55
<211> LENGTH: 5
<212> TYPE: DNA
<213> ORGANISM: Artificial sequence
<220> FEATURE:
<223> OTHER INFORMATION: E-selectin aptamer binding motif; nucleotides
      10-14 of SEQ ID NO.: 37 or nucleotides 3-7 of SEQ ID NO.: 38

<400> SEQUENCE: 55 tccck                                                                     5

<210> SEQ ID NO 56
<211> LENGTH: 4
<212> TYPE: DNA
<213> ORGANISM: Artificial sequence
<220> FEATURE:
<223> OTHER INFORMATION: E-selectin aptamer binding motif; nucleotides
      1-4 of SEQ ID NO.: 37

<400> SEQUENCE: 56 atcc                                                                      4

<210> SEQ ID NO 57
<211> LENGTH: 6
<212> TYPE: DNA
<213> ORGANISM: Artificial sequence
<220> FEATURE:
<223> OTHER INFORMATION: E-selectin aptamer binding motif; nucleotides
      11-16 of SEQ ID NO.: 37 or nucleotides 3-8 of SEQ ID NO.: 39

<400> SEQUENCE: 57 cccgty                                                                    6

<210> SEQ ID NO 58
<211> LENGTH: 5
<212> TYPE: DNA
<213> ORGANISM: Artificial sequence
<220> FEATURE:
```

```
<223> OTHER INFORMATION: E-selectin aptamer binding motif; nucleotides
      19-23 of SEQ ID NO.: 37 or nucleotides 23-27 of SEQ ID NO.: 40

<400> SEQUENCE: 58 cttcw                                                                      5

<210> SEQ ID NO 59
<211> LENGTH: 23
<212> TYPE: DNA
<213> ORGANISM: Artificial sequence
<220> FEATURE:
<223> OTHER INFORMATION: PCR forward primer sequence for E-selectin
      binding aptamer

<400> SEQUENCE: 59
cagtgctcta gaggatccgt gac                                                 23

<210> SEQ ID NO 60
<211> LENGTH: 21
<212> TYPE: DNA
<213> ORGANISM: Artificial sequence
<220> FEATURE:
<223> OTHER INFORMATION: PCR reverse primer sequence for E-selectin
      binding aptamer

<400> SEQUENCE: 60
cgctcggatc gataagcttc g                                                   21
```

APTAMER-CONTAINING COMPOSITIONS AND METHODS FOR TARGETING E-SELECTIN

CROSS-REFERENCE TO RELATED APPLICATION

This application claims the benefit under 35 U.S.C. §119 (e) of U.S. Provisional Patent Application No. 61/373,456 filed Aug. 13, 2010; U.S. Provisional Patent Application No. 61/373,459 filed Aug. 13, 2010; U.S. Provisional Patent Application No. 61/373,461 filed Aug. 13, 2010, the disclosures of which are hereby incorporated herein by reference.

STATEMENT REGARDING FEDERALLY SPONSORED RESEARCH OR DEVELOPMENT

This invention was made with U.S. Government support under Grant Nos. R01CA128797, CA110793, CA109298, U01 AI054827, N01 HV28184 and HHSN272200800048C, from the National Institute of Health and Grant Nos. W81XWH-07-2-0101, W81XWH-09-1-0212 from the U.S. Department of Defense. The government has certain rights in the invention.

FIELD OF TECHNOLOGY

The present disclosure generally relates to thiophosphate oligodeoxynucleotide aptamers and aptamer conjugates that selectively bind E-selectin protein, and to their use in diagnosis, prevention and treatment of E-selectin associated disorders.

BACKGROUND

The selectins, E-, L-, and P-selectin, constitute a family of calcium dependent cell surface glycoproteins that play critical role in inflammation mainly through recognition of specific carbohydrate ligands, sialyl Lewis X ($sLe^X$) and sialyl Lewis A ($sLe^A$) (Berg E L, et. al., 1991. A carbohydrate domain common to both sialyl $Le^A$ and sialyl $Le^X$ is recognized by the endothelial cell leukocyte adhesion molecule ELAM-1. *J. Biol. Chem.* 266, 14869-14872). E-selectin is a calcium dependent cell surface glycoprotein, predominantly expressed in the vascular endothelium and bone-skin microvascular lining, and plays a crucial role in inflammation.

Among the selectin family, E-selectin (CD62E, ELAM-1 or LECAM-2) has been highlighted as a therapeutic target based on its unique role in inflammation. Unlike L-selectin, E-selectin is not constitutively expressed in endothelial cells, but transcriptionally induced by NF-κB and AP-1 in response to inflammatory cytokines such as IL-1 and TNF-α (Bevilacqua M. P. et al. (1987) Identification of an inducible endothelial-leukocyte adhesion molecule. *Proc Natl Acad Sci USA* vol. 84 (24) pp. 9238-42). Consequently, elevated E-selectin expression has been reported in many types of inflammatory diseases including diabetes, arthrosclerosis, rheumatoid arthritis, and cancer (Bevilacqua M. P. (1993) Endothelial-leukocytes adhesion molecules. *Ann Rev Immunol.* 11:767-804). In addition, E-selectin and their ligands have also been reported to play key role in the diapedesis of metastatic carcinoma cells including prostate (Dimitroff, C. J. et al., (2005) Identification of leukocyte E-selectin ligands, P-selectin glycoprotein ligand-1 and E-selectin ligand-1, on human metastatic prostate tumor cells. *Cancer Res.* 65, 5750-5760), breast (Jeschke, U. et al. (2005) Expression of sialyl Lewisx, sialyl Lewisa, E-cadherin and cathepsin-D in human breast cancer: immunohistochemical analysis in mammary carcinoma in situ, invasive carcinoma and their lymph node metastasis. *Anticancer Res.* 25, 1615-1622), colon (Matsumoto, S. et al. (2002) Cimetidine increases survival of colorectal cancer patients with high levels of sialyl Lewis X and sialyl Lewis A epitope expression on tumor cells. *Brit. J. Cancer* 86, 161-167), and lung (Inata, J. et al. (2007) Circulating KL-6/MUC1 mucin carrying sialyl Lewisa oligosaccharide is an independent prognostic factor in patients with lung adenocarcinoma. *Int. J. Cancer* 120, 2643-2649). More recently, E-selectin was found to be expressed constitutively in an endothelial cell lineage of the bone marrow (Sackstein, R. (2004) The bone marrow is akin to skin: HCELL and the biology of hematopoietic stem cell homing. *J. Invest. Dermatol.* 122, 1061-1069) and assist in the homing of prostate cancer cells and leukemic cells to the bone marrow through the binding of $sLe^X$ (Krause, D. S. et al., (2006) Requirement for CD44 in homing and engraftment of BCR-ABL-expressing leukemic stem cells. *Nature Med.* 12, 1175-1180; 10. Dimitroff et al. (2004) Rolling of human bone-metastatic prostate tumor cells on human bone marrow endothelium under shear flow is mediated by E-selectin. *Cancer Res.* 64 (15), 5261-9). Targeting E-selectin potentially offers a way to control the pathological infiltration of leukocytes and/or metastatic cancer cells and to target therapies and imaging agents to the inflamed vasculature of these tissues/cancers. To date, many efforts have been made to develop a high affinity ligand to antagonize E-selectin-mediated rolling and/or adhesion and diapedesis. E-selectin ligands such as monoclonal antibody (Bevilacqua M. P. et al. (1987) Identification of an inducible endothelial-leukocyte adhesion molecule. *Proc Natl Acad Sci USA* vol. 84 (24), 9238-42), peptide ligand (Martens et al. (1995). Peptides which bind to E-selectin and block neutrophil adhesion. *J Biol Chem* 270 (36), 21129-36), and carbohydrate ligand (Ernst and Magnani. (2009) from carbohydrate leads to glycomimetic drugs. *Nature Reviews Drug Discovery* 8 (8), 661-77) have shown selective binding to the inflamed vasculature in both experimental animal models and clinical trials (P. T. Chapman, et al., 1996. Use of a radiolabeled monoclonal antibody against E-selectin for imaging of endothelial activation in rheumatoid arthritis, *Arthritis Rheum.* 39 (8), 1371-1375; K. R. Zinn, et al., 1999. Specific targeting of activated endothelium in rat adjuvant arthritis with a 99 mTc-radiolabeled E-selectin-binding peptide, *Arthritis Rheum.* 42 (4), 641-649), however their medical application remains a challenge due to a lack of serum stability, low affinity, low specificity, and immunogenicity (Martens C L, et al., 1995. Peptides which bind to E-selectin and block neutrophil adhesion. *J Biol Chem* 270: 21129-21136; Bhushan M, et al., 2002. Anti-E-selectin is ineffective in the treatment of psoriasis: a randomized trial. *Br J Dermatol* 146: 824-831; Magnani J L, Ernst B, 2009. Glycomimetic drugs—a new source of therapeutic opportunities. *Discov Med* 8: 247-252). Therefore, identification of a novel ligand that blocks E-selectin mediated rolling and/or adhesion and diapedesis, with enhanced clinical compatibility is desirable. Furthermore, an antagonistic E-selectin ligand that blocks the initial adhesion of these cells to the endothelial surface is an attractive therapeutic approach against inflammation and cancer metastasis.

Aptamers are oligonucleic acid or peptide molecules that bind to a specific target molecule. Thiophosphate oligonucleotide aptamers (thioaptamers; TA) are a new class of ligands that structurally differ from RNA and DNA and can bind proteins at high (nM) affinity (for review see: Yang and Gorenstein, Progress in Thioaptamer Development *Current*

*Drug Targets,* 2004, 5, 705-715; Marshall and Caruthers, 1993. Phosphorodithioate DNA as a potential therapeutic drug. *Science.* March 12; 259(5101):1564-70). TAs offer significant advantages over conventional peptide ligand or antibody due to their unique chemical and biological properties: a) high affinity to protein (see for review Marshall and Caruthers, 1993, ibid); b) nuclease resistance (Kusser, 2000. Chemically modified nucleic acid aptamers for in vitro selections: evolving evolution. *Reviews in Molecular Biotechnology,* 74 (1), 27-38); c) easy synthesis and chemical modification (for a review see Micklefield J., 2001. Backbone modification of nucleic acids: synthesis, structure and therapeutic applications. *Curr Med Chem.* 8(10), 1157-79); d) lack of immunogenicity (Monteith, D. K., et al., 1997. Immune simulation: A class effect of phosphorothioate oligodeoxynucleotides in rodents, *Anti-cancer Drug Design,* 12, 421-432). Recently methods have been developed for combinatorial selection of TA libraries consisting of $10^{14}$ random sequences (King, D J, et al., 1998. Novel Combinatorial Selection of Phosphorothioate Oligonucleotide Aptamers, Biochemistry, 37 (47), pp 16489-16493; King, D J, et al., 2002. Combinatorial Selection and Binding of Phosphorothioate Aptamers Targeting Human NF-κB RelA(p65) and p50, *Biochemistry* 41, 9696-9706; Somasunderam, A, et al., 2005. Combinatorial Selection, Inhibition and Antiviral Activity of DNA Thioaptamers Targeting the RNase H Domain of HIV-1 Reverse Transcriptase. *Biochemistry,* 44(30), 10388-10395) and have identified TAs that bind to a wide variety of target proteins (King et al. 2002, ibid; Somasunderam, et al. 2005, ibid; Kang, J, et al., 2008. Combinatorial selection of a single stranded DNA thioaptamer targeting TGF-beta-1 protein. *Bioorg. Med. Chem. Lett.* 18(6): 1835-1839).

The majority of screenings of aptamers libraries utilize either full-length or fragments of recombinant proteins (Joyce G F, 1994. In vitro evolution of nucleic acids. *Curr Opin Struct Biol.* 4:331-6. Gold L, 1995. Oligonucleotides as research, diagnostic, and therapeutic agents. J Biol Chem. June 9; 270(23):13581-4; Osborne S E, et al., 1997. Aptamers as therapeutic and diagnostic reagents: problems and prospects. *Curr Opin Chem Biol.* June; 1(1):5-9; Ellington, A D., Szostak, J. W., 1992. Selection in vitro of single-stranded DNA molecules that fold into specific ligand-binding structures, *Nature,* 355 (6363): 850). However, the structural differences that result from the lack of post-translational modifications and possible misfolding of these recombinant proteins may preclude the identification of aptamers that would maintain their binding capabilities in a physiological environment.

E-selectin ligands including monoclonal antibodies, peptide, and carbohydrate ligands have shown selective binding to the inflamed vasculature in both experimental animal models and human clinical trials. However, medical applications of these ligands remain a challenge due to low affinity, low specificity, lack of serum stability, and immunogenicity. Therefore, there remains a need to address these problems.

SUMMARY

In accordance with certain embodiments, a nucleic acid molecule capable of binding E-selection is provided. In some embodiments, the nucleic acid molecule capable of binding E-selection prevents interactions between E-selectin and its natural ligands. In some embodiments, the nucleic acid molecule binds E-selectin with nM affinity. In some embodiments, a nucleic acid molecule that selectively binds E-selectin with nM affinity. In some embodiments, a nucleic acid molecule that selectively binds E-selectin comprises a nucleic acid sequence selected from the group of SEQ ID NO: 37-49. In some embodiments, a nucleic acid molecule that comprises modified nucleotides. In some embodiments, a nucleic acid molecule capable of selectively binding E-selection is an aptamer. In some embodiments, the aptamer is a thioaptamer. In some embodiments, a nucleic acid molecule capable of selectively binding E-selection consists of SEQ ID NO: 1.

In some embodiments, an aptamer that binds to E-selectin is selected from the group consisting of: single stranded oligonucleotides identified by SEQ ID NO.: 1, wherein between one and six of the nucleotides are dithiophosphates; double stranded or partially double stranded oligonucleotides comprising the sequence identified by SEQ ID NO: 1, wherein between one and ten of the nucleotides are dithiophosphates; single stranded oligonucleotides identified by SEQ ID NO: 1, wherein between one and six of the nucleotides are dithiophosphates; and double stranded or partially double stranded oligonucleotides having the sequence identified by SEQ ID NO: 1, wherein between one and ten of the nucleotides are dithiophosphates. In some embodiments the aptamer comprises any of SEQ ID NOS: 37-49, wherein the adenosine residues are monothio-substituted phosphates. In some embodiments the aptamer has the sequence of the formula: 5'-CGCTCGGATCGATAAGCTTCGATC-CCACTCTCCCGTTCACTTCTCCTCAC-GTCACG-GATCCTCTAGAGCACTG-3' (SEQ ID NO: 1). In some embodiments, a nucleic acid molecule capable of selectively binding E-selection comprises one or more pharmaceutically acceptable salts.

In some embodiments, an isolated nucleic acid molecule is provided that selectively binds to an E-selectin protein and comprises a contiguous 29-30 nucleotide sequence that includes at least one monothiophosphate or a dithiophosphate modified nucleotide and which contains at least one motif selected from the group consisting of ACTYCWCYTCAC (SEQ ID NO.: 18), TCCTC (SEQ ID NO.: 50), TCCGTT (SEQ ID NO.: 51), TCCCCK (SEQ ID.: 52), ACCCWM (SEQ ID NO.: 53), ACTHC (SEQ ID NO.: 54), TCCCK (SEQ ID NO.: 55), ATCC (SEQ ID NO.: 56), CCGTY (SEQ ID NO.: 57) and CTTCW (SEQ ID NO.: 58), wherein Y=T or C, W=A or T, K=T or G, and M=A, or C, or has the nucleotide sequence of SEQ ID NO.: 31.

In some embodiments, the contiguous 29-30 nucleotide sequence is selected from the group consisting of SEQ ID NO.: 37-49 wherein at least one nucleotide is a monothiophosphate or a dithiophosphate modified nucleotide. In some embodiments, the contiguous 29-30 nucleotide sequence contains at least one deoxyadenosine monothiophosphate. In some embodiments, the isolated nucleic acid molecule has a secondary structure with a free energy of folding in the range of about −8.0 to about −10.7 kcal/mol. In some embodiments, an isolated nucleic acid molecule binds to E-selectin with binding affinity ($K_D$) in the nanomolar to picomolar range. In some embodiments, a contiguous 29-30 nucleotide sequence has the nucleotide sequence of SEQ ID NO.: 37, SEQ ID NO.: 44 or SEQ ID NO.: 48. In some embodiments, a contiguous 29-30 nucleotide sequence is disposed between SEQ ID NO.: 59 at the 5' end and SEQ ID NO.: 60 at the 3' end. In some embodiments, an isolated nucleic acid molecule contains double-stranded stem structures at the 5' and 3' ends.

In some embodiments, a composition comprises an above-described nucleic acid molecule and one or more therapeutic compounds, and/or one or more imaging agents. In some embodiments, the nucleic acid molecule is coupled to a therapeutic agent or an imaging agent, or both. In certain embodiments, the composition comprises a conjugate containing a particle coupled to the nucleic acid molecule. In some embodiments, the imaging agent is attached to the particle or to the nucleic acid molecule, or is attached to both. In some embodiments, a pharmaceutical composition comprises a nucleic acid molecule that selectively binds E-selectin, to target one or more compounds to a tissue expressing E-selectin, wherein binding of the nucleic acid molecule to E-selectin on the target tissue enhances therapeutic activity of the compounds and/or reduces adverse reactions associated with toxicity of the compounds.

In some embodiments, a composition for imaging a target tissue bearing E-selectin, comprises a liposomal nanoparticle and a nucleic acid molecule coupled to the liposomal nanoparticle to form a conjugate wherein the nucleic acid molecule is capable of selectively binding E-selectin on target tissue. In certain embodiments, an imaging agent is associated with the liposomal nanoparticle or the nucleic acid molecule. In some embodiments, a composition for imaging target tissue bearing E-selectin comprises at least one imaging agent; liposomal nanoparticles coupled to a imaging agent; and a nucleic acid molecule coupled to each liposomal nanoparticle to form a conjugate, wherein the nucleic acid molecule selectively binds E-selectin, and targets the composition to tissue bearing E-selectin. In some embodiments, the nucleic acid molecule is a thioaptamer comprising a nucleotide sequence selected from the group of SEQ ID NOs: 37-49. In some embodiments, the nucleic acid molecule comprises a thioaptamer having the nucleotide sequence of SEQ ID NO: 1.

In some embodiments, a composition for imaging target tissue bearing E-selectin comprises at least one imaging agent; liposomal-based gadolinium (Gd) nanoparticles; and nucleic acid molecules capable of selectively binding E-selection to target the composition to tissue bearing E-selectin, wherein each nucleic acid molecule is coupled to a nanoparticle, and a imaging agent is coupled to either the nanoparticles or the nucleic acid molecules, to form a conjugate.

In some embodiments, a composition for imaging vasculature bearing E-selectin, comprises at least one imaging agent; liposomal nanoparticles; and nucleic acid molecules, wherein each nucleic acid molecule is coupled to a liposomal nanoparticle, and a imaging agent is associated with either the liposomal nanoparticles or the nucleic acid molecules, to form a conjugate wherein the nucleic acid molecules bind E-selection on a vessel endothelium when the composition is used for imaging a target vasculature bearing E-selectin. In some embodiments, a composition is provided that delivers a therapeutic agent to inflamed vasculature in a patient. In some embodiments, such method comprises administering intravenously a composition according wherein liposomal nanoparticles contain therapeutic agent; causing conjugate to selectively bind to E-selectin on inflamed vasculature; and causing therapeutic agent to be released from liposomal nanoparticles of conjugate bound to E-selectin on inflamed vasculature. In some embodiments, the nucleic acid molecule is an aptamer, and, in some cases, it is a thioaptamer comprising the nucleotide sequence selected from the group of SEQ ID NOs: 37-49. In some embodiments, the nucleic acid molecule comprises an aptamer having the nucleotide sequence of SEQ ID NO: 1.

In some embodiments, a composition for imaging new or inflamed vasculature bearing E-selectin comprises at least one imaging agent; liposomal nanoparticles; and thioaptamers coupled to liposomal nanoparticles to form a conjugate, wherein the thioaptamers comprise the nucleotide sequence selected from the group of SEQ ID NOs: 37-49, and a imaging agent is associated with either the liposomal nanoparticles or the thioaptamers, to form a conjugate wherein the thioaptamers are capable of selectively binding to E-selectin on new or inflamed vasculature. In certain embodiments, the thioaptamer has the nucleotide sequence of SEQ ID NO: 1.

In some embodiments, a method of making an imaging agent for locating inflamed vasculature in an individual comprises associating one or more imaging agents with a liposomal nanoparticle and/or with an aptamer that selectively binds E-selectin; and coupling the liposomal nanoparticle with the aptamer to form an aptamer-liposomal nanoparticle conjugate associated with at least one imaging agent. In some embodiments, a method of imaging inflamed vasculature comprises administering intravenously to an individual an aptamer-liposomal nanoparticle conjugate associated with at least one imaging agent; causing the conjugate to selectively bind to E-selectin on inflamed vasculature; and visualizing at last one imaging agent associated with the conjugate to identify a location of inflamed vasculature in an individual. In some embodiments, the aptamer is a thioaptamer comprising an above-described contiguous 29-30 nucleotide sequence. In certain embodiments, the nucleotide sequence is selected from the group of SEQ ID NOs: 37-49. In some embodiments, the thioaptamer has the nucleotide sequence of SEQ ID NO: 1.

In some embodiments, a method of delivering an imaging agent to target tissue bearing E-selectin using a nucleic acid molecule capable of selectively binding E-selectin coupled to a particle (e.g., a liposome, a nanoparticle). In some embodiments, the particle is a chitosan nanoparticle. In some embodiments the particle is a liposomal nanoparticle. In some embodiments, a method of delivering siRNA to target tissue bearing E-selectin uses a nucleic acid molecule capable of selectively binding E-selection. In some embodiments, a method of delivering an imaging agent to a target tissue bearing E-selectin uses a nucleic acid molecule capable of selectively binding E-selectin coupled to a liposome.

In some embodiments, a composition for imaging target tissue bearing E-selectin comprises a multistage nanoparticle; a nucleic acid molecule coupled to a multistage nanoparticle, to form a conjugate wherein the nucleic acid molecule is capable of selectively binding E-selectin on target tissue. In certain embodiments, the composition also includes and an imaging agent associated with the multistage nanoparticle or the nucleic acid molecule. In some embodiments, the composition for imaging target tissue bearing E-selectin comprises at least one imaging agent; multistage nanoparticles coupled to a imaging agent; and a nucleic acid molecule coupled to each multistage nanoparticle to form a conjugate, wherein the nucleic acid molecule selectively binds E-selectin, to target the composition to tissue bearing E-selectin. In some embodiments, the nucleic acid molecule is a thioaptamer comprising a nucleotide sequence selected from the group of SEQ ID NOs: 37-49. In some embodiments, the nucleic acid molecule comprises a thioaptamer having the nucleotide sequence of SEQ ID NO: 1. In some embodiments, a composition for imaging tissue bearing E-selectin, comprises at least one imaging agent; multistage nanoparticles; and nucleic acid molecules capable of selectively binding E-selection to target the composition to tissue bearing E-selectin, wherein each nucleic acid molecule is coupled to a said multistage nanoparticle, and a said imaging agent is coupled to either the multistage nanoparticles or the nucleic acid molecules, to form a conjugate.

In some embodiments, a composition for imaging vasculature bearing E-selectin comprises at least one imaging agent; multistage nanoparticles; and nucleic acid molecules, wherein each nucleic acid molecule is coupled to a multistage nanoparticle, and a imaging agent is associated with either the multistage nanoparticles or the nucleic acid molecules, to form a conjugate wherein said nucleic acid molecules bind E-selection on a vessel endothelium when the composition is used for imaging a target vasculature bearing E-selectin.

In some embodiments, a composition for imaging new or inflamed vasculature bearing E-selectin comprises at least one imaging agent; multistage nanoparticles; and thioaptamers coupled to the multistage nanoparticles, wherein the thioaptamers comprise the nucleotide sequence selected from the group of SEQ ID NOs: 37-49, and a imaging agent is associated with either the multistage nanoparticles or the thioaptamers, to form a conjugate wherein the thioaptamers are capable of selectively binding to E-selectin on new or inflamed vasculature.

In some embodiments, a method of making an imaging agent for locating inflamed vasculature in an individual, comprising: associating one or more imaging agents with a multistage nanoparticle and/or with an aptamer that selectively binds E-selectin; and coupling said multistage nanoparticle with the aptamer to form an aptamer-multistage nanoparticle conjugate associated with at least one imaging agent.

In some embodiments, a method of imaging inflamed vasculature comprises administering intravenously to an individual an aptamer-multistage nanoparticle conjugate associated with at least one imaging agent; causing the conjugate to selectively bind to E-selectin on inflamed vasculature; and visualizing imaging agent associated with a conjugate to identify a location of inflamed vasculature in a individual. In some embodiments, the aptamer is a thioaptamer comprising the nucleotide sequence selected from the group of SEQ ID NOs: 37-49.

In some embodiments, a method of delivering a therapeutic agent to inflamed vasculature in a patient, the method comprising administering intravenously to a patient in need thereof, a composition wherein multistage nanoparticles contain said therapeutic agent; causing the conjugate to selectively bind to E-selectin on inflamed vasculature; and causing the therapeutic agent to be released from said multistage nanoparticles of conjugate bound to E-selectin on inflamed vasculature. In some embodiments, the aptamer is a thioaptamer comprising the nucleotide sequence selected from the group of SEQ ID NOs: 37-49.

In some embodiments a method of delivering a therapeutic agent to an individual suffering from an E-selectin associated disorder, comprising one or more therapeutic agents coupled to a nucleic acid molecule capable of selectively binding E-selection. In some embodiments, the therapeutic agent comprises a nanoparticle or is contained in a nanoparticle. In certain embodiments, the nanoparticle comprises chitosan or the nanoparticle comprises a liposome.

In some embodiments, a method of treating an individual having an E-selectin associated disorder includes administering a composition comprising an above-described nucleic acid molecule that selectively binds E-selectin. In some embodiments, the method of treating further comprises administering one or more anti-cancer therapeutics to the individual. In some embodiments, a method of treating an individual with an E-selection associated disorder comprises injecting a composition comprising a nucleic acid molecule that selectively binds E-selectin, and one or more therapeutic agents. In some embodiments, the composition comprises one or more nanoparticles containing a therapeutic agent.

In some embodiments, the E-selectin associated disorder comprises inflamed vasculature in the individual, and wherein the composition comprising a nucleic acid molecule that selectively binds E-selectin, bound to a particle containing one or more therapeutic agents, is administered intravenously to the individual, causing the conjugate to selectively bind to E-selectin on the inflamed vasculature; and causing the therapeutic agent to be released from association with the nucleic acid molecule, to treat said inflamed vasculature. In certain embodiments, the inflamed vasculature comprises tumor vasculature in the individual.

In some embodiments, a method of imaging inflamed vasculature is provided that comprises administering intravenously to an individual in need of such imaging, an above-described composition containing an imaging agent conjugated to a nucleic acid molecule that selective binds E-selectin; causing the conjugate to selectively bind to E-selectin on the inflamed vasculature; and visualizing the imaging agent bound to E-selectin on the inflamed vasculature, to identify a location of inflamed vasculature in the individual. In certain embodiments, the inflamed vasculature comprises tumor vasculature in the individual.

BRIEF DESCRIPTION OF THE DRAWINGS

FIG. 1 is a list of the 35 clones selected and sequenced. The figure shows the alignment of the sequences by ClustalW program. The PCR primer regions in the sequences are underlined. TA-1 is identified as ESTA-1.

FIG. 3 is a list of the random regions of the representative sequences selected based on the energy of the predicted secondary structure. The A residues, shown in bold, have monothio-substitutions at the 5' side.

FIG. 4 is a list of shared sequence motifs identified within the random region of the selected thioaptamers in a sequence family FIG. 5 lists the free energy, relative binding, and relative specificity of the selected thioaptamer sequences. The relative binding and relative specificity are indicated by the number of positive (+) signs. A negative sign (−) indicates that the observed binding was non-specific.

FIG. 8B illustrates the M fold predicted secondary structure of the ESTA-1 (SEQ ID NO:1) of FIG. 8A.

DETAILED DESCRIPTION

Figure 2:
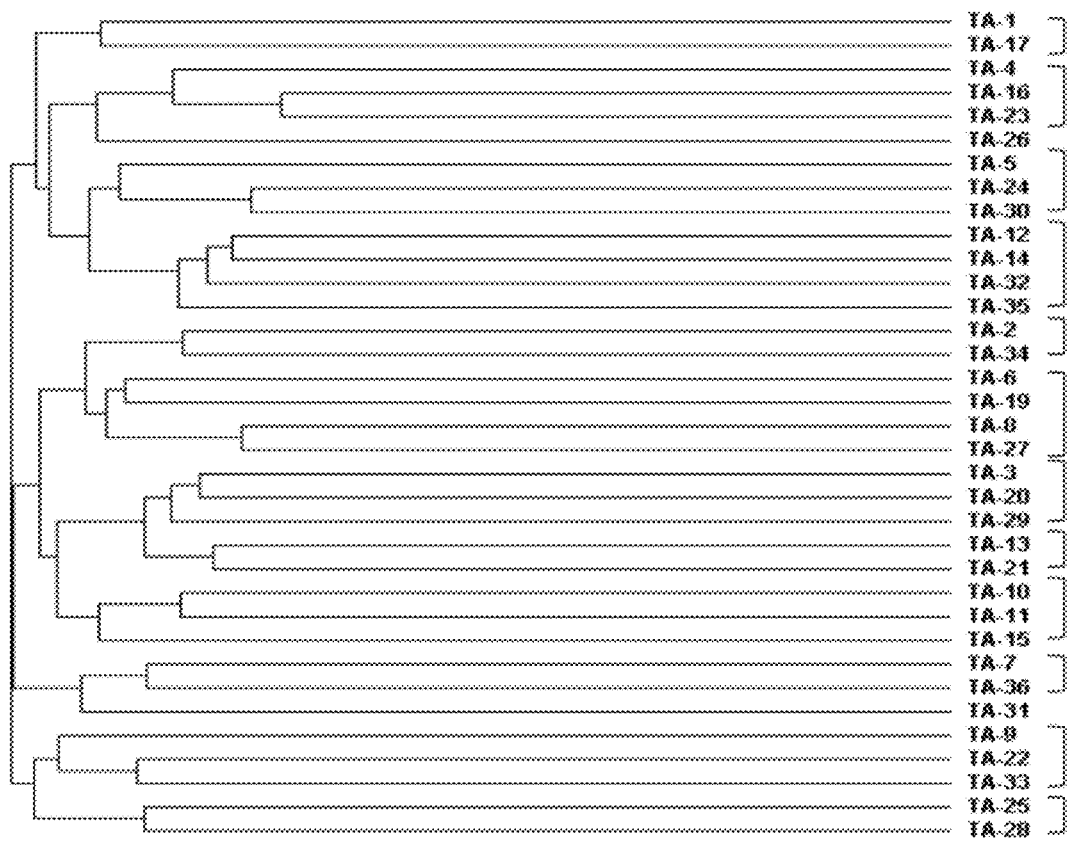
FIG. 2 is a Cladogram of the selected sequences. The sequences from the $10^{th}$ round of selection were aligned by ClustalW. Based on the phylogeny of the sequences they were grouped into 14 different families. The Cladogram shows the phylogeny of the sequences and the grouping of the 14 different families are shown. A single sequence from each family was selected for cell based screening.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Definitions

In this disclosure, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, and unless otherwise indicated, the terms "treat," "treating," "treatment" and "therapy" contemplate an action that occurs while a patient is suffering from disease or disorder that is associated with increased expression of E-selectin and reduces the severity of one or more symptoms or effects of such a disorder, or a related disease or disorder. Where the context allows, the terms "treat," "treating," and "treatment" also refers to actions taken toward ensuring that individuals at increased risk of a disorder associated with increased expression of E-selectin are able to receive appropriate surgical and/or other medical intervention prior to onset of the disorder. As used herein, and unless otherwise indicated, the terms "prevent," "preventing," and "prevention" contemplate an action that occurs before a patient begins to suffer from severe symptoms of disorders associated with increased expression of E-selectin that delays the onset of, and/or inhibits or reduces the severity of disorders associated with increased expression of E-selectin.

As used herein, and unless otherwise indicated, the terms "manage," "managing," and "management" encompass preventing, delaying, or reducing the severity of a recurrence of disorders associated with increased expression of E-selectin in a patient who has already suffered from such a disease or condition. The terms encompass modulating the threshold, development, and/or duration of the disorders associated with increased expression of E-selectin or changing how a patient responds to the disorders associated with increased expression of E-selectin.

As used herein, and unless otherwise specified, a "therapeutically effective amount" of a compound is an amount sufficient to provide any therapeutic benefit in the treatment or management of disorders associated with increased expression of E-selectin or to delay or minimize one or more symptoms associated with disorders associated with increased expression of E-selectin. A therapeutically effective amount of a compound means an amount of the compound, alone or in combination with one or more other therapies and/or therapeutic agents, that provides any therapeutic benefit in the treatment or management of disorders associated with increased expression of E-selectin, or related diseases or disorders. The term "therapeutically effective amount" can encompass an amount that alleviates disorders associated with increased expression of E-selectin, improves or reduces disorders associated with increased expression of E-selectin, improves overall therapy, or enhances the therapeutic efficacy of another therapeutic agent. The "therapeutically effective amount" can be identified at an earlier stage with parameters such as levels of E-selectin expression as identified herein.

As used herein, and unless otherwise specified, a "prophylactically effective amount" of a compound is an amount sufficient to prevent or delay the onset of disorders associated with increased expression of E-selectin, or one or more symptoms associated with disorders associated with increased expression of E-selectin or prevent or delay its recurrence. A prophylactically effective amount of a compound means an amount of the compound, alone or in combination with one or more other treatment and/or prophylactic agent that provides a prophylactic benefit in the prevention of disorders associated with increased expression of E-selectin. The term "prophylactically effective amount" can encompass an amount that prevents disorders associated with increased expression of E-selectin, improves overall prophylaxis, or enhances the prophylactic efficacy of another prophylactic agent. The "prophylactically effective amount" can be prescribed at an earlier stage with parameters of E-selectin expression as identified herein.

"Diseases and disorders associated with E-selectin," include, but are not limited to, seizures, mental illness, dementia, diabetes, Alzheimer's disease, depression, kidney disease, digestive/bowel disorders, high blood pressure, cardiopulmonary disease, cardiovascular, arterial endothelial or angiogenic disorders, fibrotic diseases and chronic obstructive pulmonary disease, infectious disease, immune mediated, autoimmune and inflammatory disorders (such as, but not limited to, NK cell mediated disease, systemic lupus erythematosis, rheumatoid arthritis, osteoarthritis, juvenile chronic arthritis, spondyloarthropathies, systemic sclerosis, idiopathic inflammatory myopathies, Sjogren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barre syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft—versus-host-disease), engraftment of hematopoietic progenitor cells, bone marrow transplantation related disorders, neoangiogeneis, bone disease, wound healing, vascular proliferation, various pathologic maternal/fetal conditions (such as intra-amniotic infection, or chromosomal defects), autoimmune diseases, thrombocytopenia, (such as, but not limited to, drug induced thrombocytopenia, idiopathic thrombocytopenic purpura, thrombotic thrombocytopenic purpura, post-transfusion purpura, hemolytic-uremic syndrome, disseminated intravascular coagulation, malignant hypertension, eclampsia, vasculitis associated with systemic autoimmune disorders), thrombosis, myocardial infarction and acute cardiac syndrome, arrhythmia, cancers (such as, but not limited to, cancers of the bladder, kidney, prostate, breast, colon, ovary and pancreas, leukemia, acute lymphoblastic leukemia and secondary acute myeloid leukemia), obesity, connective tissue disorders, cardiovascular, endothelial or angiogenic disorders or arterial diseases, such as diabetes mellitus; pathological angiogenesis and increased vascular permeability in important eye diseases such as diabetic retinopathy; age-related macular degeneration; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis (collectively referred to herein as "E-selectin associated disorders").

"Aptamers" are oligo-nucleic acid or peptide molecules that bind to a specific protein target molecule (see, for example, the following patent documents: U.S. Pat. Nos. 5,756,291; 754,679; US2006/0105975; WO1992/014843; WO2003/099840 and EP1562981).

"Thiophosphate oligonucleotide aptamers," "thioaptamers" or "TAs" are a new class of ligand that structurally differs from RNA and DNA and can bind proteins with high (nM) affinity. TAs are often superior to conventional peptide ligands or antibodies due to unique chemical and biological properties which include, but are not limited to, high affinity for protein targets, resistance to nucleases, and lack of immunogenicity.

Overview

Targeting of E-selectin offers a promising therapeutic strategy to control the pathologic inflammation and the infiltration of leukocytes and/or metastatic cancer cells. Inhibition of E-selectin-mediated rolling and/or adhesion and diapedesis has been demonstrated using various E-selectin ligands, such as monoclonal antibodies, peptides, and carbohydrate ligands. These methods of blocking E-selectin have been shown to bind inflamed vasculature in experimental animal models and the human clinical trials. However, application of these ligands for treatment of E-selectin associated disorders has been limited by one or more of the following factors: low affinity; lack of selectivity or specificity; lack of stability and in some cases even immunogenicity. Many embodiments of the presently disclosed compositions and methods utilize aptamers with favorable in vivo characteristics that bind E-selectin protein with high affinity and specificity greatly facilitate diagnostic and prognostic imaging abilities. This makes it possible to now address many E-selectin associated disorders, as well as a specific methods of targeting theraputics to tissue that expresses E-selectin, such as that of inflamed vasculature.

Aptamers and Thioaptamers

Methods for making and combinatorial selection of aptamer and TA libraries consisting of 1014 random sequences have identified aptamers and TAs that bind to a wide variety of target proteins (see for example, Bhushan M, et al. (2002) Anti-E-selectin is ineffective in the treatment of psoriasis: a randomized trial. *Br J Dermatol* 146: 824-831; Magnani J L, Ernst B (2009) Glycomimetic drugs—a new source of therapeutic opportunities. *Discov Med* 8: 247-252; King D J, Ventura D A, Brasier A R, Gorenstein D G (1998) Novel combinatorial selection of phosphorothioate oligonucleotide aptamers. *Biochemistry* 37: 16489-16493). Details regarding the generation, characterization, modification and use of thioaptamers can be found in, for example, U.S. Pat. Nos. 6,423,493, 6,867,289, 7,179,894, 7,338,762, 7,576,037 and U.S. Patent Application Nos.: US20100056516, US20100124563, US20100120665, US20030162190, US20030027184, US20040242521, US20040265912, US20050239134, US20050118611, US20050123939, US20050214772, US20060121489, US20060014172, US20060281702, US20060172925, US20060160169, US20070009428, US20070009427, US20070117099, US20070190155, US20070243547, US20080269156, US20080171322, US20080044834, US20080177246, US20080108583, US20080311182, US20080200340, US20080255005, US20090123922, US20090305281, US20090105173, US20090111094, US20090202990, US20090304803, US20090215864 and US20100029746.

The majority of screenings of aptamer libraries utilize screening with either full-length or fragments of recombinant proteins. However, the structural differences that result from the lack of post-translational modifications and possible misfolding of the recombinant proteins may fail to identify aptamers that would maintain their binding capabilities in a physiological environment. The present disclosure describes the addition of biologically relevant conditions as a part of the screening process and this was used to identifying aptamers that function in a biological environment. Specifically, a two-step aptamer selection strategy was employed to identify the presently disclosed E-selectin binding aptamers. First a recombinant protein-based selection from the library followed by a cell-based binding screen identified TA that binds native E-selectin.

The first step of the selection experiments with thiooptmer library were done with the recombinant E-selectin protein. After 10 rounds of selection, 35 sequences (FIG. 1) were selected from the TA library. Based on the primary sequence alignment of the selected sequences, using ClustalW program, a Cladogram was generated that shows the phylogeny of the sequences and the grouping of families are shown phylogram tree was generated to group sequences into 14 different sequence families (FIG. 2). This resulted in 14 sequence families. One sequence from each family, based on the energy of the predicted secondary structure, was selected for the second phase of the screening using the E-selectin expressing cells. The random regions of these selected sequences are shown in FIG. 3. The common sequence motifs identified among them are shown in the table of FIG. 4.

Figure 6A:
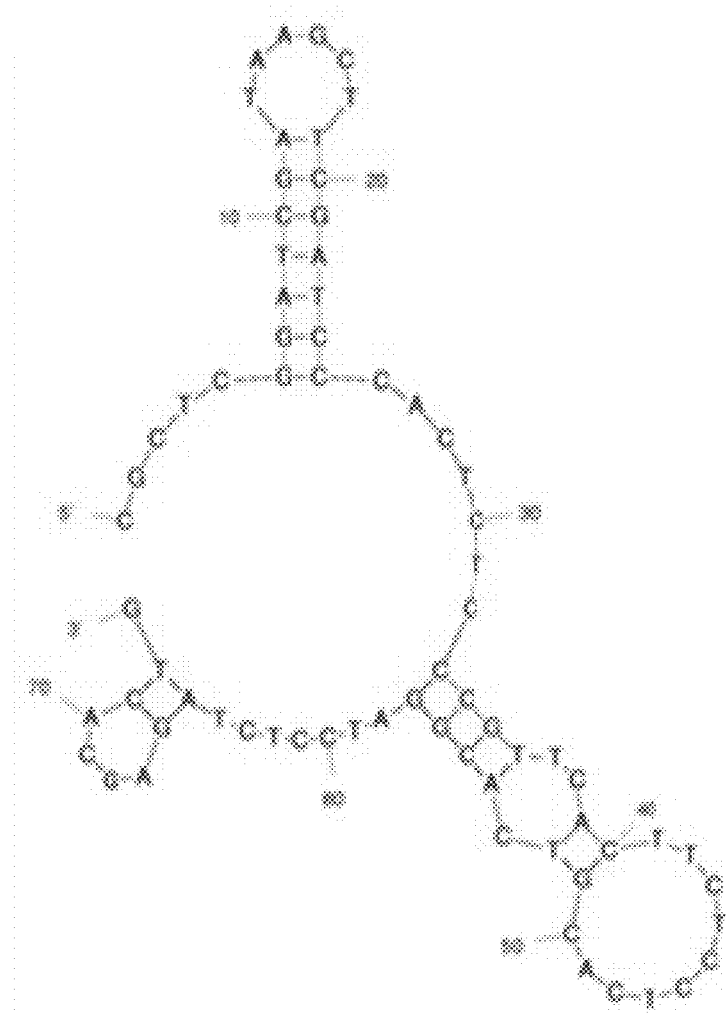
FIG. 6A illustrates the predicted secondary structure of ESTA-1 (SEQ ID NO:1) using MFOLD, with the free energy shown below the structure.

The relative binding affinities and specificities of the TA sequences were found to correlate with the energy of the structures predicted by MFOLD. This is shown in the table of FIG. 5. Among the 14 selected sequences, three TAs (ESTA-1, ESTA-20, and ESTA-31) showed the lowest free energy, as predicted by MFOLD, as well as binding to the E-selectin expressing cells. The MFOLD prediction exhibited a single secondary structure for ESTA-1 (with an estimated free-energy of folding of −10.72 kcal/mol) containing two stable hairpin loops (FIG. 6A).

Figure 6B:
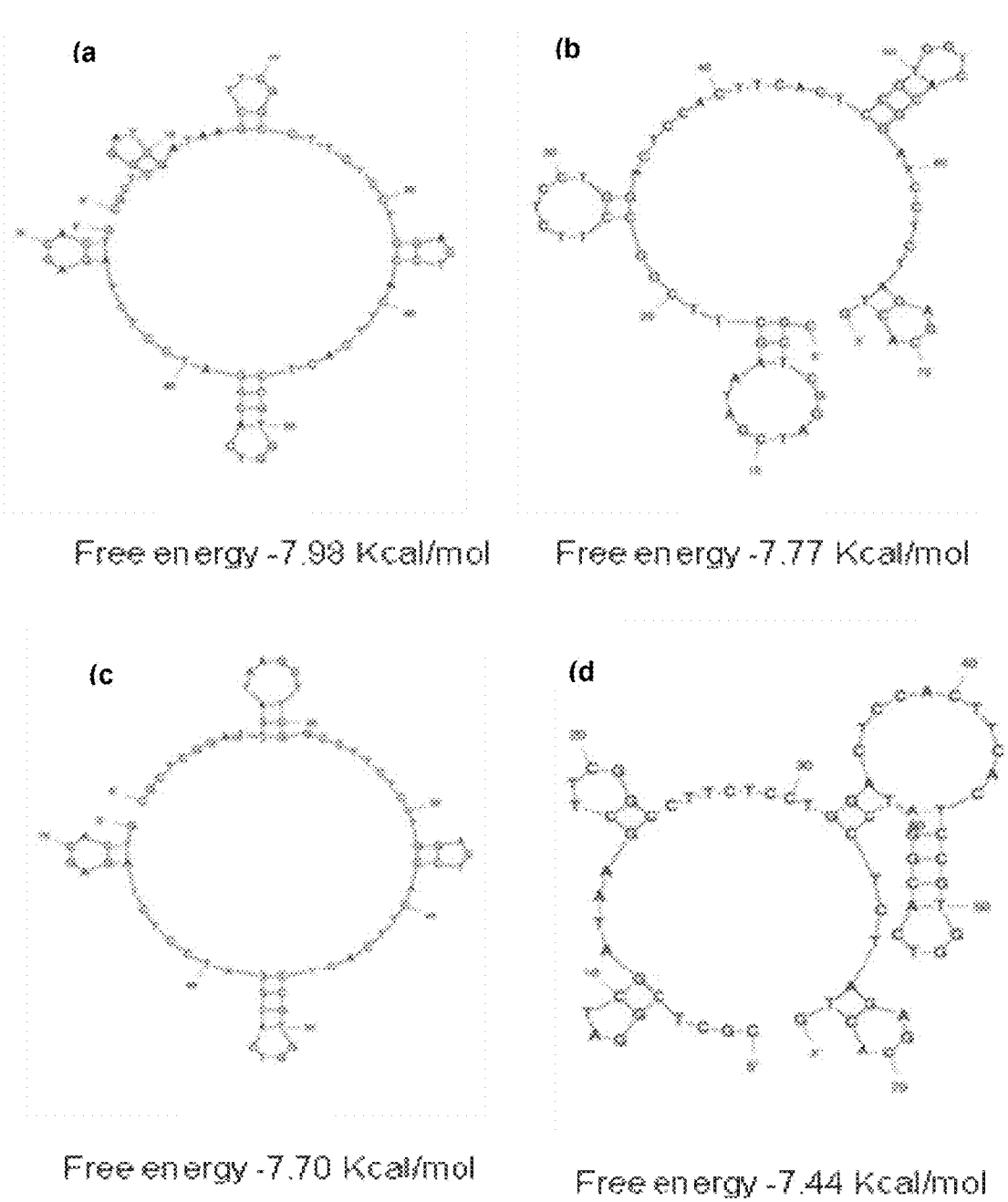
FIG. 6B illustrates the predicted secondary structure of ESTA-20 (SEQ ID NO:20) using MFOLD, with the energy shown below the structure.
Figure 6C:
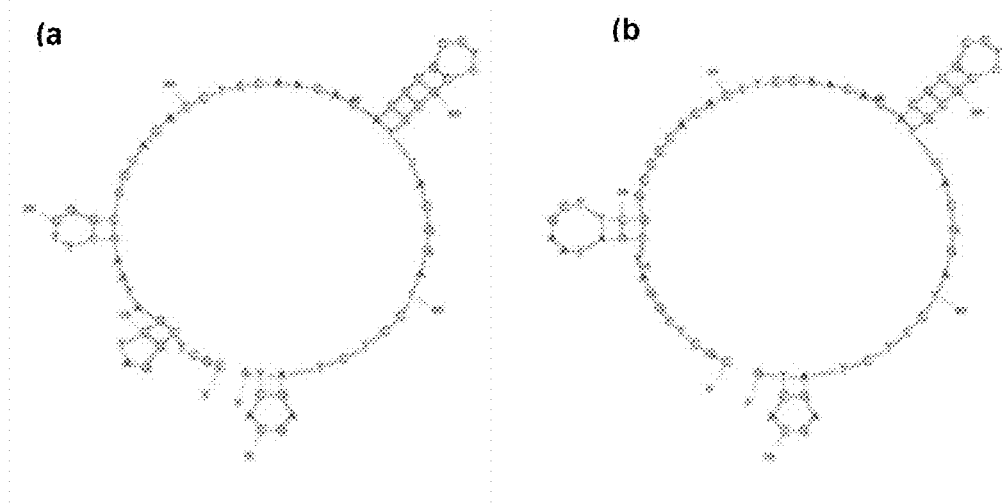
FIG. 6C illustrates the predicted secondary structure of ESTA-31 (SEQ ID NO:31) using MFOLD, with the free energy shown below the structure.

Among these three, ESTA-1 (10-1) showed the lowest predicted free energy (−10.72 kcal/mol), highest relative binding affinity and specificity. The MFOLD program identified a potential common secondary structural motifs among ESTA-1, ESTA-20 and ESTA-31. The MFOLD prediction exhibited a single secondary structure for ESTA-1 (with an estimated free-energy of folding of −10.72 kcal/mol) containing two stable hairpin loops (FIG. 6A). In contrast MFOLD predicted four secondary structures for ESTA-20, (a) dG=−7.98; (b) dG to −7.77; (c) dG=−7.70; and (d) dG=−7.44 kcal/mol (FIG. 6B); and four secondary structures for ESTA-31 (a) dG=−8.64; (b) dG=−8.36; (c) dG=−8.08; and (d) dG=−7.94 kcal/mol) (FIG. 6C). Only a single stable hairpin loop was predicted in each of these structures for ESTA-20 and ESTA-31 (FIGS. 6B and 6C). In contrast MFOLD predicted four secondary structures for both ESTA-20 (dG=−7.98 to −7.44 kcal/mol) and ESTA-31 (dG=−8.64 to −7.94 kcal/mol) with comparable free energy values, and only a single stable hairpin loop was predicted in each of these structures (FIGS. 6B and 6C). The two highest binders, ESTA-1 and ESTA-20, share the ACT(T/C)C(T/A)C(T/C)TCAC (SEQ ID NO: 18) sequence motif in the loop region of the hairpin stem-loop, suggesting that this region may be involved in binding to E-selectin. Presumably the second hairpin loop in ESTA-1 but not in ESTA-20 contributes to its increased affinity and specificity. While not wishing to be limited to any particular theory to explain the binding mechanism, it is noted that the second hairpin loop in ESTA-1 but not in ESTA-20 may contribute to its increased affinity and specificity. Based on these results, ESTA-1 was chosen for further characterization.

It was surprising that only one of the 14 TAs exhibited binding of endothelial cells expressing E-selectin that was highly doxycycline-dependent, despite that the initial screening was carried out using human recombinant E-selectin protein isolated from a mammalian system. Successful ligand screening requires two independent parameters, affinity and specificity to the target. Screening of a ligand from large library pool using a single target molecule will yield a successful identification of high affinity ligands. However, specificity of the ligand to the target protein is better addressed when appropriate biologically relevant parameters are integrated. In fact, the initial screening of TA from random library yielded TA ligands of relatively high affinity, yet with lower specificity (less doxycycline-dependent binding) to the E-selectin expressing cells. These data show that in vitro selection with pure biochemical entities (e.g., recombinant protein) in solution will not readily translate into the ligand binding in a complex biological environment. Thus, the integration of biologically relevant conditions into screening protocols facilitated the identification of aptamers that play the expected functional roles. The most widely accepted approach for functional characterization of E-selectin relied on the TNF-α challenge that mimics gross phenotypic changes on endothelial cell surface in response to inflammatory stimuli including E-selectin, P-selectin, and cell adhesion molecules (CAMs). To focus on a single molecule, yet integrate biologically relevant conditions an E-selectin Tet-on inducible system was developed in endothelial cells for the second selection step. This system facilitated reproducible and controllable E-selectin expression, thereby facilitating the selection of E-selectin-specific binder and exclusion of non-specific binders.

E-selectin expression on the vasculature is a hallmark of inflammation and mediates rolling and extravasation of leukocytes at the site of inflammation. Abundant infiltration of leukocytes to the target tissue can lead to pathological inflammatory conditions such as diabetes, arthrosclerosis, angiogenesis, autoimmune disorders and cancers. In the case of cancer, infiltrated leukocytes secrete cytokines and stimulate the activation of fibroblasts, resulting in a degradation of extracellular matrix and local invasion of cancer cells. The interaction of metastatic cancer cells with endothelial cells via E-selectin induces a bidirectional signaling that results in the activation of the ERK-Src pathway in the tumor cells and increased endothelial permeability, facilitating the transendothelial migration of cancer cells. Clearly, an E-selectin antagonist that blocks E-selectin-mediated leukocyte rolling and/or adhesion and diapedesis, would have great potential utility. In some embodiments, a disclosed aptamer that selectively binds E-selectin may act as a blocking ligand to inhibit E-selectin-mediated rolling and/or adhesion and thus diapedesis. The affinity of the natural ligand for E-selectin ($sLe^x$) is weak (KD=100-2000 µM, IC50=100-750 µM). This has allowed the development of antagonistic ligands for E-selectin including humanized monoclonal antibodies, peptide and carbohydrate ligands that exhibit selective binding to the E-selectin. However, the low affinity (µM range KD) that characterizes the vast majority of these ligands results in increased IC50 (µM), thus significantly limiting their efficacy and therapeutic potential. In some embodiments, a disclosed thioated oligonucleotide-based E-selectin ligand has nanomolar range KD and IC50, as represented by ESTA-1.

ESTA-1 binding to E-selectin expressed on the tumor-associated vasculature in patients with ovarian, breast and skin carcinomas is shown in the examples below. This confirms both the affinity and avidity of ESTA-1 and demonstrates that aptamers that selectively bind E-selectin, such as ESTA-1, also do so under physiological conditions. In addition, the binding of ESTA-1, at nanomolar concentrations, resulted in an approximately 80% inhibition of subsequent attachment of $sLe^x$ positive leukocytes and metastatic breast cancer cells to the endothelial cells. Collectively, this binding represents a significant improvement, with at least a 10,000 time higher affinity and 1,000 times lower IC50 than the binding of the natural ligand $sLe^x$. This is the first report to demonstrate high affinity binding accompanied with inhibition of $sLe^x$ positive cell adhesion to E-selectin at nanomolar range, and presents opportunity for therapeutic applications of aptamers that selectively bind E-selectin, such as ESTA-1, for E-selectin targeted therapy.

All three selectins bind a common carbohydrate domain shared by sialyl Le A/X, due to structural similarities among selectins. Therefore, most of the carbohydrate mimetics and ligands identified against E-selectin have also shown considerable cross reactivity against L- and P-selectin. A lack of selectivity has been a major obstacle to clinical applicability of such molecules, since P-selectin and L-selectin are constitutively expressed on endothelial cells and platelets, respectively. Thus, to be effective and safe an antagonistic ligand, or ligand used to target therapy to E-selectin must be selective in it binding activity. The presently disclosed aptamer that selectively binds E-selectin, ESTA-1, binds E-selectin with high affinity (KD=153 nM) and demonstrates negligible cross-reactivity to L-selectin and P-selectin. Minimal cross reactivity of the aptamer ESTA-1 further highlights its usefulness for highly selective E-selectin targeting of therapeutics and imaging applications.

In some embodiments, a disclosed aptamer that selectively binds E-selectin, such as the thioaptamer ESTA-1, provides safe and effective antagonistic ligands that block E-selectin mediated interactions such as, but not limited to, rolling and/or adhesion and thus diapedesis by leukocytes or metastatic cells, etc., and therefore, may be used to treat E-selectin associated disorders.

In some embodiments, a disclosed aptamer, such as ESTA-1, selectively binds E-selectin and can be used to diagnose, image or target therapies to the areas in which E-selectin expression occurs or has increased.

In some embodiments, a disclosed aptamer, such as ESTA-1, that selectively binds E-selectin may be used to target therapeutic agents to the areas of inflammation in which E-selectin is expressed.

In additional embodiments, aptamers that selectively bind E-selectin, such as ESTA-1, can impair the adhesion of cells such as leukocytes to the vessel walls which is a critical step in tissue infiltration. Therefore, the administration of ESTA-1, for example, via the intravenous route, may be used in some cases to control pathological inflammation by inhibiting leukocyte infiltration. As evidenced in the examples, it was found that ESTA-1 binding inhibits leukocyte adhesion to the endothelial cell surface, and thus the administration of ESTA-1 may be used to control infiltration of leukocytes to the tissues and thus inflammation and other E-selectin mediated processes.

In other embodiments, a disclosed aptamer, such as ESTA-1, that selectively binds E-selection, may be used to identify or image tumor vasculature and target therapies to tumor vasculature. In primary tumors, excessive diapedesis of immune cells can aid in tumor progression. In some embodiments, a disclosed aptamer, such as ESTA-1, that selectively binds E-selectin, may be used to prevent primary tumor growth and progression. As detailed in the examples, ESTA-1 binding to E-selectin expressing cells inhibited "in vitro" adhesion of "leukocyte like" HL-60 cells and metastatic breast tumor cells, which express a counter ligand for E-selectin. The presently described examples clearly demonstrate that aptamers that selectively bind E-selectin, such as ESTA-1, can bind to tumor vasculature of both human and mouse tissue and prevent the binding of metastatic cells to the vessel surfaces. Therefore, aptamers that selectively bind E-selectin, such as ESTA-1, can be used to inhibit adhesion of metastatic cancer cells to, for example, vascular endothelial cells, and also be used to reduce the metastasis of cells that often accompanies cancers such as, but not limited to, breast or prostate cancer, and bind to E-selectin and thus provide a blockade to the initial contact between metastatic cancer cells expressing E-selectin ligand and E-selectin expressed on the vessel wall.

Inflamed vessels often express elevated levels of E-selectin and E-selectin antibodies have been used for in vivo imaging of inflammatory sites. For some applications a disclosed aptamer, such as ESTA-1, that selectively binds E-selectin is conjugated to a fluorescent dye (as described in the examples section) or to a radioisotope. Aptamers, such as ESTA-1, that selectively bind E-selectin are superior to the use of an antibody for forming conjugates because aptamers are less expensive to generate, are more easily modified chemically, and do not generate anti-aptamer immune responses.

The presence of soluble E-selectin in the serum has been shown to be an important diagnostic marker in some malignancies. Therefore, in some embodiments, the presently described aptamer, such as ESTA-1, that selectively bind E-selectin are used to quantify soluble E-selectin in the serum.

E-selectin is a cell membrane protein that undergoes recycling via receptor internalization, thus E-selectin may be used to facilitate intracellular delivery of therapeutics. In some embodiments, aptamers, such as ESTA-1, that selectively bind E-selectin are conjugated to nanoparticles, for example, which themselves are associated with imaging or therapeutic agents, which, once bound to E-selectin, target delivery of the nanoparticles to inflamed endothelial cells. For some applications, nanoparticles comprising chitosan may be used.

Because, for example, ESTA-1 shows high affinity for E-selectin, the presently described aptamers that selectively bind E-selectin, such as ESTA-1, can be used for the detection of E-selectin expression on cells or in tissue using techniques similar to western blotting, immunohistochemistry, immunofluorescence, flow cytometry, etc., wherein the presently described aptamers that selectively bind E-selectin, act as a replacement of E-selectin binding antibody during such techniques.

In some embodiments, a disclosed aptamer, such as ESTA-1, that selectively bind E-selectin may be used to target therapeutic agents to the areas in which E-selectin is expressed.

In some embodiments, a disclosed aptamer, such as ESTA-1, that selectively binds E-selectin may be used to target therapeutic agents to the areas of inflammation in which E-selectin is expressed. Some non-limiting examples of such therapeutic agents include chemical or nuclear agents, biologic agents, drugs or small molecules, large molecules, macroparticles, microparticles, nanoparticles. Such particles may comprise a single stage or a multistage particle (as described for example in US Patent App. Pub. No. 2008/0311182), cancer chemotherapeutics and biologic agents. Therapeutic agents may be any physiologically or pharmacologically active substance that may produce a desired biological effect in a targeted site in an animal, such as a mammal or a human. The therapeutic agent may be any inorganic or organic compound, without limitation, including peptides, proteins, nucleic acids, and small molecules, any of which may be characterized or uncharacterized. The therapeutic agent may be in various forms, such as, but not limited to, unchanged molecules, molecular complex, pharmacologically acceptable salt, such as hydrochloride, hydrobromide, sulfate, laurate, palmitate, phosphate, nitrite, nitrate, borate, acetate, maleate, tartrate, oleate, salicylate, and the like. For acidic therapeutic agent, salts of metals, amines or organic cations, for example, quaternary ammonium may be used. Derivatives of drugs, such as bases, esters and amides also may be used as a therapeutic agent. A therapeutic agent that is water insoluble may be used in a form that is a water soluble derivative thereof, or as a base derivative thereof, which in either instance, or by its delivery, is converted by enzymes, hydrolyzed by the body pH, or by other metabolic processes to the original therapeutically active form.

The therapeutic agent may be a chemotherapeutic agent, an immunosuppressive agent, a cytokine, a cytotoxic agent, a nucleolytic compound, a radioactive isotope, a receptor, and a pro-drug activating enzyme, which may be naturally occurring or produced by synthetic or recombinant methods, or any combination thereof. In some embodiments this involves the use of drugs that are affected by classical multidrug resistance, such as, but not limited to, vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel) may have particular utility as the therapeutic agent.

For some applications, cancer chemotherapeutic agents may be a preferred therapeutic agent. Nonlimiting examples of useful cancer chemotherapy drugs include nitrogen mustards, nitrosoureas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda. Cancer chemotherapy drugs also include alkylating agents, such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitrogen mustards such as Chlorambucil, Chlomaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitrosureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylomithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

In some embodiments, biologic agents, such as cytokines, may be also used as the therapeutic agent. Nonlimiting examples of such cytokines include lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor (VEGF); integrin; thrombopoietin (TPO); nerve growth factors such as NGF-$\beta$; platelet growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$ and -$\gamma$; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-$\alpha$ or TNF-$\beta$; and other polypeptide factors including LIF and kit ligand. As used herein, the term cytokine includes proteins from natural sources or from recombinant cell culture and biologically active equivalents of the native sequence of such a biologic agent.

In some embodiments a disclosed aptamer, such as ESTA-1, that bind E-selectin may be used to deliver imaging agents. Nonlimiting examples of such imaging agents include: radioactive metal ions or a radiometal, (suitable radiometals can be either positron emitters such as 64 Cu, 48 V, 52 Fe, 55 Co, 94m Tc or 68 Ga; or $\gamma$-emitters such as 99m Tc, 111 In, 113m In, or 67 Ga or $\gamma$-emitters such as 99m Tc, 111 In, 113m In, or 67 Ga); a paramagnetic metal ions (suitable such metal ions include, but are not limited to: Gd(III), Mn(II), Cu(II), Cr(III), Fe(II), Co(II), Er(II), Ni(II), Eu(III) or Dy(III). Preferred paramagnetic metal ions are Gd(III), Mn(II) and Fe(III), with Gd(III)); gamma-emitting radioactive halogen (such as 123 I, 131 I or 77 Br); a positron-emitting radioactive non-metal, suitable such positron emitters include, but are not limited to: 11 C, 13 N, 15 O, 17 F, 18 F, 75 Br, 76 Br or 124 I); a hyperpolarised NMR-active nucleus (such NMR-active nuclei have a non-zero nuclear spin, and include, but are not limited to: 13C, 15N, 19F, 29Si and 31P) or even metals such as gold or silver particles.

In some embodiments the imaging moiety is a reporter suitable for in vivo optical imaging. Such a reporter is any moiety capable of detection either directly or indirectly in an optical imaging procedure. The reporter might be a light scatterer (e.g., a colored or uncolored particle), a light absorber or a light emitter, or a chromophore or a fluorescent compound. The dye can be any dye that interacts with light in the electromagnetic spectrum with wavelengths from the ultraviolet light to the near infrared. Nonlimiting examples of reporter moieties include organic chromophoric and fluorophoric reporters with groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful as reporters. Complexes of certain rare earth metals (e.g., europium, samarium, terbium or dysprosium) are used in certain contexts, as are fluorescent nanocrystals (quantum dots). Particular examples of chromophores which may be used include, but are not limited to: fluorescein, sulforhodamine 101 (Texas Red), rhodamine B, rhodamine 6G, rhodamine 19, indocyanine green, Cy2, Cy3, Cy 3B, Cy3.5, Cy5, Cy5.5, Cy7, Cy7.5, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647-Alex-660, Alex Fluor 68, Alexa Fluor 700, and Alexa Fluor 750.

In some embodiments, dyes which have absorption maxima in the visible or near infrared (NIR) region, between 400 nm and 3 µm, particularly between 600 and 1300 nm are preferred. Optical imaging modalities and measurement techniques include, but not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarisation, luminescence, fluorescence lifetime, quantum yield, and quenching. Examples of imaging moieties are those which can be detected externally in a non-invasive manner following administration in vivo, such as by means of SPECT, PET and MR. Most preferred imaging moieties are radioactive, especially radioactive metal ions, gamma-emitting radioactive halogens and positron-emitting radioactive non-metals, particularly those suitable for imaging using SPECT or PET. For some applications, however, other imaging moieties are preferred, e.g. for imaging AMD optical imaging moieties are preferred.

In some embodiments, the imaging agent may be an ultrasound contrast agent, such as a micro or nanobubble, echogenic immunoliposomes (as described in U.S. Pat. Nos. 5,612,057 and 5,858,399 or US Patent Application Publication No: 2008/0175893, for example) and iron oxide micro or nanoparticles.

New anti-angiogenesis therapeutic strategies, such as blocking or targeting therapies using the aptamers that selectively bind E-selectin, such as the representative aptamer ESTA-1, are badly needed. The progressive growth of many tumors and associated metastases is dependent on an adequate blood supply (angiogenesis). Despite advances in surgery and chemotherapy, ovarian cancer remains the most deadly gynecologic malignancy. Therefore, new treatments are urgently needed. Targeting angiogenesis is a particularly attractive strategy because of the presumed genetic stability of endothelial cells. This is best illustrated by recent successes of anti-angiogenic therapy with monoclonal antibody against VEGF (e.g., bevacizumab) in patients with solid tumors. However, despite initial responses, most patients eventually develop tumor progression resulting in their demise. Therefore, new anti-angiogenesis therapeutic strategies such as blocking or targeting therapies using the aptamers that selectively bind E-selectin, as represented by ESTA-1, are potentially of therapeutic value because E-selectin has been associated with angiogenesis. Therapeutic applications involving targeted nanoparticle associated therapeutics may address limitations known to accompany current therapeutics. Such limitations include poor intracellular uptake, off-target effects, and rapid enzyme degradation. To overcome these and other technical problems, "smart" ESTA-1-targeted nanoparticles may be used to selectively deliver therapeutics to tumor vasculature, for example. Particular nanoparticles may be selected based on the ability to control particle size, efficiency of delivery of the therapy/nanoparticle to tumor, and biocompatibility with biological systems.

To target angiogenesis and tumor growth in vivo and to deliver nanoparticle-associated therapeutic or imaging agents specifically to tumor vasculature, nanoparticles are coupled to aptamers that selectively bind E-selectin, such as ESTA-1. This technology offers a multifunctional platform that facilitates the concentration of a large quantity of payload to the intended locations within the body. This site-specific active targeting of nanoparticles is highly desirable, and may expand the therapeutic window of many treatment modalities. In some embodiments, association or coupling nanoparticles to aptamers that selectively bind E-selectin, such as ESTA-1, will facilitate targeted delivery of the nanoparticle and its imaging or therapeutic payload directly to tumor vasculature. By specifically targeting a tumor, the presently described system will enhance activity, such as the therapeutic effect and will greatly reduce the amount of the therapeutic nanoparticle-aptamer composition required to achieve the desired effect. A reduction in the amount of therapeutic or imaging agent administered will greatly enhance the safety profile of the composition, for example by decreasing the chance of off target effects, as well as reduce costs.

To target angiogenesis and tumor growth in vivo and to deliver therapeutic or imaging agents specifically to tumor vasculature, nanoparticles are coupled to aptamers that selectively bind E-selectin, such as ESTA-1. The presently described methods and compositions comprising the use of aptamers that selectively bind E-selectin, such as ESTA-1, offer unique advantages by the targeting of E-selectin, because unlike other adhesion molecules which are constitutively expressed on the normal vessels, E-selectin expression is normally absent and is induced by, among others, inflammatory cytokines, which are commonly detected in and around atherosclerotic lesions. Thus, alone or in combination with nanoparticle associated therapies, aptamers such as ESTA-1, that selectively bind E-selectin may be effectively used for in vivo treatment of atherosclerotic lesions as well as tumors, thus providing a new and selective therapeutic approach for cancer therapy.

In some applications, nanoparticles covalently coupled or otherwise chemically or physically associated to aptamers that selectively bind E-selectin, such as ESTA-1, may be applied to cardiovascular diseases and disorders. Out of all cardiovascular deaths in the U.S. and Europe, coronary artery disease is the single largest killer: In 2005, coronary artery disease accounted for more than 445,687 deaths (1 in 4). Atherosclerotic lesions (atheromata) are asymmetric focal thickenings of the innermost layer of the artery, the intima. These lesions consist of cells, connective-tissue elements, lipids, and debris. Development of atherosclerotic lesions is preceded by fatty streaks, which are accumulations of lipid-laden cells beneath the endothelium. Abnormal wall shear stress patterns and the presence of cytokines stimulate the vascular endothelial cells to produce an inflammatory response that includes expression of adhesion molecules such as E-selectin, P-selectin, intracellular adhesion molecule-1 (ICAM-1) and vascular cell adhesion molecule-1 (VCAM-1). These phenotypic changes on the surface of endothelial cells and the accompanying disturbed laminar flow facilitate recruitment of monocytes to the surface of endothelial cells, with transmigration of monocytes into the subendothelial space. Monocytes then differentiate to become activated macrophages, which bind to highly-oxidized low-density lipoprotein (LDL) to form foam cells. The death of foam cells leaves behind a growing mass of extracellular lipids and other cell debris along with the accumulation of smooth muscle cells, which result in formation of fibrous plaques. Plaques with thin fibrous caps are vulnerable to rupture and elicit acute coronary syndrome. Thus, early detection of plaque formation as well as stabilization of plaques by controlling inflammatory responses on the surface of the endothelium is critical to prevent rupture of the rupture-prone vulnerable plaque. The ability of aptamers that selectively bind E-selectin, such as ESTA-1, alone or in combination with nanoparticles, such as but not limited to, liposomal nanoparticles can target and disrupt the rolling and/or adhesion of monocytes on the surface of endothelial cells and thus limit the development of atheroma.

Additionally, in some embodiments, nanoparticles are coupled to thioaptamers that selectively bind E-selectin, such as ESTA-1, to facilitate targeted delivery of imaging agents into atherosclerotic lesions. In one embodiment, a multifunctional nanoparticle approach comprised of nanoparticles that are targeted using aptamers to atherosclerotic plaques for early detection of plaque formation and therapy. For atherosclerotic plaque specific targeting, nanoparticles (liposome and microbubbles) that contain imaging contrast agents are further conjugated with thioaptamers that selectively bind E-selectin, such as ESTA-1, which is overexpressed on the surface of inflamed endothelium. In some embodiments, imaging compositions comprise liposomes containing gadolinium (Gd-liposome) for early detection of plaque formation by highly concentrating the contrast agent. To establish activity, Gd-liposomes are injected into ApoE deficient mice fed a high fat diet, and the biodistribution of Gd-liposomes are determined using real time MR imaging at different time points. Alternatively, the aptamers may be coupled to liposomes containing different imaging agents such as, but not limited to fluorescent dyes, for near infrared (NIR) imaging.

Liposomes with a lipid composition of 58:40:2 (Mol %) DPPC: Cholesterol: DSPE-Methoxy PEG (2000) respectively are made by the extrusion process as follows: Briefly, the lipids are dissolved in ethanol at 55° C. The dissolved lipids are then hydrated with 300 mM ammonium sulfate solution (for 15-30 minutes) to facilitate active loading of Gd. Liposomes are extruded through a series of NUCLEPORE track-etched polycarbonate membranes of decreasing pore sizes. The liposomes are then extruded 5 times through a 0.2 µm membrane. This is followed by an extrusion through 0.1 µm membrane (5 times), then through a 0.05 µm membrane (5 times). The final extrusion is through a 0.03 µm membrane (10 times). The extrusions are carried out at 55° C. The liposomes are dialyzed overnight against 150 mM NaCl to remove unencapsulated ammonium sulfate to generate a trans-membrane proton gradient. The payload (~10 mg/ml) is added to the liposomes at 60° C. for 1 hr. The Gd:lipid ratio is 0.2:1.0 and the final lipid concentration is ~25 mM. The final encapsulated payload concentration is determined by lysis with methanol (30% of final volume) and measuring the UV absorbance at 480 nm.

To establish the biodistribution of the E-selectin targeted Gd-liposomes, ApoE deficient mice fed with high fat diet are used. The mice (n=5) are fed a high fat diet for a month prior to the imaging study. Dual-Gd liposomes are intravenously administered via the tail vein at a lipid dose of 200 mg/kg. MR studies will be performed on a 4.7T scanner (Bruker BioSpec, 47/40 USR) using a 60-mm shielded gradient insert that is capable of producing a maximum gradient amplitude of 950 mT/m with 80 µs rise time. The amount of E-selectin aptamer attached is optimized to refine the targeting of the E-selectin targeted Gd-liposomes to vulnerable plaques expressing E-selectin. The target efficiency is first characterized in vitro using a TNF treated endothelial cell line. E-selectin aptamer conjugated Gd-liposomes are intravenously injected to the ApoE mice for real time MR comparison imaging. To assess the safety of E-selectin aptamer-conjugated Gd-liposomes, treated and control animals are subjected to necropsy and histopathological tissue sections are collected and analyzed. In addition, appropriate analyses are performed for hematology and clinical chemistry on terminal blood draws from each animal.

In other embodiments, liposomes encapsulating factors which reduce the production of inflammatory cytokines by macrophage or increase lipid metabolism such as, but not limited to, peroxisome proliferator-activated receptors for use as a therapeutic for the stabilization of vulnerable plaque can be coupled to aptamers that selectively bind E-selectin, such as ESTA-1. Liposomes targeted using aptamers that selectively bind E-selectin are injected to the ApoE deficient mice once a week to establish therapeutic effect. Arteries are isolated at the end of the study and undergo careful histopathological analysis for, among other things the measurement of abundance of immune cells within intima and lipid.

E-selectin is best known to be expressed in the lumen of vascular tissue and thus in many embodiments the administration of the presently disclosed aptamers which selectively bind E-selectin, such as ESTA-1, are likely to be administered intravenously, whether intended as antagonistic ligand or to direct other therapeutic or imaging agents. However, the presently disclosed methods also include embodiments in which administration to a subject, such as human, via any suitable administration method in order to treat, prevent and/or monitor a physiological condition, such as symptoms that accompany E-selectin associated disorders.

Therapeutic or imaging agents may be administered by any number of methods known to those of ordinary skill in the art including, but not limited to, inhalation, subcutaneous (sub-q), intravenous (I.V.), intraperitoneal (I.P.), intramuscular (I.M.), or intrathecal injection, or topically applied (transderm, ointments, creams, salves, eye drops, and the like), as described in greater detail below. The particular method employed for a specific application is determined by the attending physician or veterinarian.

E-selectin expression is increased during neovascularization. Therefore, a disorder characterized by altered or unregulated angiogenesis, not only for example that accompanying oncogenic or neoplastic transformation (i.e., cancer) but also those that accompany psoriasis, rheumatoid arthritis, and ocular neovascular disorders including diabetic retinopathy and age-related macular degeneration. Therefore, in some embodiment therapies comprising the presently disclosed aptamers, which selectively bind E-selectin, such as ESTA-1 may also be applied directly to the eye (see for example, U.S. Pat. Nos. 4,131,651, 4,914,088; 5,278,151; 5,294,607 and 5,578,586 as well as US Patent Application Publication No. 20080166393). The progress of patients treated with therapies comprising the presently disclosed aptamers, which selectively bind E-selectin, such as ESTA-1, for E-selectin associated disorders of the eye can be followed using, for example, fluorescein angiography images of the eye fundus.

Pharmaceutical compositions that comprise the presently disclosed aptamers that bind E-selectin, such as ESTA-1, may be formulated in conventional manners using one or more physiologically acceptable carriers or excipients. The pharmaceutical compositions can comprise formulation materials for modifying, maintaining, or preserving, for example, the pH, osmolarity, viscosity, clarity, color, isotonicity, odor, sterility, stability, rate of dissolution or release, adsorption or penetration of the composition. Suitable formulation materials include, but are not limited to: amino acids (e.g., glycine, glutamine, asparagine, arginine and lysine); antimicrobials; antioxidants (e.g., ascorbic acid, sodium sulfite and sodium hydrogen-sulfite); buffers (e.g., borate, bicarbonate, Tris-HCl, citrates, phosphates and other organic acids); bulking agents (e.g., mannitol and glycine); chelating agents (e.g., ethylenediamine tetraacetic acid (EDTA)); complexing agents (e.g., caffeine, polyvinylpyrrolidone, beta-cyclodextrin, and hydroxypropyl-beta-cyclodextrin); fillers; monosaccharides, disaccharides, and other carbohydrates (e.g., glucose, mannose and dextrins); proteins (e.g., serum albumin, gelatin and immunoglobulins); coloring, flavoring, and diluting agents; emulsifying agents; hydrophilic polymers (e.g., polyvinylpyrrolidone); low molecular weight polypeptides; salt-forming counterions (e.g., sodium); preservatives (e.g., benzalkonium chloride, benzoic acid, salicylic acid, thimerosal, phenethyl alcohol, methylparaben, propylparaben, chlorhexidine, sorbic acid and hydrogen peroxide); solvents (e.g., glycerin, propylene glycol and polyethylene glycol); sugar alcohols (e.g., mannitol and sorbitol); suspending agents; surfactants or wetting agents (for example, pluronics, PEG, sorbitan esters, polysorbates (e.g., polysorbate 20 and polysorbate 80), triton, tromethamine, lecithin, cholesterol, and tyloxapal); stability enhancing agents (e.g., sucrose and sorbitol); tonicity enhancing agents (for example, alkali metal halides (e.g., sodium or potassium chloride), mannitol, and sorbitol); delivery vehicles; diluents; excipients; and pharmaceutical adjuvants (REMINGTON'S PHARMACEUTICAL SCIENCES, 18th Ed. (Gennaro, ed., Mack Publishing Company, Easton, Pa., 1990)). If desired, the pharmaceutical compositions to be administered may also contain minor amounts of non-toxic auxiliary substances such as wetting or emulsifying agents, pH buffering agents, and other substances such as for example, sodium acetate, and triethanolamine oleate.

Compositions that comprise one or more disclosed aptamers that bind E-selectin, such as ESTA-1, may also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein may be provided as a complex with a lipophilic compound or non-immunogenic, high molecular weight compound constructed using methods known in the art. An example of nucleic-acid associated complexes is provided in U.S. Pat. No. 6,011,020.

Compositions comprising any of the presently disclosed aptamers that bind E-selectin, such as ESTA-1, may also be coupled with soluble polymers as targetable drug carriers, in some implementations. Such polymers may include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, in some embodiments, a composition comprising a disclosed aptamer may be coupled to any polymer in a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 7500 mg/day orally. For some applications, the compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 7500 mg/day. Subcutaneous, intravenous and intraperitoneal dosages will range between 0.05 to 3800 mg/day. In some implementations, effective plasma levels of the compounds of the present invention range from 0.002 mg/mL to 50 mg/mL. Compositions comprising the presently disclosed aptamers that bind E-selectin, such as ESTA-1, may be administered in a single daily dose, or the total daily dosage may be administered in divided doses of two, three or four times daily.

For most applications, the pharmacokinetic properties for all oligonucleotide-based therapeutics, including aptamers, are tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen. Thus, the present disclosure provides materials and methods to affect the pharmacokinetics of aptamer compositions, and, in particular, the ability to tune aptamer pharmacokinetics.

The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro, 2'-O-methyl, monothiophosphate, or dithiophosphate) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in anti-neoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in U.S. Patent Application Publication No. 20060030535 entitled "Controlled Modulation of the Pharmacokinetics and Biodistribution of Aptamer Therapeutics", PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life (t½), the plasma clearance (C1), the volume of distribution (Vss), the area under the concentration-time curve (AUC), maximum observed serum or plasma concentration (Cmax), and the mean residence time (MRT) of an aptamer composition. As used herein, the term "AUC" refers to the area under the curve plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (C1) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

In some embodiments, materials and methods are provided which are designed to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. As described herein, conjugation of a modifying moiety and/or altering nucleotide(s) chemical composition alters fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This is accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, will potentially dramatically lengthen residence times of aptamers in circulation, thereby decreasing dosing frequency and enhancing effectiveness against vascular targets.

Aptamers may be conjugated to a variety of modifying moieties, such as high molecular weight polymers, e.g., PEG; peptides, e.g., Tat (a 13-amino acid fragment of the HIV Tat protein (Vives, et al., (1997), J. Biol. Chem. 272(25): 16010-7)), Ant (a 16-amino acid sequence derived from the third helix of the Drosophila antennapedia homeotic protein (Pietersz, et al., (2001), Vaccine 19(11-12): 1397-405)) and Arg7 (a short, positively charged cell-permeating peptides composed of polyarginine (Arg7) (Rothbard, et al., (2000), Nat. Med. 6(11): 1253-7; Rothbard, J et al., (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2'F and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides may also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

In addition, the compositions formulated with aptamers that selectively bind E-selectin, such as ESTA-1, may also be formulated as a depot preparation. Such long acting formulations may be administered by implantation (for example subcutaneously or intramuscularly) or by intramuscular injection. For example, compositions may be formulated with suitable polymeric or hydrophobic materials (for example as an emulsion in an acceptable oil), ion exchange resins, or as sparingly soluble derivatives, for example, as a sparingly soluble salt. The compositions may, if desired, be presented in a pack or dispenser device, which may contain one or more unit dosage forms containing the active ingredient. The pack may for example comprise metal or plastic foil, such as a blister pack. The pack or dispenser device may be accompanied by instructions for administration.

Active ingredients described herein may be administered by controlled release means or by delivery devices that are well-known to those of ordinary skill in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566. Such dosage forms may be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof, to provide the desired release profile in varying proportions. Exemplary sustained release matrices include, but are not limited to, polyesters, hydrogels, polylactides (see, e.g., U.S. Pat. No. 3,773,919 and European Patent Application Publication No. EP 058,481), copolymers of L-glutamic acid and gamma ethyl-L-glutamate (see, e.g., Sidman et al., Biopolymers 22:547-556, 1983), poly(2-hydroxyethyl-methacrylate) (see, e.g., Langer et al., J. Biomed. Mater. Res. 15:167-277, 1981, and Langer, Chemtech 12:98-105, 1982), ethylene vinyl acetate (Langer et al., supra), and poly-D(−)-3-hydroxybutyric acid (European Patent Application Publication No. EP 133,988). Sustained release compositions may include liposomes, which can be prepared by any of several methods known in the art (see, e.g., Eppstein et al., Proc. Natl. Acad. Sci. USA 82:3688-3692, 1985, and European Patent Application Publication Nos. EP 036,676, EP 088,046, and EP 143,949). Suitable controlled-release formulations known to those of ordinary skill in the art, including those described herein, can be readily selected for use with the compositions of this disclosure. Thus, some embodiments of the aptamer-containing compositions encompass single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this relatively constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In some cases, active ingredients described herein are not administered to a patient at the same time or by the same route of administration. Accordingly, in some embodiments, kits are provided that, when used by the medical practitioner, simplify the administration of appropriate amounts of active ingredients to a patient.

A typical kit comprises a single unit dosage form of one or more of the compositions described herein, or a pharmaceutically acceptable salt, prodrug, solvate, hydrate, or stereoisomer thereof, and a single unit dosage form of another agent that may be used in combination with the disclosed compositions. In various embodiments, the kits further comprise devices that are used to administer the active ingredients. Examples of such devices include, but are not limited to, syringes, drip bags, patches, and inhalers.

In various embodiments, the kits further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the formulations of the disclosure do not contain any alcohols or other co-solvents, oils or proteins.

In some embodiments the presently disclosed aptamers that selectively bind E-selectin, such as ESTA-1, may be used to target small molecules and large molecules, antibodies, nucleotide sequences (e.g., antisense, siRNA, triplex, and ribozyme molecules, and gene or regulatory sequence replacement constructs) in the treatment of E-selectin associated disorders, such as but not limited to, inflammation and cancer.

Such agents may be identified using cell-based and animal model-based assays for the identification of compositions exhibiting an ability to ameliorate the symptoms of E-selectin associated disorders. Cell-based systems used to identify compositions that may act to ameliorate E-selectin associated disorder symptoms can include, for example, recombinant or non-recombinant cells, such as cell lines that express E-selectin. Host cells (e.g., COS cells, CHO cells, fibroblasts) genetically engineered to express a functional E-selectin can also be used.

In utilizing such cell-based systems, cells may be exposed to a candidate for coupling to presently disclosed aptamers, that selectively bind E-selectin such as ESTA-1, said compound being suspected of exhibiting an ability to ameliorate the symptoms of an E-selectin associated disorder such as, but not limited to, inflammation, cardiovascular, endothelial or angiogenic disorders and cancer, at a concentration and for a time sufficient to elicit such an amelioration of the E-selectin associated symptoms in the exposed cells. After exposure, the cells are assayed to measure alterations in E-selectin expression, e.g., by assaying cell lysates for E-selectin mRNA transcripts (e.g., by Northern analysis or RT-PCR), or by assaying for the level of E-selectin protein expressed in the cell (e.g., by SDS-PAGE and Western blot or immunoprecipitation). Alternatively, in some applications, the cells are examined to determine whether one or more E-selectin associated phenotype has been altered.

In addition, animal model-based systems may be used to identify compositions capable of preventing, treating, or ameliorating symptoms associated with E-selectin associated disorders such as, inflammation cardiovascular, endothelial or angiogenic disorders and cancer which can be coupled to and delivered by presently disclosed aptamers that selectively bind E-selectin, such as ESTA-1. These animals may be transgenic, knock-out, or knock-in animals (preferably humanized knock-in animals where, for example, the endogenous animal E-selectin gene has been replaced by a human E-selectin sequence), as described herein. Such animal models may be used as test substrates for identification of drugs, pharmaceuticals, therapies, and interventions that may be effective in preventing or treating E-selectin associated disorders. For example, animal models can be exposed to a compound suspected of exhibiting an ability to treat or ameliorate E-selectin associated disorders, at a sufficient concentration and for a time sufficient to elicit such an amelioration of E-selectin associated disorders in the exposed animals. The response of the animals to the exposure may be monitored by assessing the reversal of symptoms associated with the E-selectin associated disorder. With regard to intervention, any treatments that prevent, reverse, halt, or slow the progression of any aspect of symptoms associated with E-selectin associated disorders should be considered as candidates for therapeutic intervention in the prevention or treatment of E-selectin associated disorders. Dosages of test agents may be determined by deriving toxicity and dose-response curves.

In some embodiments, one or more compositions targeted using aptamers that selectively bind E-selectin, such as ESTA-1, are administered in combination with one or more additional compounds or drugs ("additional active agents") for the treatment, management, and/or prevention of E-selectin associated disorders.

Compositions that comprise the presently disclosed aptamers that bind E-selectin, such as ESTA-1, may also be determined to reduce symptoms of E-selectin associated disorders. In some applications, such compositions are administered using the presently disclosed aptamers that selectively bind E-selectin, such as ESTA-1, to a patient at therapeutically effective doses to treat or ameliorate E-selectin associated disorders. A therapeutically effective dose refers to that amount of the composition sufficient to result in any delay in onset, amelioration, or retardation of disease symptoms.

Toxicity and therapeutic efficacy of such compositions intended for delivery using presently disclosed aptamers that selectively bind E-selectin, such as ESTA-1, can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, expressed as the ratio ED50/LD50. Compositions that exhibit large therapeutic indices are preferred. Compositions that exhibit toxic side effects may be used in certain embodiments, however, care should usually be taken to design delivery systems that target such compositions preferentially to the site of affected tissue, in order to minimize potential damage to uninfected cells and, thereby, reduce side effects.

Data obtained from cell culture assays and animal studies can be used in formulating a range of dosages for use in humans. The dosages of such compositions lie preferably within a range of circulating concentrations that include the ED50 with little or no toxicity. The dosage may vary within this range depending on the dosage form employed and the route of administration utilized. For any composition disclosed herein, the therapeutically effective dose can be estimated initially from cell culture assays. A dose may be formulated in animal models to achieve a circulating plasma concentration range that includes the IC50 (i.e., the concentration of the test composition that achieves a half-maximal inhibition of symptoms) as determined in cell culture. Such information can be used to more accurately determine useful doses in humans. Plasma levels may be measured, for example, by high performance liquid chromatography.

For applications in which the therapeutic treatment of E-selectin associated disorders is contemplated, the appropriate dosage may also be determined using animal studies to determine the maximal tolerable dose, or MTD, of a bioactive agent per kilogram weight of the test subject. In general, at least one animal species tested is mammalian. Those skilled in the art regularly use representative species to extrapolate effective doses for other species, including human, and to avoid toxicity. Before human studies of efficacy are undertaken, Phase I clinical studies help establish safe doses.

Additionally, a disclosed composition or delivery system comprising aptamers that selectively bind E-selectin, such as ESTA-1, may also include known bioactive agents. The aptamer-containing composition enhances the stability of the bioactive agent, or otherwise enhances its pharmacological properties (e.g., increase in vivo half-life, reduce toxicity, etc.).

Although the exemplary embodiments detailed below emphasize the activities of one particular thioaptamer, ESTA-1, this example represents the activity of a class of aptamers, and it is predicted that aptamers which selectively bind E-selectin will have similar activities. In addition, while several of the exemplary embodiments described herein emphasize the activity of aptamers that selectively bind E-selectin to target imaging or therapeutic agents specifically to cancer cells, it should be understood that such activity is related to the ability to target E-selectin. Accordingly, it is predicted that such methods and compositions are likewise useful for addressing any other E-selectin associated disorder. The results described herein with respect to the nude mouse models using human tumors, are believed to be representative of similar results that will be obtained with different E-selectin associated disorders of other mammals, including, but not limited to, laboratory animals, companion animals, farm animals, primates and humans.

EXAMPLES

Methods and Materials

Oligonucleotide primers were synthesized by Midland Certified Reagents (Midland, Tex.). The extracellular domain of recombinant human E-selectin (535 amino acid residues) was purchased from R&D Systems (Minneapolis, Minn.). Streptavidin-coated magnetic particles were purchased from Pure Biotech (Middlesex, N.J.). Human microvascular endothelial cells (HMVECs) were a kind gift from Dr. Rong Shao (Biomedical Research Institute, Baystate Medical Center/University of Massachusetts at Amherst, Springfield, Mass., USA). Anti-human CD31 antibody was purchased from BD Pharmingen (San Jose, Calif.). Anti-E-selectin antibody H18/7 was isolated from hybridoma purchased from ATCC (Manassas, Va.) and used as a competitor of TA binding to endothelial cells. Other anti-human E-selectin antibodies were purchased from Sigma (St. Louis, Mo.) and Innovex (Richmond, Calif.) and used for immunostaining for cultured cells and human carcinoma paraffin sections, respectively. Human carcinoma tissue array was purchased from US Biomax (Rockville, Md.).

Cell Culture

Human Microvascular Endothelial cells (HMVEC) were cultured according to the protocol described by Shao and Guo, 2004 (Shao R, Guo X (2004) Human microvascular endothelial cells immortalized with human telomerase catalytic protein: a model for the study of in vitro angiogenesis. Biochem Biophys Res Commun 321: 788-794). HMVEC were grown in endothelial basal medium-2 supplemented with 10% (v/v) Tet-approved fetal bovine serum, 100 U/ml penicillin and 10 µg/ml streptomycin, 1 µg/ml epidermal growth factor and 50 µg/ml hydrocortisone. All experiments were performed on 70-80% confluent cultures in 5% CO2 humid chambers at 37° C. The HMVECs were genetically manipulated to generate Tet-on inducible system for E-selectin expression (ES-Endo). E-selectin expression was induced with doxycycline (2000 ng/ml) for 5 hours unless specified.

Synthesis and Isolation of DNA Thioaptamer Library

The synthesis of the DNA thioaptamer (TA) combinatorial library has been described by U.S. Pat. No. 6,867,289, U.S. Publication No. US20030162190 and by King et al, 1998 (Novel combinatorial selection of phosphorothioate oligonucleotide aptamers. Biochemistry 37: 16489-16493). Briefly, a single-stranded DNA library (~1014 different sequences) with a 30-nucleotide random region (N30) flanked by 23 and 21 nucleotide primer binding regions was chemically synthesized. The library (40 nM) was PCR amplified in a reaction containing Sp dATP($\alpha$S), dCTP, dGTP and dTTP (200 µM), MgCl$_2$ (2 mM), biotinylated forward primer (5' biotin-CAGTGCT-CTAGAGGATCCGTG-AC-3') (SEQ ID NO: 59) (300 nM), reverse primer (5'-CGCTCG-GATC-GATAAGCTTCG-3') (SEQ ID NO: 60) (300 nM) and AmpliTaq DNA polymerase (0.5 U). Biotinylated double-stranded PCR products were incubated with streptavidin-coated magnetic beads for the separation of the ssDNA library.

Selection of Thioaptamers

Screening of TAs that binds to recombinant E-selectin protein was carried out using a solution-based filter binding method as described previously (U.S. Pat. No. 6,867,289, U.S. Publication No. US20030162190, King et al., 1998, ibid). Briefly, the recombinant human E-selectin protein (240 pmoles) was incubated with TA library (200 pmoles) in selection buffer (PBS with Ca$^{2+}$ and Mg$^{2+}$ and 5 mM MgCl$_2$) at room temperature for 2 hours. The reaction mixture was filtered through the nitrocellulose membrane and washed 3 times with the selection buffer to remove unbound TAs. The TA/E-selectin complex retained on the filter membrane was eluted with 8 M urea solution. The eluent was used as the template for PCR amplification and the integrity of the TAs was analyzed by 15% polyacrylamide gel electrophoresis. This selection cycle was repeated 10 times and the stringency of the selection was elevated gradually. The TA libraries obtained after rounds 5 and 10 were PCR amplified and subcloned into a plasmid vector for DNA sequencing. The selected sequences were analyzed using the ClustalW program. Cyanine 3 (Cy3)-labeled TAs were produced by PCR amplification of plasmids containing TAs as a template with 5'-terminal Cy3-labeled reverse primer.

Cell Culture

Human Microvascular Endothelial cells (HMVEC) were a kind gift from Dr. Rong Shao at the University of Massachusetts. HMVEC were cultured according to the protocol described in Shao and Guo, 2004 (Human microvascular endothelial cells immortalized with human telomerase catalytic protein: a model for the study of in vitro angiogenesis. Biochem Biophys Res Commun 321: 788-794). HMVEC were grown in endothelial basal medium-2 supplemented with 10% (v/v) Tet-approved fetal bovine serum, 100 U/ml penicillin and 10 µg/ml streptomycin, 1 µg/ml epidermal growth factor and 50 µg/ml hydrocortisone. All experiments were performed on 70-80% confluent cultures in 5% CO2 humid chambers at 37° C. The HMVECs were genetically manipulated to generate Tet-on inducible system for E-selectin expression (ES-Endo). E-selectin expression was induced with doxycycline (2000 ng/ml) for 5 hours unless specified.

TA Binding to Endothelial Cells

To examine TA binding to the ES-Endo, the cells were plated onto a plastic dish and cultured overnight to allow them to attach. After E-selectin induction with doxycycline, the cells were incubated with Cy3-labeled TAs at the indicated concentrations (0-200 nM) for 20 minutes at 37° C. The cells were washed with ice-cold PBS to remove unbound TA and subsequently fixed with 4% paraformaldehyde for 10 minutes. The nuclei were counterstained with 1.0 µg/ml Hoechst 33342 for 10 minutes. The extent of TA binding to the cells was assessed by fluorescence microscopic analysis (TE2000-E, Nikon). The relative binding affinity of TAs was determined by the amount of fluorescence detected on the cells based binding assay and the specificity was determined by the extent of doxycycline dose dependent effect seen on TA binding. For competition of TA binding to the cells, the cells were pre-incubated with 10 mg or 25 mg of anti-E-selectin antibody (H18/7) for 2 hours prior to incubation with TA. All images were acquired under the same exposure conditions for the comparison of TA binding.

TA Binding to Tumor Vasculature

Human tissues derived from epithelial ovarian cancer patients were collected from surgical cases at The University of Texas M.D. Anderson Cancer Center. Frozen tissue arrays derived from human carcinomas (breast, ovarian, and skin) and their normal counterparts were also used (US Biomax, MD). The tissue sections were fixed with ice-cold acetone, incubated with 50 nM ESTA-1 for 1 hour at RT, and then stained with primary antibody against anti-rat CD31 (1:1000). E-selectin expression was determined by immunostaining with anti-E-selectin (1:20). For in vivo experiments a total of 10 µg of chemically synthesized Cy3-labeled ESTA-1 was intravenously injected into mice bearing tumors derived from mouse breast cancer 4T1 cells. The organs and tumors were harvested 3 hours after the injection, and each organ was embedded in OCT. 8 µm frozen section was fixed with acetone and stained with Hoechst 33342 for assessment of ESTA-1 binding to the vasculature.

Electrophoresis Mobility Shift Assay

Equal amounts of ESTA-1 (4.6 pmoles) were incubated with increasing concentrations of the recombinant selectin proteins (0-19 pmoles) in a total volume of 10.5 µl of PBS supplemented with Ca2+ and Mg2+, 5 mM MgCl2, and 1% NP40 at room temperature for 45 minutes. The reaction mixtures were loaded onto 6% polyacrylamide tris borate gels and run at 100 V for 90 minutes at 4° C. The gel was stained with SYBR Gold nucleic acid staining dye and visualized using the Fluor Chem 8800 chemimager (Alpha Innotech). Protein-bound TA and unbound TA were quantified using ImageJ software. The binding curves were generated assuming a single binding site curve fits using the Graph Pad Prism software.

Cell Adhesion Assay

To determine the effect of ESTA-1 on adhesion of sLe$^x$ positive cells to endothelial cells, confluent ES-Endo were incubated with doxycycline for 5 hours followed by ESTA-1 (50 nM, 100 nM) for 20 minutes. HL-60 cells (105 cells) suspended in RPMI containing 1% FBS were added to ES-Endo and incubated at 4° C. for 30 minutes with mild agitation. The unbound cells were washed off with RPMI containing 1% FBS. The number of cells that adhered to the ES-Endo was counted on at least 3 random areas using a light microscope (final magnification 100×) and expressed as the mean of triplicate experiments.

Cell Viability

ES-Endo were cultured on a 96-well plate at 10,000 cells per well. The cells were incubated with doxycycline for 5 hours and then incubated with ESTA-1 at the indicated concentrations for 48 hours. For the measurement of cell viability, 10 µl MTT (5 mg/ml) were added to each well and incubated for 4 hours. The formazan was dissolved in 150 µl of DMSO and the absorbance at 490 nm was measured.

Statistical Analysis

All experiments were carried out in triplicates and the data were analyzed statistically to provide 80% power for a test at significance level of 0.01. We validated the normality assumption, and proceeded with a parametric test as appropriate. The Student-T test was performed to compare the cell viability among different groups. All animals were handled in strict accordance with good animal practice as defined by University of Texas Health Science Center Institutional Animal Care and Use Committee, and all animal work was approved by the committee (protocol # HSC-AWC-07-099).

Example 1

Identification of Thioaptamer (TA) Against E-Selectin

Synthesis and isolation of DNA thioaptamer library: The synthesis of the DNA thioaptamer (TA) combinatorial library was described in U.S. Pat. No. 6,867,289, U.S. Publication No. US20030162190 and in King et al, 1998 (ibid). Briefly, a single-stranded DNA library (~1014 different sequences) with a 30-nucleotide random region (N30) flanked by 23 and 21 nucleotide primer binding regions was chemically synthesized. The library (40 nM) was PCR amplified in a reaction containing Sp dATP(αS), dCTP, dGTP and dTTP (200 µM), MgCl$_2$ (2 mM), biotinylated forward primer (5'biotin-CAGT-GCTCTAGAGGATCCGTG-AC-3' (SEQ ID NO: 59) (300 nM), reverse primer (5'-CGCTCGGATCGATAAGCT-TCG-3 (SEQ ID NO: 60) (300 nM) and AmpliTaq DNA polymerase (0.5 U). Biotinylated double-stranded PCR products were incubated with streptavidin-coated magnetic beads for the separation of the ssDNA library.

Selection of thioaptamers: Screening of TAs that bind to recombinant E-selectin protein was carried out using a solution-based filter binding method as described in U.S. Pat. No. 6,867,289, U.S. Publication No. US20030162190 and by King et al, 1998 (ibid). Briefly, recombinant human E-selectin protein (240 pmoles) was incubated with TA library (200 pmoles) in selection buffer (PBS with Ca$^{2+}$ and Mg$^{2+}$ and 5 mM MgCl$_2$) at room temperature for 2 hours. The reaction mixture was filtered through the nitrocellulose membrane and washed 3 times with the selection buffer to remove unbound TAs. The TA/E-selectin complex retained on the filter membrane was eluted with 8 M urea solution. The eluent was used as the template for PCR amplification and the integrity of the TAs was analyzed by 15% polyacrylamide gel electrophoresis. This selection cycle was repeated 10 times and the stringency of the selection was elevated gradually. The TA libraries obtained after rounds 5 and 10 were PCR amplified and subcloned into a plasmid vector for DNA sequencing. Cyanine 3 (Cy3)-labeled TAs were produced by PCR amplification of plasmids containing TAs as a template with 5'-terminal Cy3-labeled reverse primer.

Screening for thioaptamer against E-selectin: A TA library was screened to select for those TAs that demonstrated affinity for E-selectin. Each of the 1014 TAs in the library consisted of a region of random sequence (N30 residues) flanked by two primer regions common to all TAs, and all dA's contained 5'-monothiophosphate substitutions with the exception of the 5' primer region. A two-step E-selectin TA selection strategy followed. First, a solution-based combinatorial selection method was employed for the identification of thioaptamers that bind the extracellular domain of recombinant human E-selectin protein. The TA library was allowed to interact in solution with glycosylated recombinant E-selectin protein. Then, the E-selectin/TA complexes formed were isolated and PCR amplified to be used in subsequent cycles of selection. After 10 iterative selection cycles with increasingly stringent condition, a total of 35 TA sequences were identified (FIG. 1) and 14 representative sequences (FIG. 2) were amplified by PCR with Cy3-labeled reverse primer in preparation for a second step of cell-based selection.

Figure 7A:
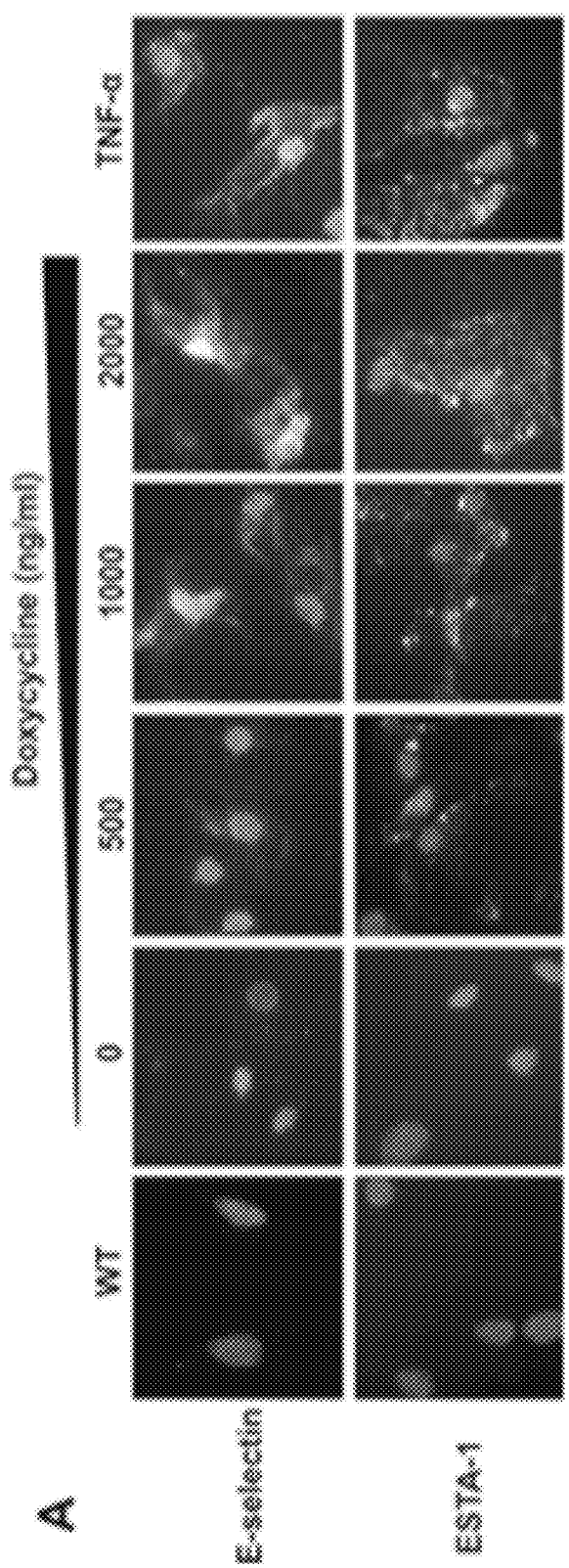
FIG. 7A illustrates E-selectin-dependent binding of ESTA-1 to ES-endothelial cells treated with increasing concentration of doxycycline.

A Tet-on inducible E-selectin endothelial cell line (ES-Endo) was used to identify the TA sequences that specifically bind to E-selectin on the surface of endothelial cells. First, to demonstrate the doxycycline-dependent induction of E-selectin expression, ES-Endo cells were incubated with increasing concentrations of doxycycline (0-2000 ng/ml) for 5 hours, and the E-selectin expression level on the plasma membrane was analyzed by immunofluorescent staining using anti-E-selectin antibody. As a reference for the physiological level of E-selectin expression, the cells were also treated with TNF-α (10 ng/ml) for 5 hours. Elevated expression of E-selectin was detected predominantly on the cell membrane when treated with 500 ng/ml of doxycycline, and its expression level was increased in a doxycycline concentration dependent manner (FIG. 7A). To determine the E-selectin-dependent ESTA binding, ES-Endo cells were treated with increasing concentration of doxycycline (250-2000 μg/ml) and analyzed for E-selectin expression and ESTA-1 binding. E-selectin overexpressing ES-Endothelial cells were incubated with Cy3 labeled ESTA 1 (100 nM) for 20 minutes at 37° C. TNF-α induced ES-Endothelial cells were used as positive control. In the absence of doxycycline, the baseline level of E-selectin expression was slightly higher than wild type cells, perhaps due to the leakiness of this inducible system. The level of E-selectin expression with a doxycycline concentration of 2000 ng/ml was equivalent to TNF-α treated cells, and thus, doxycycline was used at this concentration for subsequent experiments, unless otherwise specified. For the second-step selection of TAs that bind specifically to E-selectin, ES-Endo were pre-incubated with doxycycline and then with each of the 14 TAs (100 nM) selected in the first step for 20 minutes at 37° C. Fluorescent intensities associated with the cells were compared using fluorescent microscopy. Among the 14 TAs tested, only one thioaptamer (TA-1) exhibited high doxycycline-dependent binding to ES-Endo with minimal binding to ES-Endo cells in the absence of doxycycline. Although all of the TAs were isolated based on their ability to bind human recombinant E-selectin protein, the rest of the TAs showed either minor (TA 2-12, 14) or weak (TA13) doxycycline dependent binding with high background. Therefore, TA-1 (now referred to as E-Selectin ThioAptamer-1:ESTA-1) was selected for further characterization.

Figure 7B:
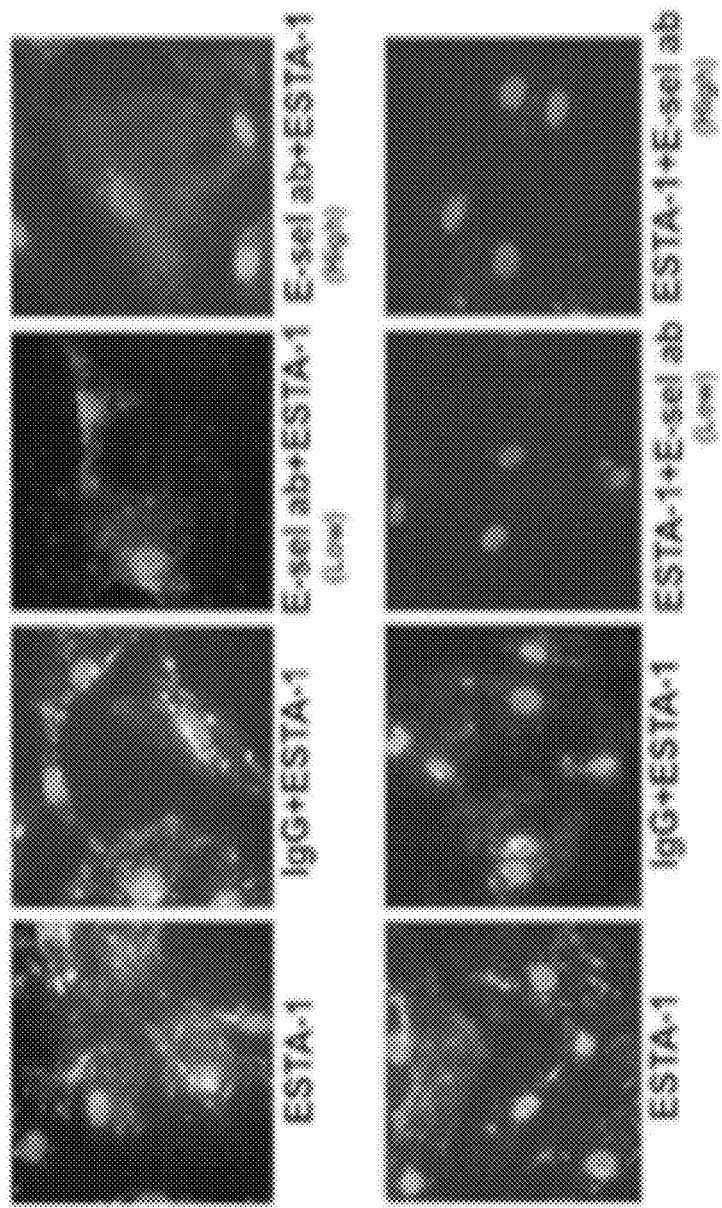
FIG. 7B illustrates the blocking of ESTA-1 binding by E-selectin antibody.
Figure 8:
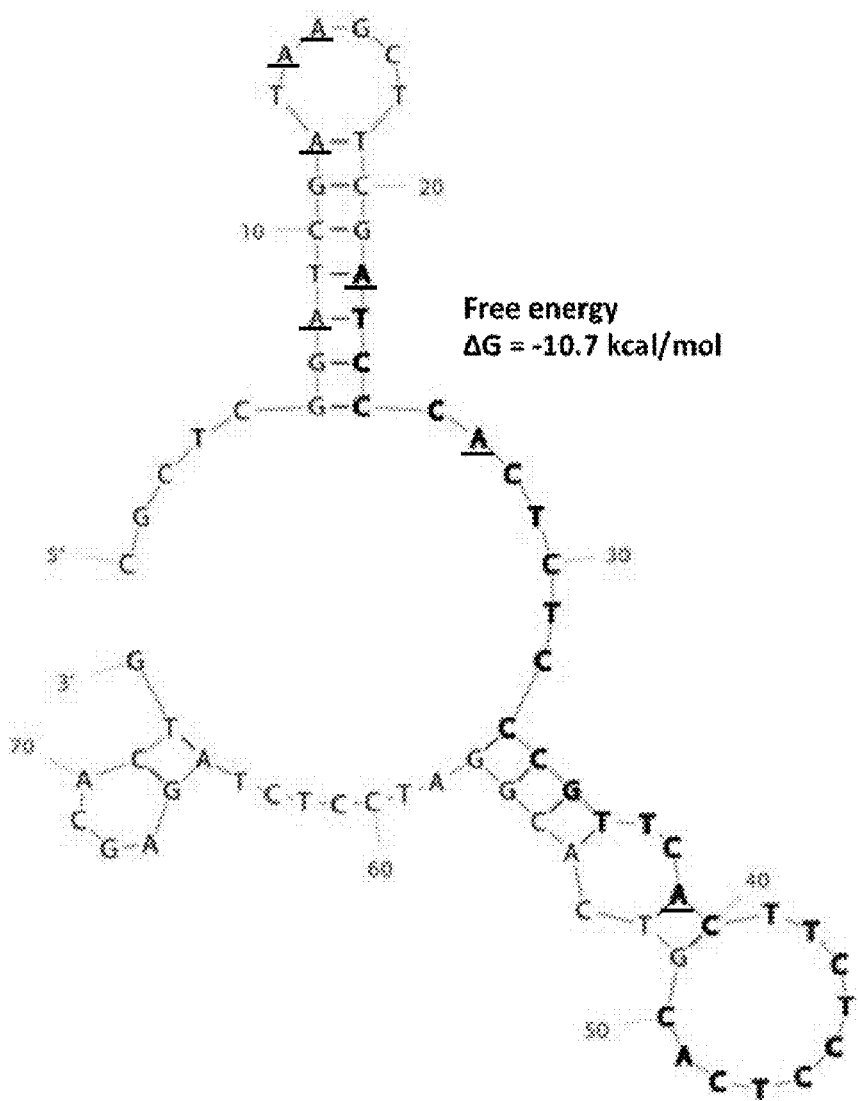
FIG. 8 illustrates ESTA-1 sequence (SEQ ID NO:1) and the M fold predicted secondary structure of ESTA-1: A. ESTA-1 DNA sequence (SEQ ID NO:1) in which all deoxy adenosine (dA) residues are modified monothio substituted with Rp configuration (indicated by underlining), with the exception of the primer binding region in the sequence.

To further demonstrate specificity of binding, ES-Endo cells expressing E-selectin were pre-treated with two different concentrations of E-selectin monoclonal antibody for 2 hours and then incubated with 100 nM of ESTA-1. More particularly, E-selectin expressing cells were pre-incubated with 25 μg of E-selectin antibody for 2 hours and incubated with 100 nM of ESTA-1 for 20 minutes. Unbound ESTA was washed away and slides were prepared for fluorescent imaging to visualize the binding to ES-Endothelial cells. All images were captured at the same exposure condition for comparison. The final images shown are representative images (at the final magnification: ×600) from five random fields of at least three independent experiments. Blue, Hoechest 33234; Red, Cy3 labeled ESTA-1; Green, E-selectin. Pre-incubation of the cells with E-selectin monoclonal antibody resulted in a significant reduction of ESTA-1 binding, as evidenced by the disappearance of the speckle pattern (FIG. 7B), indicating that ESTA-1 and monoclonal E-selectin antibody share the same epitope on E-selectin. Similar reductions in ESTA-1 binding were also observed using E-selectin antibody to pretreated TNF-α induced ES-Endo (data not shown). In contrast, the control normal IgG pre-treatment did not affect ESTA-1 binding to the cells (FIG. 7B). In conclusion, the two-step screening strategy employed here led to the identification of a TA sequence (ESTA-1) that binds specifically to E-selectin expressed on endothelial cells. The ESTA-1 sequence (FIG. 8A) does not show homology to existing genes. The secondary structure of ESTA-1 was predicted using the Mfold program (Zuker M, 2003. Mfold web server for nucleic acid folding and hybridization prediction. Nucleic Acids Res 31: 3406-3415). According to Mfold prediction, the most probable secondary structure of ESTA-1 (with an estimated free-energy change of −10.7 kcal/mol) contains two stable hairpin loops (FIG. 8B) that may account for its enhanced affinity for E-selectin.

Example 2

E-selectin Thioaptamer-1 (ESTA-1) Binds Tumor Vasculature Bearing E-selectin

Figure 9:
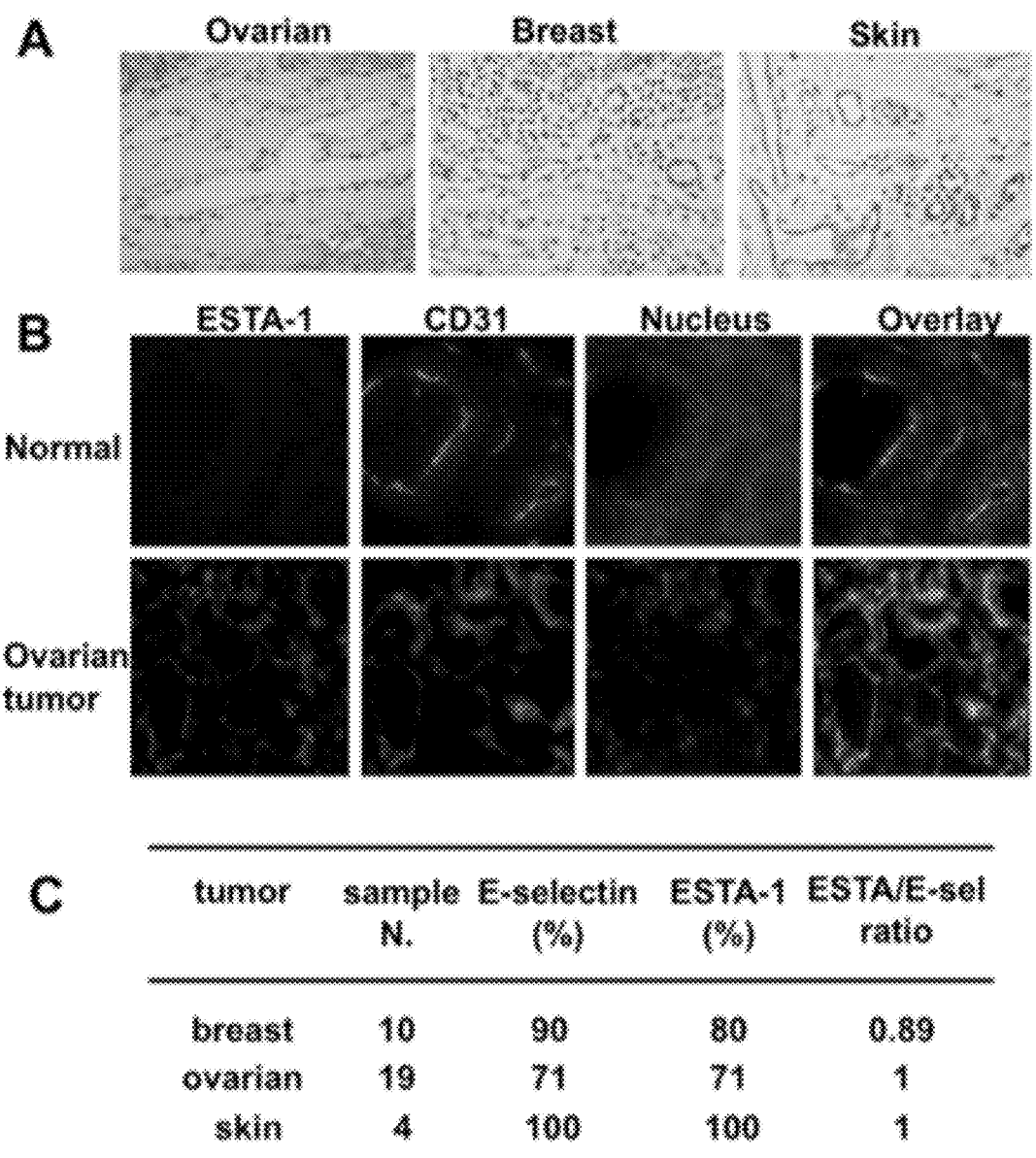
FIG. 9 illustrate ESTA binding to the tumor vasculature. A: Frozen sections derived from human ovarian carcinoma and normal human ovaries were examined for E-selectin expression and ESTA binding. Immunohistochemical analysis for E-selectin expression on the vasculature of ovarian carcinoma (arrows) is shown. B: ESTA-1 binding to the tumor vasculature of ovarian carcinoma. C: Correlation of ESTA-1 biding to the tumor vasculature and E-selectin expression (arrows) in human carcinomas derived from breast, ovary, and skin.
Figure 10:
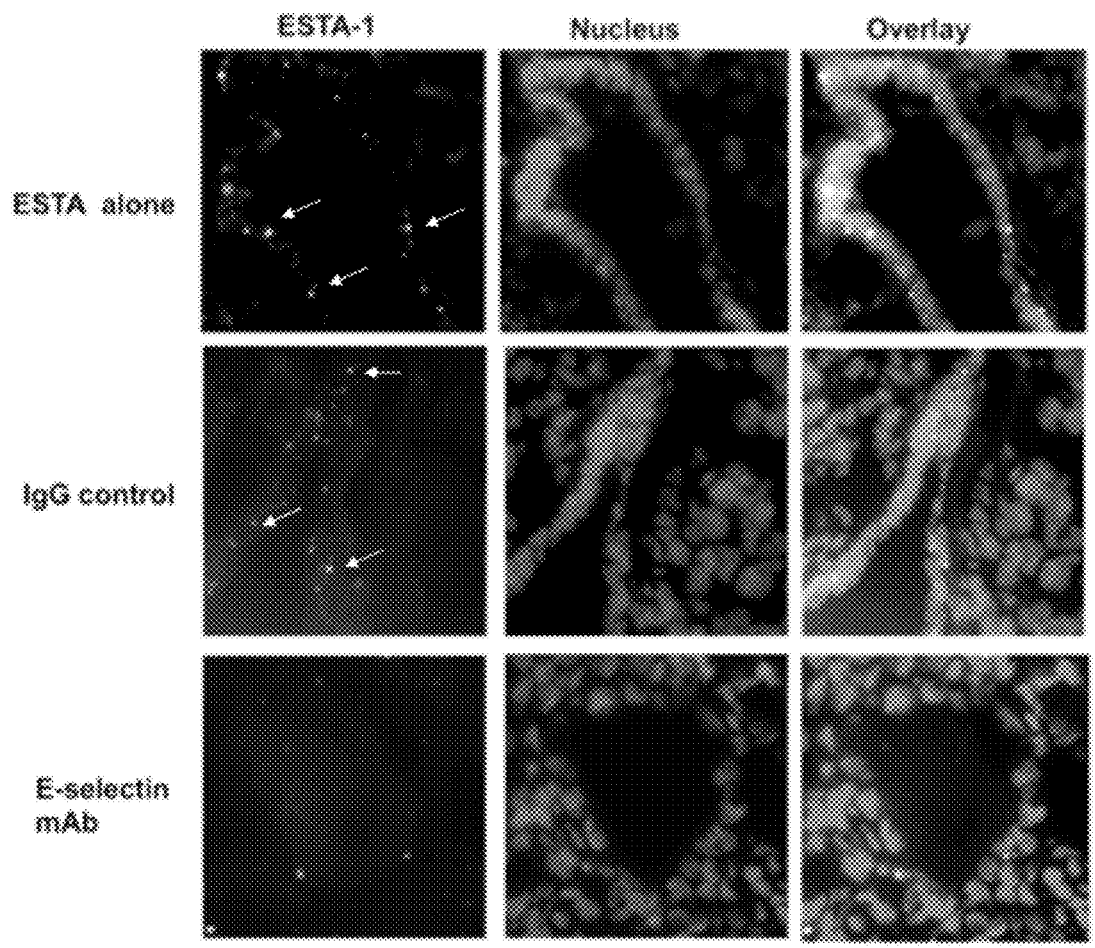
FIG. 10 illustrates the in vivo distribution of ESTA-1 in mice bearing xenograft tumor derived from breast cancer 4T1 cells.

ESTA-1 binding to the tumor vasculature was demonstrated using histological sections derived from human carcinomas. First, immunohistochemical analysis was performed to evaluate the level of E-selectin expression on the tumor vasculature using paraffin sections derived from three types of carcinomas including breast, ovarian, and skin. Green, CD31; Red, ESTA-1; Blue, Hoechst stained nucleus. At least five individual tumors were examined with five different fields per slide and representative sections were shown at the final magnification of ×200. Approximately 70-80% of tumors showed E-selectin expression on the vasculature (FIGS. 9A and C). Unlike angiogenic factors, such as integrins and vascular endothelial growth factor receptor, E-selectin expression was detected in both the existing mature vessels and the microvessels in the tumor (FIG. 9A, arrows). To characterize ESTA-1 binding to the tumor vasculature frozen sections of ovarian, breast and skin tumors were first incubated with a 50 nM solution of Cy3-labeled ESTA-1 (resulting in a red fluorescence), then immunostained with CD31 (resulting in a green fluorescence). Intense ESTA-1 binding was observed on the vessels in ovarian carcinomas as evidenced by the co-localization with CD31 (FIG. 9B, arrows). In contrast, ESTA-1 binding was not observed in the vessels in the normal counterpart. Similarly, ESTA-1 bound to the tumor associated vessels in breast (80%) and skin (100%) carcinomas (FIG. 9C). Overall, ESTA-1 binding to the tumor associated vessels was highly correlated with E-selectin expression as indicated by ESTA/E-selectin ratios for breast (ratio=0.89), ovarian (ratio=1) and skin (ratio=1) carcinomas (FIG. 9C). In contrast to the binding of ESTA-1 seen in tumor associated vessels, ESTA-1 binding was almost absent in the normal human tissues, including the adrenal, brain, temporal lobe, breast, cervix, heart, kidney, liver, lung, pancreas, placenta, salivary gland, skeletal muscle, small intestine, spleen, stomach, thyroid, and uterus, with the exception of minor binding to the vessels of the skin (data not shown), where E-selectin has been shown to be constitutively expressed (Keelan E T, et al., (1994) Characterization of E-selectin expression in vivo with use of a radiolabeled monoclonal antibody. Am J Physiol 266: H278-290). ESTA-1 binding to E-selectin on tumor-associated vasculature in vivo was demonstrated using the 4T1 breast tumor mouse model in which it has been reported that high levels E-selectin are expressed on the endothelial cells of the tumor-associated vasculature (FIG. 10). Frozen sections derived from 4T1 xenograft model were examined for E-selectin expression and ESTA-1 binding. ESTA-1 (10 µg/100 µl saline) was injected to mice via tail vein and organs, including liver, kidney, lung, heart, spleen, and tumor, were harvested 5 hours after the injection. Frozen sections (5 µm) were prepared to assess distribution of ESTA-1. Red, Cy3-labeled ESTA-1; blue, Hoechst 33342. Intravenous administration of ESTA-1 into nude mice bearing human 4T1 tumors resulted in accumulation of ESTA-1 on the endothelial cells of the tumor vasculature, as evidenced by the speckled red pattern of staining seen on the vessels (FIG. 10, arrows), no obvious binding of ESTA-1 to the vasculature of other organs (liver, spleen, kidney, lung, and heart) was detected. The same patterns were seen in tissues from mice that had been pre-treated with anti-E selectin monoclonal antibody but not mice that had been pre-treated with unrelated control monoclonal antibodies.

Example 3

E-selectin Thioaptamer-1 (ESTA-1) Binding Affinity to E-selectin

Figure 11:
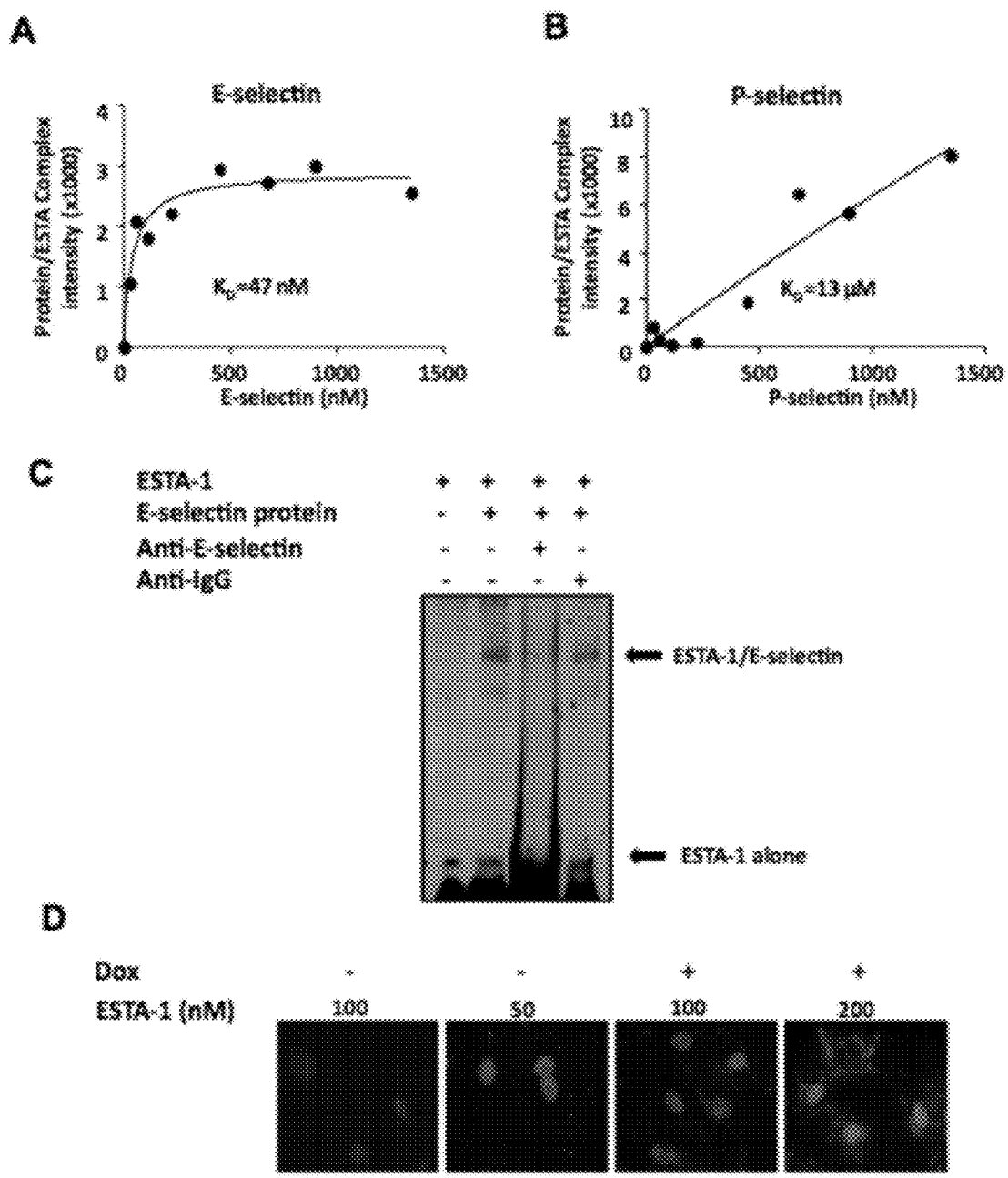
FIG. 11 illustrates the evaluation of binding affinity of ESTA-1 to E-selectin. A: Demonstrates binding affinity of ESTA-1 to E-selectin recombinant protein. B: Demonstrates binding affinity of ESTA-1 to P-selectin recombinant protein. C: Demonstrates binding affinity of ESTA-1 concentration dependent binding to ES-Endo. D: Demonstrates binding affinity of ESTA-1 to ES-Endo cells that were incubated with doxycycline (1000 ng/ml) for 5 hours and then with indicated concentrations of ESTA-1 for 20 minutes. ESTA-1 binding was analyzed by fluorescent imaging.

To evaluate the binding affinity of ESTA-1 to all selectins, an electrophoretic mobility shift assay (EMSA) was utilized. To determine the binding constant, fixed amounts of ESTA-1 was mixed with increasing amounts of recombinant protein (E-, P-, and L-selectin). ESTA-1 (4.6 pmoles) and recombinant human selectin protein (up to 19 pmoles) were incubated and subjected to electrophoresis at 4° C. The gels were stained with SYBR Gold nucleic acid stain and densitometric analysis of the unbound ESTA-1 was plotted using E-selectin or P-selectin recombinant protein. Incubation of recombinant E-selectin protein and ESTA-1 resulted in the formation of a DNA/protein complex in equilibrium with unbound states. An increment in ESTA-1/E-selectin complexes was observed with increasing recombinant E-selectin added to the reaction, accompanied by a corresponding decrease in the free (unbound) ESTA-1. As expected, the amounts of ESTA-1/E-selectin complexes reached saturation at a molar ratio of 1:1, when both of the binding molecules are at a concentration of 500 nM. Based on the densitometric analysis, the binding constant calculated for the ESTA-1 binding to E-selectin was 47 nM (FIG. 11A). The binding of ESTA-1 to P-selectin showed significantly lower affinity (estimated KD=13 µM), suggesting a very weak interaction at the concentration range measured (FIG. 11B). ESTA-1 binding to L-selectin was not detectable under the same conditions. These data demonstrate that ESTA-1 selectively binds predominantly to E-selectin with nanomolar affinity. To further validate the binding affinity of ESTA-1 under biological conditions, different concentrations of ESTA-1 (50-200 nM) were incubated with ES-Endo cells induced with doxycycline. ESTA-1 binding to the cells was detectable at 50 nM and increased in a dose dependent manner (FIG. 11C). FIG. 11D illustrates the evaluation of binding affinity of ESTA-1 to ES-Endo cells that were incubated with doxycycline (1000 ng/ml) for 5 hours and then with indicated concentrations of ESTA-1 for 20 minutes. ESTA-1 binding was analyzed by fluorescent imaging. Together, these data support a nanomolar affinity of ESTA-1 binding to E-selectin on the endothelial cells.

Example 4

Figure 12:
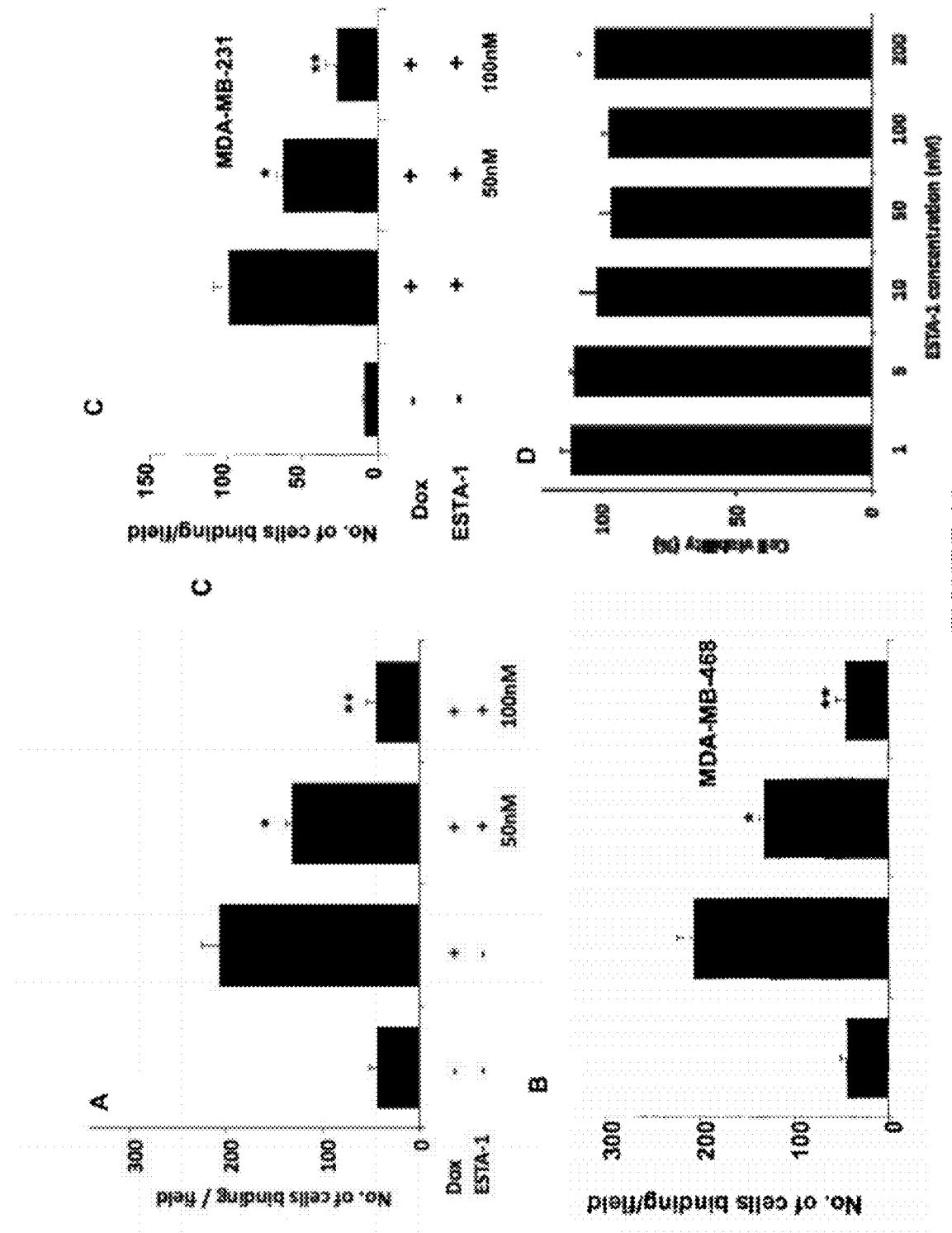
FIG. 12 illustrates the effect of ESTA-1 binding on cell adhesion to endothelial cells. ES-Endo cells were incubated with doxycycline (1000 μg/ml) for 5 hours followed by ESTA-1 (50 nM) for 30 minutes. sLe$^x$ positive HL-60 cells (A), MDA-MB-231 (B), and MDA-MB-468 (C) were added to each well and incubated at 4° C. for 30 minutes. After brief wash, the cells that adhere on the endothelial cells were counted in five fields under 100× magnification and summarized. (D) The effect of ESTA-1 on endothelial cell viability in an MTT assay. Incubation with up to 200 nM of ESTA-1 for 48 hours did not cause any visible morphological changes or a reduction of cell viability in ES-Endo cells. Doxycycline induced cells not incubated with ESTA-1 were used for normalization. Data was summarized from triplicated experiments.

Aptamers that Selectively Bind E-selectin Inhibit sLe$^X$ Positive Cell Binding to Endothelial Cells On the basis of specific binding of ESTA-1 to E-selectin, a study was done to determine the effect of ESTA-1 on adhesion of sLe$^X$ positive cells to endothelial cells. Confluent E-selectin expressing ES-Endo cells were incubated with doxycycline for 5 hours followed by ESTA-1 (50 nM, 100 nM) for 20 minutes. HL-60 cells a human promyelomonocytic cell line, or cells from two breast cancer cell lines (MDA-MB-231 and MDA-MB-468: 105 cells) suspended in RPMI containing 1% FBS were added to ES-Endo and incubated at 4° C. for 30 minutes with mild agitation. The unbound cells were washed off with RPMI containing 1% FBS. The number of cells that adhered to the ES-Endo was counted on at least 3 random areas using a light microscope (final magnification 100×) and expressed as the mean of triplicate experiments. To demonstrate blocking by ESTA-1, ES-Endo cells were pre-incubated with indicated concentrations of ESTA-1 for 20 minutes and then the adhesion of these cancer cells to the ES-Endo was compared. HL-60 cell adhesion to ES-Endo increased by 5-fold when E-selectin expression was induced by doxycycline (FIG. 12A). Pretreatment of the E-selectin expressing ES-Endo with ESTA-1 inhibited HL-60 adhesion by 80% at 100 nM ESTA-1 (FIG. 12A). The IC50 for the inhibition of this interaction was approximately 63 nM. Similarly, pre-incubation of ESTA-1 (100 nM) inhibited the adhesion of sLe$^X$ positive metastatic breast cancer cells by 75% (MDA-MB-231 and MDA-MB-468) to E-selectin expressing ES-endo cells (FIGS. 12B and C). These data indicate that the ESTA-1 interaction to E-selectin occur through the sLe$^X$ binding site, further highlighting therapeutic value of ESTA-1 as an antagonist of E-selectin mediated adhesion. Lastly, we tested cytotoxicity associated with ESTA-1 treatment in ES-Endo cells. ES-Endo cells were first incubated with doxycycline for 5 hours and then with increasing concentration of ESTA-1 (up to 200 nM) for 48 hours. MTT assay was performed to test cell viability. Incubation with ESTA-1 did not cause any visible morphological changes or a reduction of cell viability at least up to 200 nM of ESTA-1 for 48 hours (FIG. 12D).

Example 5

ESTA-1 Inhibition of Tumor Growth in an In Vivo Breast Cancer Model

Figure 13:
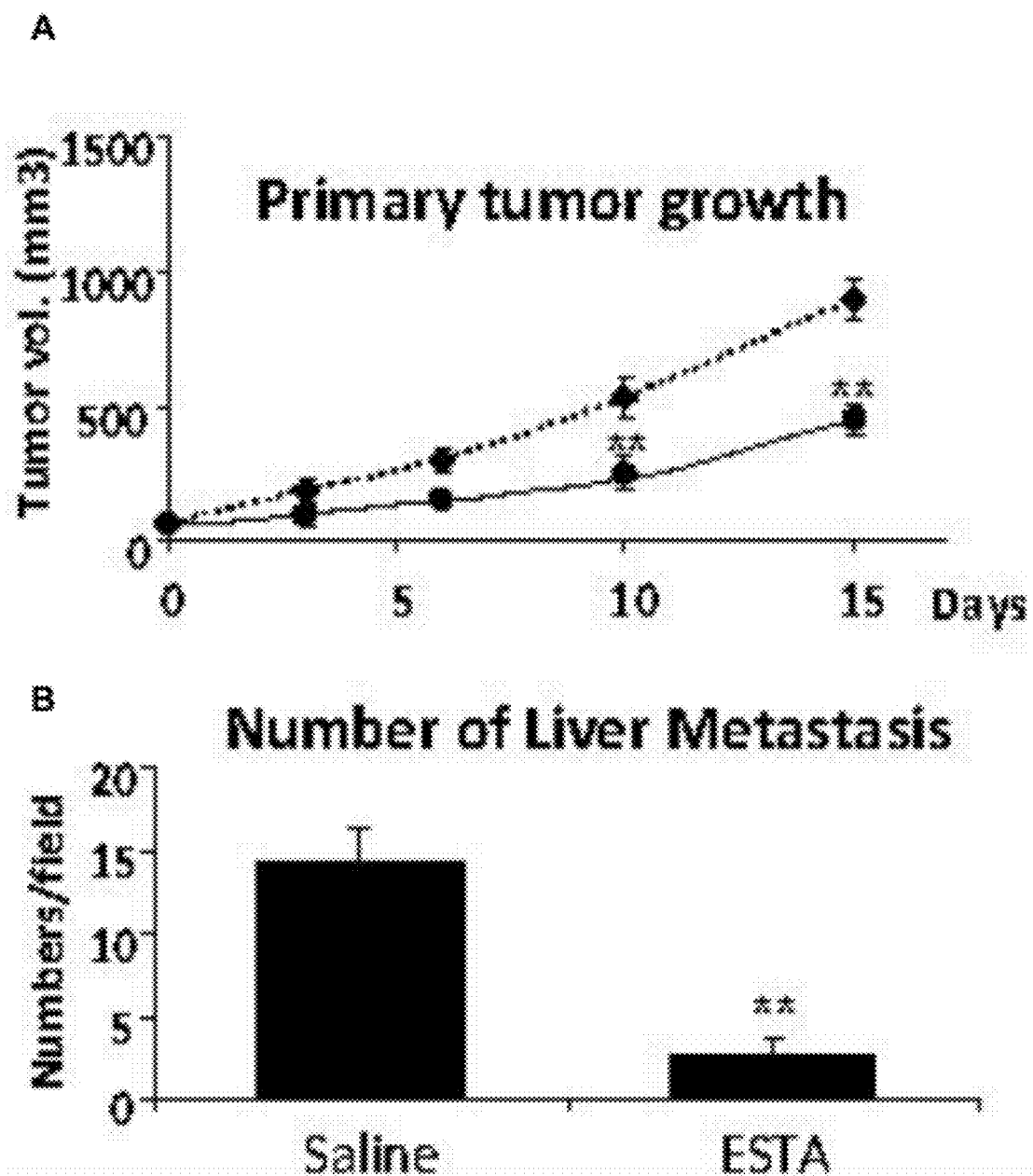
FIG. 13 illustrates the evaluation of anti-tumor effect of ESTA-1 in mouse model of breast tumor. A: Primary tumor growth. Solid line=ESTA-1 treated; broken line=saline treated controls. B: Demonstrates the reduction in the number of metastatic foci in the liver of mice treated with ESTA-1 as compared to saline treated control mice.

Since ESTA-1 demonstrated highly selective binding of E-selectin on tumor vasculature as well as a selective antagonistic effect, the anti-tumor effect of ESTA-1 in vivo was also evaluated. Mice (n=6) bearing breast tumors derived from 4T1 breast carcinoma cells were treated with ESTA-1 for 2 weeks (50 µg/day). The dose and dose rate were determined based on in vitro serum stability of ESTA-1 and safe oligonucleotide dosage for intravenous injection as reported previously (Reyderman L, Stavchansky S. Pharmacokinetics and biodistribution of a nucleotide-based thrombin inhibitor in rats. *Pharm Res*. 1998 June; 15 (6): 904-10; Tucker C E, Chen L S, Judkins M B, Farmer J A, Gill S C, Drolet D W. Detection and plasma pharmacokinetics of an anti-vascular endothelial growth factor oligonucleotide-aptamer (NX1838) in rhesus monkeys. *J Chromatogr B Biomed Sci Appl.* 1999 Sep. 10; 732(1):203-12; Hicke B J, Stephens A W, Gould T, Chang Y F, Lynott C K, Heil J, et al. Tumor targeting by an aptamer. *J Nucl Med.* 2006 April; 47(4):668-78). Control mice were injected with equal volumes of saline. Daily treatment with ESTA-1 reduced tumor growth by approximately 50% (p<0.01) compared to that in control animals (FIG. 13A). Furthermore, ESTA-1 inhibited the number of spontaneous liver metastases by 80% (p<0.01), thus providing evidence that ESTA-1 inhibits primary tumor and metastasis and acts as a cancer therapy (FIG. 13B).

Example 6

Biological Effects of ESTA-1 Treatment in Tumor-Bearing Mice

Figure 14:
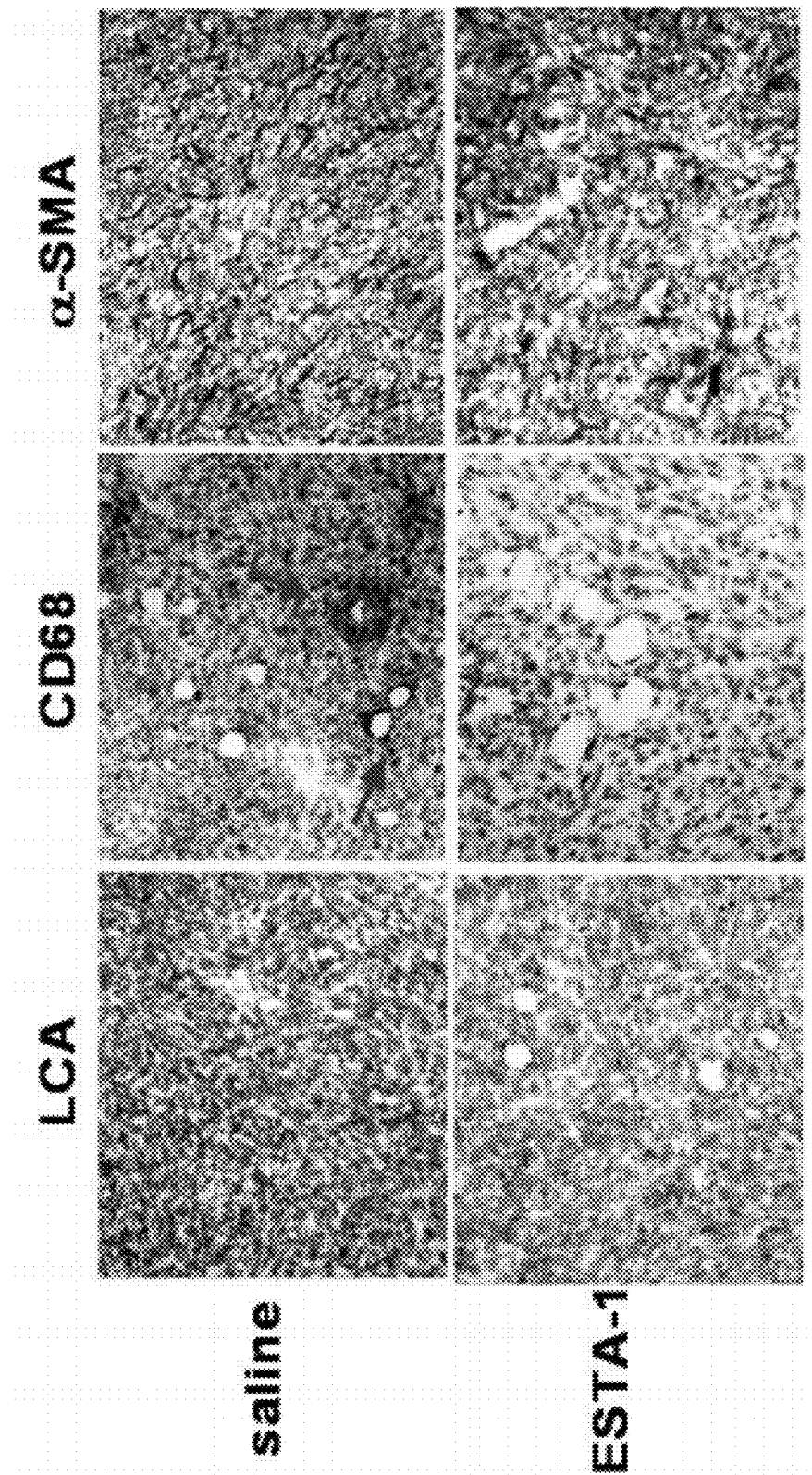
FIG. 14 shows histopathologic analysis of the primary breast tumors revealed that the ESTA-1 significantly reduced leukocyte and macrophage infiltration, as assessed by staining with common leukocyte antigen (LCA) and CD68, respectively.

Histopathological analysis of the primary tumors treated with ESTA-1 was done to characterize the biological effect of ESTA-1 mediated inhibition of tumor growth. This revealed that the ESTA-1 significantly reduced leukocyte and macrophage infiltration, as assessed by staining with common leukocyte antigen (LCA) and CD68, respectively. Infiltration of tumor-associated macrophages to the tumor periphery around the vessels was significantly reduced by ESTA-1 therapy compared to that in control treated animals (FIG. 14, see arrow). Carcinoma-associated fibroblasts (CAFs) were interrogated using an antibody against α-smooth muscle actin (α-SMA). As anticipated, CAF levels were significantly reduced by ESTA-1 treatment. These tumor stroma cells are known producers of soluble pro-tumor factors such as but not limited to, VEGF, MMPs, TGF-β, ECM proteins, and cytokines, thus treatment with ESTA-1 acts as an anti-tumor agent that inhibits leukocyte infiltration and may also attenuate angiogenesis, proliferation, leukocyte recruitment and invasive properties of tumors.

Example 7

ESTA-1 Serum Stability

To test, among other things, whether thioation of ESTA-1 DNA sequence would affect the stability of the aptamer and resistance to nuclease activity present in serum. Monothioated ESTA-1 was incubated in freshly prepared mouse serum at 37° C. and it was observed that non-thioated ESTA was degraded completely within 1 hr. In contrast, mono-thioated ESTA-1 was more stable and the estimated half life of ESTA-1 in the serum of 24 hours. This provided further evidence that thioation of DNA backbone results in an enhancement of stability in the serum. On the basis of given half life of monothioated ESTA-1 in the serum, ESTA-1 was intravenously administered daily for therapy as described in Example 5. However, it is possible that half life of ESTA-1 in vivo may be shorter due to immune cell uptake and renal clearance. Therefore, for some applications, ESTA-1 may be dithioated to improve the pharmacokinetics.

Example 8

Vascular Imaging Using Dual-Gd Liposomes

Liposomal-based gadolinium (Gd) nanoparticles (Dual-Gd liposomes with Gd-DTPA encapsulated inside, and conjugated outside liposomes) which have the high molar relaxivity were prepared as described (see for example, Ghaghada K B, et al., New dual mode gadolinium nanoparticle contrast agent for magnetic resonance imaging. *PLoS One.* 2009 Oct. 29; 4(10):e7628; Sakamoto J, et al., Antibiological barrier nanovector technology for cancer applications. *Expert Opin Drug Deliv.* 2007 July; 4(4):359-69; Saul J M, et al., Controlled targeting of liposomal doxorubicin via the folate receptor in vitro. *J Control Release.* 2003 Sep. 19; 92(1-2): 49-67; U.S. Pat. No. 7,713,517 and US Patent Application Publication Nos. 20050238584, 20070212303, 20080131369 and 20090263326). A lipid mixture consisting of DPPC, Gd-DTPA-BSA, Cholesterol and mPEG2000-DSPE in the ratio 32:25:40:3 was dissolved in a chloroform: methanol mixture. The solvent mixture was evaporated to dryness under vacuum and the lipid contents were hydrated with a solution of gadobendate meglumine (Multihance®, 500 mM Gd) to achieve a lipid concentration of 40 mM. The solution was stirred for 90 minutes at 60° C. and then sequentially extruded five passes through 400 nm Nuclepore membrane, seven passes through 200 nm Nuclepore membrane and ten passes through 100 nm Nuclepore membrane. The resulting solution was diafiltered using a MicroKros® module (Spectrum Laboratories, CA) of 500 kDa molecular weight cut-off to remove unencapsulated Gd-chelate molecules.

Figure 15:
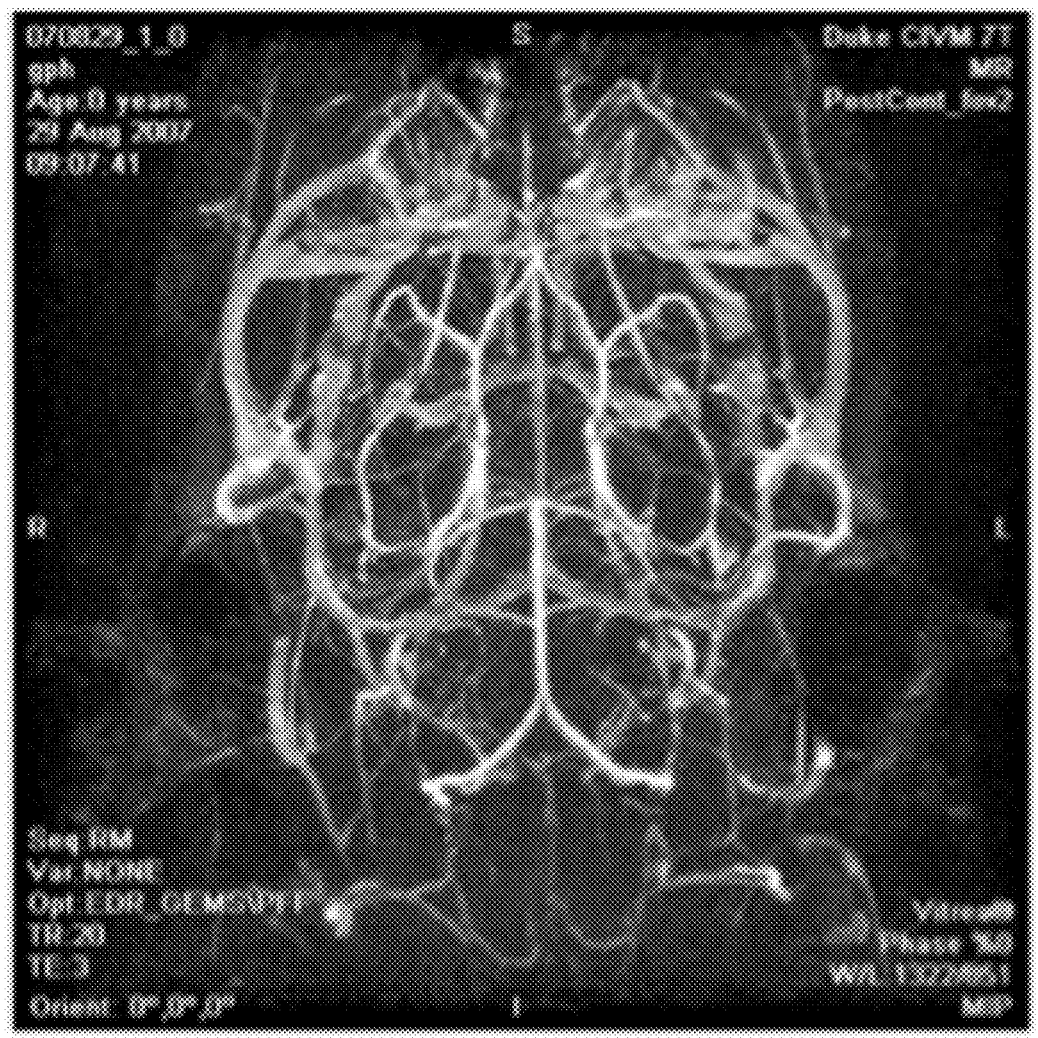
FIG. 15 illustrates the imaging capability of liposomal-based gadolinium (Gd) nanoparticles, showing typical cranial vasculature images acquired from such a scan in a mouse.

Dual-Gd Liposomes were intravenously administered via the tail vein at a lipid dose of 200 mg/kg to C57BL6/J mice. MR studies were performed on a 4.7T scanner (Bruker BioSpec, 47/40 USR) using a 60-mm shielded gradient insert that is capable of producing a maximum gradient amplitude of 950 mT/m with 80 µs rise time. Standard resolution scans were acquired using the following parameters: repetition time (TR)=5.0 ms; echo time (TE)=2.2 ms; flip angle (FA)=30°; field of view (FOV)=30×30×30 mm3; Image matrix=128× 128×128; number of signal averages=1. This resulted in an isotropic voxel size of 234 µm. The total scan time was one minute. High-resolution scans were acquired with same parameters as above. However the images matrix was 256× 256×256, resulting in an isotropic voxel size of 117 µm. The total scan time was 6 minutes. FIG. 15 shows typical cranial vasculature images acquired from such a scan. Clearly, vessels up to and beyond the 4th generation of bifurcation past the carotid bifurcation are visible. ESTA-coupled Dual-Gd Liposomes applied intravenously would therefore be anticipated to target ESTA bearing tissue and could be used for imaging or the delivery of therapeutics.

Example 9

Aptamer Coupling to Nanoliposomes

ESTA-1 conjugated liposome (ESTA-lip) were developed for effective vasculature targeting. The efficiency of conjugation was evaluated by coupling Cy3 labeled carboxylated ESTA-1 (COOH-Cy3-ESTA) on amino PEGylated stealth liposome (NH$_2$-PEG-lip) and the intensity of red fluorescence was measured at an excitation/emission of 544/594 nm using a fluorimeter. A linear standard curve was generated from Cy3-labeled ESTA-1. Roughly 50% of the surface amino groups present on the liposome were conjugated to the ESTA-1 (~485 ESTA-1 molecules conjugated to one liposome). The physico-chemical properties of the liposomes were analyzed by a zeta-sizer and Fourier transform infrared spectroscopy (FTIR).

The size and zeta potential of the ESTA-1 conjugated liposome were measured using a Multisizer (Beckman) and Zeta- Pals instrument (Brookhaven Instruments). 2 μl of liposomes were added to 1.4 mL of 10 mM phosphate buffer (pH 7.3) and the analysis was conducted at room temperature (23° C.) in triplicates. To quantify the concentration of the ESTA-1 on the liposomes, Cy3 fluorescence from ESTA-lip was measured and compared with ESTA-1 standard curve. Fourier transform infrared spectroscopy (FTIR) was preformed to assess the attachment of ESTA-1 on the liposomes. Samples were diluted in de-ionized water and FTIR was performed on a NICOLET 6700 (Thermo Scientific, Waltham, Mass.). A 2 μL drop from each sample was placed on the diamond crystal and subjected to vacuum. Using a smart diamond crystal attenuated total reflection (ATR) accessory each sample was run for 150 scans at a resolution of 4 wave numbers.

Amino-terminal PEG liposomes were covalently conjugated with carboxyl ESTA-1 using the reaction described. The surface charge of the liposome changed from +4 meV to −4 meV after conjugation with ESTA-1 (see for example, Ghaghada K B, et al., New dual mode gadolinium nanoparticle contrast agent for magnetic resonance imaging. *PLoS One.* 2009 Oct. 29; 4(10): e7628; Sakamoto J, et al., Antibiological barrier nanovector technology for cancer applications. *Expert Opin Drug Deliv.* 2007 July; 4(4):359-69; Saul J M, et al., Controlled targeting of liposomal doxorubicin via the folate receptor in vitro. *J Control Release.* 2003 Sep. 19; 92(1-2):49-67; U.S. Pat. No. 7,713,517 and US Patent Application Publication Nos. 20050238584, 20070212303, 20080131369 and 20090263326).

Amine modified liposomes were used for covalent coupling of Cy3 labeled carboxyl-ESTA-1 (3' terminus) by activating the carboxyl groups with water-soluble carbodiimide. The carbodiimide reacts with the carboxyl group to create an active ester that reacts with the primary amines on the particles. This active ester intermediate can be stabilized by the addition of sulfo-NHS. To carry out coupling of labeled or unlabeled ESTA-1 a PolyLink Protein Coupling Kit (Bangs Laboratories, Inc., Fishers, Ind., USA) was used. The $NH_2$-modified liposomes, PolyLink Coupling Buffer (50 mM MES, pH 5.2; 0.05% Proclin® 300) and PolyLink Wash/Storage Buffer (10 mM Tris, pH 8.0; 0.05% Bovine Serum Albumin; 0.05% Proclin 300) were warmed to room temperature. 0.5 ml of 50 μM cy3 labeled ESTA was incubated in 150 μL of PolyLink Coupling Buffer. Immediately prior to use a 200 mg/mL PolyLink EDAC (Carbodiimide) solution was prepared by dissolving 10 mg PolyLink EDAC in 504, PolyLink Coupling Buffer. 20 μL of this EDAC solution was added to the ESTA-1 solution and mixed end-over-end. 20 μL of sulfo-NHS (200 mg/mL Pierce biotechnology) was also added to the reaction and the solution was incubated for 30 minutes at room temperature.

One (1) ml of liposomes (50 mM lipid concentration) were mixed in 2 ml PolyLink Coupling Buffer and added to the ESTA-1 solution and incubated in dark for 4 hours at room temperature with gentle mixing. The mixture was then dialyzed with PBS at 4° C. for overnight using a membrane with a molecular weight cutoff of 300,000. The solution was concentrated using an AMICON centrifugal filter device by centrifugation at 2000×G. The surface charge of the liposome changed from +4 meV to −4 meV after conjugation with ESTA-1 and the conjugation was also confirmed by analyzing the FTIR spectra.

The size of $NH_2$-PEG-lip was 110.2 nm in average, and ESTA conjugation caused a slight increase of size of the liposomes (119.3 nm). The analysis of zeta-potential showed that ESTA-1 conjugation resulted in a substantial change of the surface charge of the $NH_2$-PEG lip from +6 mV to −5 mV. This indicated that the positive charge of the amino groups on the liposome surface was substituted by the negatively charged ESTA-1. Additionally, the spectra acquired from FTIR analysis of the Cy3-ESTAlip were compared to the $NH_2$-PEG-lip and ESTA-1 alone. A reduction in peaks corresponding to C=O stretch (1650 $cm^{-1}$), and C—O stretch (1230 $cm^{-1}$) as compared to the nonreactive peak corresponding to P=O bending (1040 $cm^{-1}$) was observed in ESTA-lip. The O—H bend in the COOH-ESTA (1480 $cm^{-1}$) appeared slightly shifted and partially reactive due to the contribution of O—H from water. Taken together, these data demonstrated the successful conjugation of COOH-Cy3-ESTA-1 to the $NH_2$-PEG-lip.

Amino-terminal PEG liposomes were covalently conjugated with carboxyl ESTA-1 using the reaction described. The surface charge of the liposome changed from +4 meV to −4 meV after conjugation with ESTA-1 (see for example, Ghaghada K B, et al., New dual mode gadolinium nanoparticle contrast agent for magnetic resonance imaging. *PLoS One.* 2009 Oct. 29; 4(10): e7628; Sakamoto J, et al., Antibiological barrier nanovector technology for cancer applications. *Expert Opin Drug Deliv.* 2007 July; 4(4):359-69; Saul J M, et al., Controlled targeting of liposomal doxorubicin via the folate receptor in vitro. *J Control Release.* 2003 Sep. 19; 92(1-2):49-67; U.S. Pat. No. 7,713,517 and US Patent Application Publication Nos. 20050238584, 20070212303, 20080131369 and 20090263326).

Amine modified liposomes were used for covalent coupling of Cy3 labeled carboxyl-ESTA-1 (3' terminus) by activating the carboxyl groups with water-soluble carbodiimide. The carbodiimide reacts with the carboxyl group to create an active ester that reacts with the primary amines on the particles. This active ester intermediate can be stabilized by the addition of sulfo-NHS. To carry out coupling of labeled or unlabeled ESTA-1 a PolyLink Protein Coupling Kit (Bangs Laboratories, Inc., Fishers, Ind., USA) was used. The $NH_2$-modified liposomes, PolyLink Coupling Buffer (50 mM MES, pH 5.2; 0.05% Proclin® 300) and PolyLink Wash/Storage Buffer (10 mM Tris, pH 8.0; 0.05% Bovine Serum Albumin; 0.05% Proclin 300) were warmed to room temperature. 0.5 ml of 50 μM cy3 labeled ESTA was incubated in 150 μL of PolyLink Coupling Buffer. Immediately prior to use a 200 mg/mL PolyLink EDAC (Carbodiimide) solution was prepared by dissolving 10 mg PolyLink EDAC in 50 μL PolyLink Coupling Buffer. 20 μL of this EDAC solution was added to the ESTA-1 solution and mixed end-over-end. 20 μL of sulfo-NHS (200 mg/mL Pierce biotechnology) was also added to the reaction and the solution was incubated for 30 minutes at room temperature.

One (1) ml of liposomes (50 mM lipid concentration) were mixed in 2 ml PolyLink Coupling Buffer and added to the ESTA-1 solution and incubated in dark for 4 hours at room temperature with gentle mixing. The mixture was then dialyzed with PBS at 4° C. for overnight using a membrane with a molecular weight cutoff of 300,000. The solution was concentrated using an AMICON centrifugal filter device by centrifugation at 2000×G. The surface charge of the liposome changed from +4 meV to −4 meV after conjugation with ESTA-1 and the conjugation was also confirmed by analyzing the FTIR spectra.

Example 10

Aptamer Targeted Liposome Nanoparticle Delivery

Amino-terminal PEG liposomes were covalently conjugated with carboxyl ESTA-1 using EDC reaction. The surface charge of the liposome changed from +4 meV to −4 meV after conjugation with ESTA-1 (see for example, Ghaghada K B, et al., New dual mode gadolinium nanoparticle contrast agent for magnetic resonance imaging. *PLoS One.* 2009 Oct. 29; 4(10):e7628; Sakamoto J, et al., Antibiological barrier nanovector technology for cancer applications. *Expert Opin Drug Deliv.* 2007 July; 4(4):359-69; Saul J M, et al., Controlled targeting of liposomal doxorubicin via the folate receptor in vitro. *J Control Release.* 2003 Sep. 19; 92(1-2): 49-67; U.S. Pat. No. 7,713,517 and US Patent Application Publication Nos. 20050238584, 20070212303, 20080131369, 20090263326).

To validate the targeting efficacy of ESTA-lip in vitro, HUVEC were stimulated with TNF-α to induce E-selectin expression on the cell membrane. The TNF-α treated cells were used to test the ability of the Cy3-ESTA-lip-FITC (Cy3-ESTA-1 conjugated liposome containing FITC) to bind to E-selectin on the HUVEC cell surface. HUVEC was first stimulated with TNF-α (1000 ng/ml) for 2-4 hours to induce E-selectin expression on the endothelial cell surface.

Figure 16:
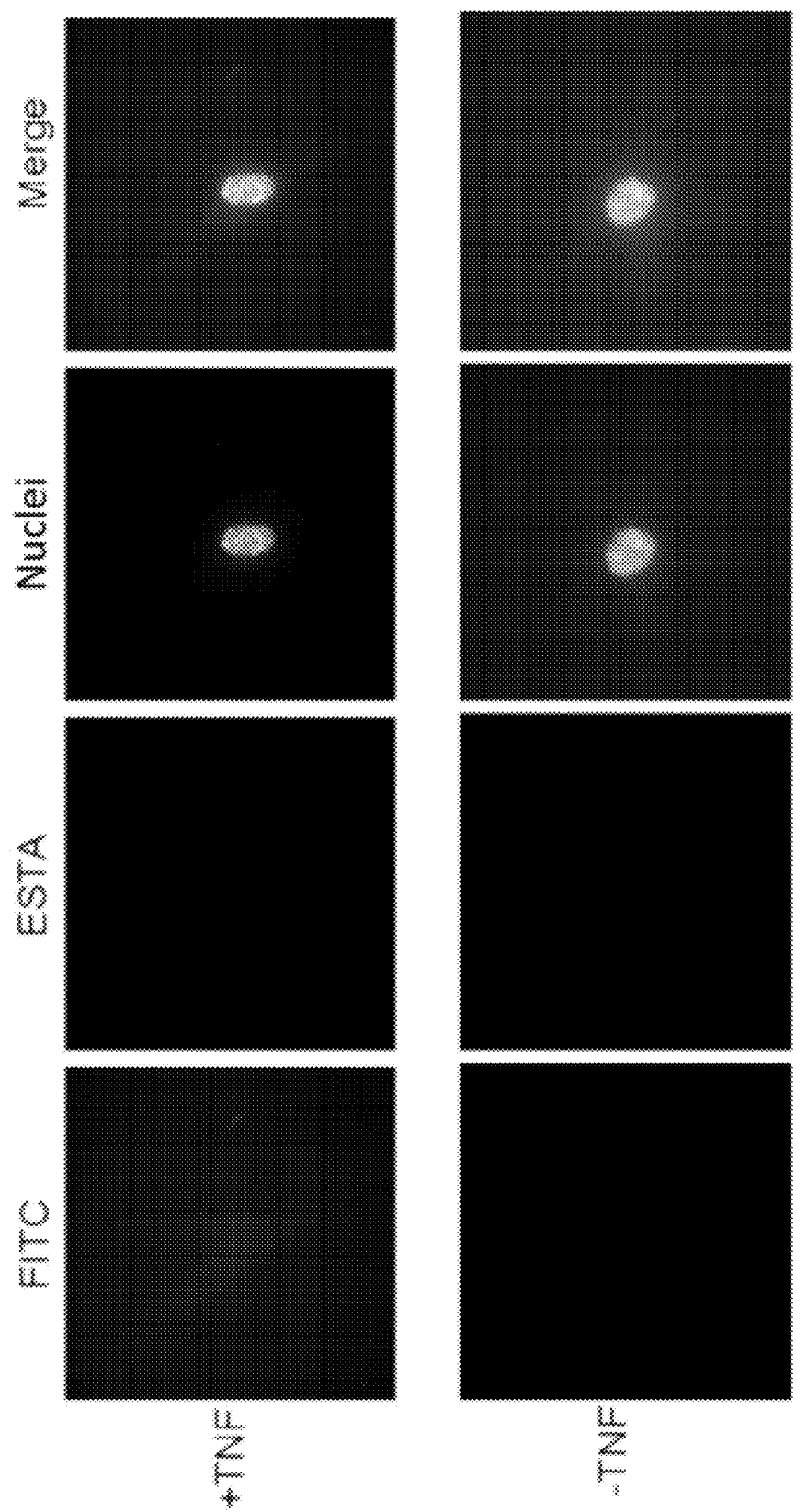
FIG. 16 illustrates that non-ESTA-1 conjugated liposomes show only minimal interaction with endothelial cells induced using TNF-α to express E-selectin.

Following 4 hours of incubation with Cy3-ESTA-lip-FITC, the cells were briefly fixed with 4% paraformaldehyde and fluorescent intensities of both red and green fluorescence were measured by fluorescent microscope 100 nM of Cy3-ESTA conjugated liposomes encapsulating FITC (Cy3-ESTA-lip-FITC) were incubated with HUVEC that were treated or untreated with TNF-α for 2 hours at 37° C. As a negative control, $NH_2$-PEG liposomes encapsulating FITC ($NH_2$—PEG-lip) were used. Following 3 hours incubation, the cells were briefly washed with tissue culture media to remove the unbound liposomes and then incubated overnight. The cells were fixed with 4% paraformaldehyde, and the nuclei were counterstained with 1.0 µg/ml Hoechst 33342. The fluorescent signals were detected using TE2000-E, Nikon fluorescent microscope (×600 magnification) to determine the binding to the cells. All images were acquired under the same exposure conditions for the comparison of liposome binding to the cells (FIG. 16).

Alternatively, HUVEC were stimulated with TNF-α (1000 ng/ml) for 2-4 hours to induce E-selectin expression on the endothelial cell surface, the cells were dissociated with 5 mM EDTA and then incubated with FITC labeled E-selectin antibody (Pharmingen). As a negative control, the same amount of normal IgG was used and read using a FACS Caliber. The experiments were repeated at least three times and data represent an average value. TNF-α treatment increased the expression of E-selectin more than 20-fold when compared to untreated cells. The TNF-α treated cells were used to test the ability of the Cy3-ESTA-lip-FITC (Cy3-ESTA-1 conjugated liposome containing FITC) to bind to E-selectin on the HUVEC cell surface.

Figure 17:
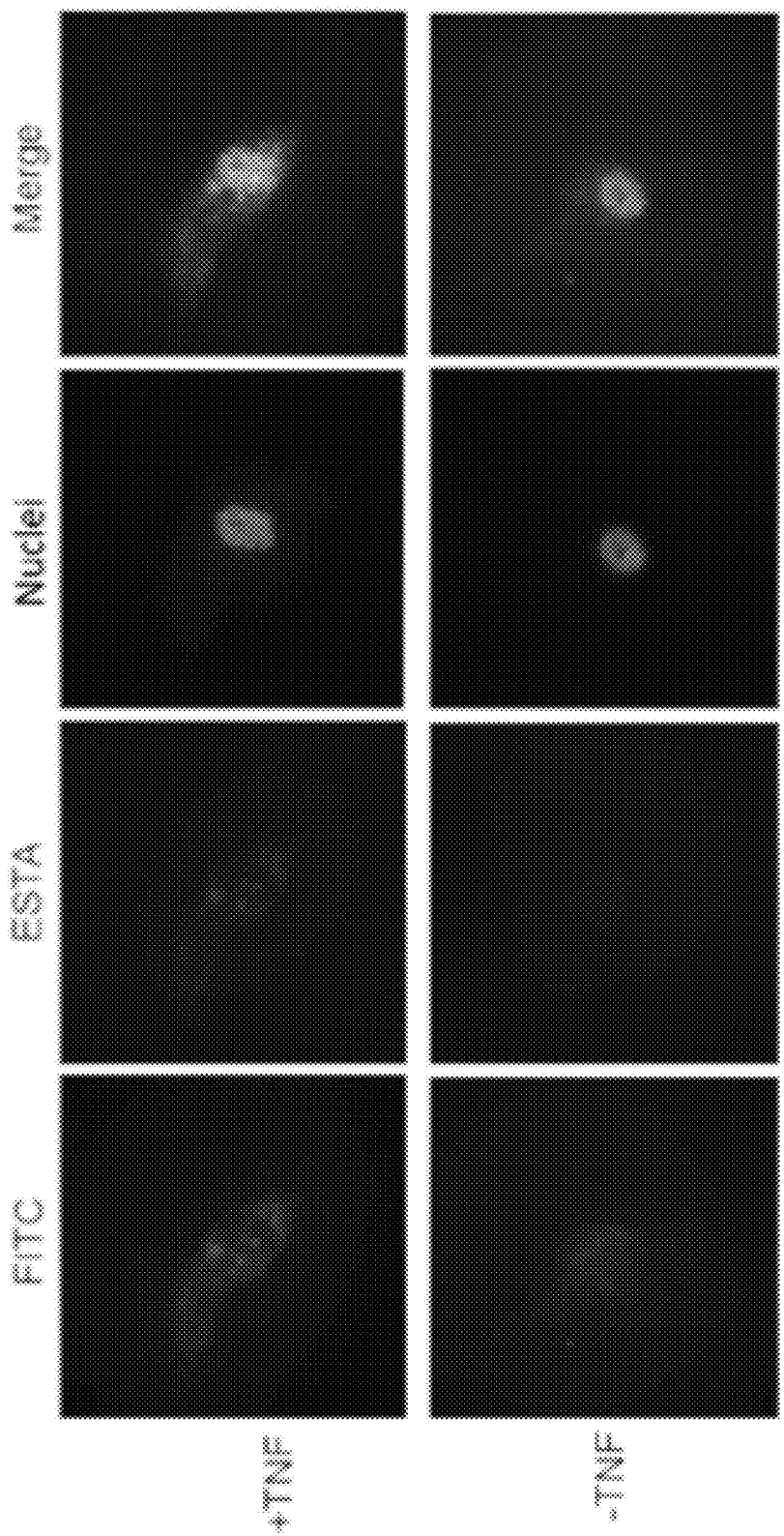
FIG. 17 illustrates that ESTA-1 targeted liposomes (Cy3-ESTA-1-lip-FITC) exhibit significantly higher levels of accumulation of both green (liposome) and red (Cy3-conjugated ESTA-1 to the liposome) fluorescence around endothelial cells induced to express E-selectin by treatment with TNF-α.
Figure 18:
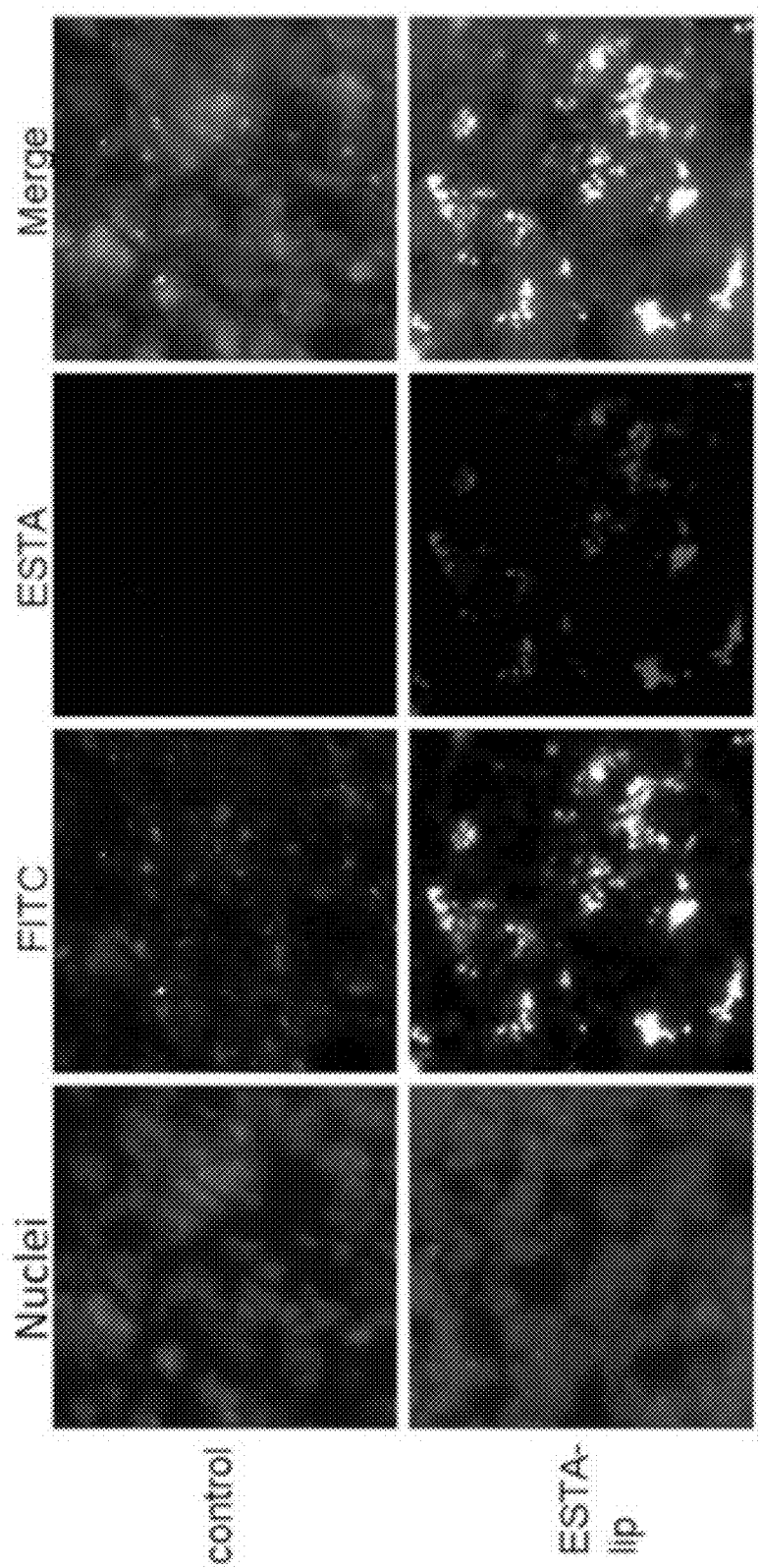
FIG. 18 illustrates in vivo that ESTA-1 targeted liposomes (Cy3-ESTA-1-lip-FITC) accumulate in the tumor vasculature of breast carcinoma following intravenous administration, in a mouse model.

The cells treated with Cy3-ESTA-lip-FITC at a concentration of 100 µM showed intense FITC and Cy3 fluorescence in the cells stimulated with TNF-α when compared with unstimulated controls (FIG. 17). Regardless of the treatment of TNF-α, control unconjugated liposomes showed only minimal interaction with the cells (whereas Cy3-ESTA-lip-FITC exhibited significantly higher levels of accumulation of both green (liposome) and red (Cy3-conjugated ESTA to the liposome) fluorescence around the cells when treated with TNF-α (FIG. 17). Intense accumulation of fluorescence was observed in vesicles, indicating that the Cy3-ESTA-lip-FITC were internalized into the cells via E-selectin. The merged fluorescence of FITC and Cy3 suggest that the Cy3-ESTA-lip-FITC were internalized after binding to E-selectin on the cell surface. This co-migration of both thioaptamer and liposome was observed within 24 hours (data not shown). Regardless of TNF stimuli, un-conjugated liposomes as negative control only showed minor interaction to the cells and the fluorescent signal was almost undetectable after normalization (FIG. 18).

Example 11

Selectivity of ESTA-1 Binding

Figure 19:
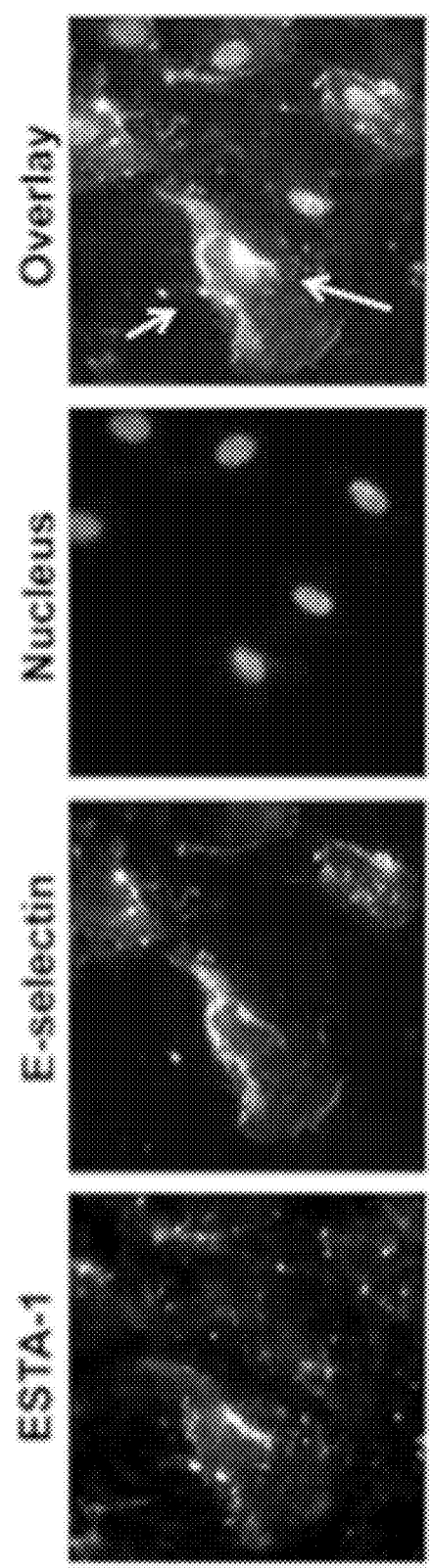
FIG. 19 illustrates the specificity of ESTA-1 by using colocalization of E-selectin monoclonal antibodies and ESTA-1 binding to E-selectin expressing ES-Endo cells. ES-Endo cells were treated with doxycycline (2000 ng/ml) to induce the expression of E-selectin. Using immunofluorescence, E-selectin expressing ES-Endo cells were stained with labeled ESTA-1 binding and labeled monoclonal anti-E-selectin.

To demonstrate the selectivity of ESTA-1 binding to E-selectin, immunostaining was performed using a labeled monoclonal antibody (clone 68-5H11, Cat No. 555648, BD Pharmingen™, BD Biosciences, San Jose, Calif., USA) that binds E-selectin but does not compete with ESTA-1 binding and with labeled ESTA-1. ES-Endo cells were induced to express E-selectin using doxycycline (2000 ng/ml). As seen in FIG. 19. ESTA-1 (red fluorescence) partially co-localized with the E-selectin bound by the anti-E selectin monoclonal antibody (green fluorescence) on the edge of the cells, as is indicated by the arrows in the overlay. Thus indicating that ESTA-1 binds to E-selectin on the cell surface.

Several reports suggest that E-selectin internalizes and undergoes a recycling following membrane sorting. In addition, our 3-D confocal imaging analysis of E-selectin expressing endothelial cells demonstrated intracellular localization of ESTA-1, suggesting internalization of ESTA-1 (unpublished). Although binding kinetics were not measured, 50% of the coverage of the liposomes containing 1.1% amine-PEG with ESTA-1 was sufficient to produce high-retention kinetics. In these studies, the liposomes were formulated to contain 1.1% of amino-PEG, although the ratio can be modified up to 5% to further enhance the amounts of ESTA-1 bioconjugation to increase binding specificity and affinity if desired.

Example 12

In Vivo Carcinoma Mouse Model

The tumor vasculature specific targeting of the ESTA-1 conjugated liposome described above was applied to mouse model of breast carcinoma. 5-week old female athymic nu/nu nude mice (Charles River) were maintained in a VAF-barrier facility and all animal procedures were performed in accordance with the regulations in the Institutional Animal Care and Use Committee at the University of Texas Health Science Center at Houston. An orthotopic breast tumor was established as previously reported with minor modification. When tumors became palpable (approx. 200-300 mm3), either encapsulated ESTA-lip-rhodamine or NH2-PEG-lip (3 mg of total lipid in 100 µl of saline) was intravenously injected into mice via tail vein (n=3 per group). One day after the injection, the tumors were harvested and immediately mounted in OCT media for subsequent histological analysis. To examine tumor localization of liposomes, the frozen tissues were sectioned (8 µm thickness) and analyzed by fluorescent microscope. The frozen sections were also immunostained as described.

Pharmacokinetics of liposomes: Following a single intravenous bolus administration of the ESTALip-Rhodamine or $NH_2$-PEG-Lip (3 mg of total lipid in 100 µl of saline) into 10 weeks old FBV mice (n=3-4), whole blood was collected at different time points by cardiac puncture. The fluorescence intensity in the plasma (50 µl) was measured using a fluorimeter at 544/594 nm (excitation/emission wavelengths) to determine the pharmacokinetics parameters of each liposome. Plasma samples were also collected from untreated mice as a baseline.

ESTA-1 conjugated FITC/Cy3 liposomes (50 nM in 100 ul saline) were injected intravenously into a mouse with a breast tumor. No notable binding of control liposomes to the tumor vasculature was observed. In contrast, the application of ESTA-1 conjugated FITC/Cy3 liposomes resulted in accumulation of ESTA-liposomes in the tumor (FIG. 19). There was also no accumulation of the ESTA-liposome in the other organs. Again, merged images show that the ESTA-Cy3 co-localized with the FITC-liposome showing that the thio-aptamer targeting agent remained intact in both cell and animal models. This provides in vivo evidence of the ability of aptamers that bind E-selectin to target liposome directly to tumor vasculature.

Furthermore, 48 h after the injection, ESTA-lip accumulation in the tumor parenchyma was increased markedly, suggesting that enhanced tumor vasculature targeting may facilitate subsequent extravasation of the liposomes into tumor parenchyma. Interestingly, the appearance of speckled patterns obtained from these experiments was similar to that of ESTA-1 alone. This speckled pattern might be due to either intracellular vesicle localization or simply a reflection of clustered and discontinuous E-selectin expression pattern on the cell surface.

Example 13

Aptamer Coupling to Microparticles

Amine modified particles are used for covalent coupling of Cy3 labeled carboxyl-ESTA (3' terminus) by activating the carboxyl groups with water-soluble carbodiimide. The carbodiimide reacts with the carboxyl group to create an active ester that reacts with the primary amines on the particles. This active ester intermediate can be stabilized by the addition of sulfo-NHS. Incubation for 4 hrs at room temperature resulted in conjugation.

To carry out coupling of labeled or unlabeled ESTA a PolyLink Protein Coupling Kit (Bangs Laboratories, Inc., Fishers, Ind., USA) is used. The microparticles, PolyLink Coupling Buffer (50 mM MES, pH 5.2; 0.05% Proclin® 300) and PolyLink Wash/Storage Buffer (10 mM Tris, pH 8.0; 0.05% Bovine Serum Albumin; 0.05% Proclin 300) are warmed to room temperature. 12.5 mg of microparticles is placed in a microcentrifuge tube the microparticles are pelleted via centrifugation for 5-10 minutes at approximately 500-1000×G. The microparticle pellet is resuspended in PolyLink Coupling Buffer and mixed gently end-over-end. The microparticles are again pelleted via centrifugation for 5-10 minutes at approximately 500-1000×G. The microparticle pellet is resuspended in 0.17 mL PolyLink Coupling Buffer and mixed gently end-over-end. Immediately prior to use a 200 mg/mL PolyLink EDAC (Carbodiimide) solution by dissolving 10 mg PolyLink EDAC in 50 μL PolyLink Coupling Buffer is prepared and 20 μL of this EDAC solution was added to the microparticle suspension and mixed end-over-end. Protein equivalent to 200-500 μg was added and the tube mixed gently end-over-end and incubated for 30-60 minutes at room temperature with gentle mixing.

The mixture is centrifuged for 10 minutes at approximately 500-1000×G. The supernatant is saved to determine the amount of protein bound and the microparticle pellet is resuspended in 0.4 mL PolyLink Wash/Storage Buffer. Centrifugation is repeated and the supernatants are combined to determine bound protein. The particles are stored at 2-8° C. in PolyLink Wash/Storage Buffer. Protein concentrations of the starting solution and supernatants after binding are determined by measuring the absorbance at 280 nm or by utilizing commercial protein assay kits. To determine the amount of protein bound to the microparticles, the amount of protein left in the supernatants is subtracted from the amount of protein added. This process may also be used to couple with carboxy-modified superparamagnetic particles, carboxylated silica or polymer/magnetic (e.g. ProMag™) microspheres.

Example 14

Aptamer Coupling to Multistage Nanoparticles

E-selectin is an attractive biological target for the delivery of drug carriers to, among other tissue, the bone marrow (BM) endothelium. A previously developed a multistage vector (MSV) comprising of biodegradable and biocompatible porous silicon microparticles loaded with therapeutic nanoparticles and released at desired rates (as described in, for example, Nanochanneled Device and Related Methods, U.S. Patent App. Pub. No. 20100152699 and PCT Patent App. Pub. No. WO2010120817), Multistage Delivery of Active Agents (U.S. Patent App. Pub. No. 20080311182A1 and PCT Patent App. Pub. No. WO2008/021908); Porous Particles and Methods of Making Thereof (U.S. Patent App. Pub. No. 20080280140 and PCT Patent App. Pub. No. WO2008/134637); Nanoporous Substrates for Analytical Methods (U.S. Patent App. Pub. No. 20080277578 and PCT Patent App. Pub. No. WO2007/120248); as well as in Tasciotti, et al., Nat Nanotechnol 2008, 3: 151; Tanaka, et al., Cancer Res 2010, 70: 3687). The functionalization of the porous silicon surface can facilitate site-specific delivery of the payload using a MSV that targets BM via biological recognition of E-selectin on the endothelium for the delivery of therapeutic nanoparticles to the BM tissue.

Porous MSV of quasi-hemispherical shape were fabricated using standard electrochemical etching and photolithography technique. SEM images verified that the average diameter of MSV was 1.6±0.1 μm with average pore size diameter of 30 nm and 60% porosity. The MSVs were oxidized and functionalized by 3'-aminopropyltriethoxysilane for conjugation with ESTA-1. ESTA-1 was synthesized containing a carboxyl group and a Cy3 dye on the 5' terminus. Carboxy-Cy3-ESTA-1 was conjugated to amine modified MSV.

Oxidized multistage particles (MSV) were incubated with APTES (3-aminopropyltriethoxysilane) to modify the surface with amine groups. Amine modified multistage particles were used for covalent coupling of Cy3 labeled carboxyl-ESTA-1 (3' terminus) by activating the carboxyl groups with water-soluble carbodiimide. The carbodiimide reacts with the carboxyl group to create an active ester that reacts with the primary amines on the particles. This active ester intermediate can be stabilized by the addition of sulfo-NHS.

In addition, conjugation of ESTA-1 on MSV was confirmed by the reduction of Zeta potential indicating that the surface charge of MSV changed from +6 mV of amine modified MSV to −35 mV of ESTA-1-MSV due to the presence of negatively charged DNA on the surface of MSV. In addition the fluorescence intensity of MSV increased approximately 100 times (from 101 to 10561 AU) after Cy3-ESTA conjugation as demonstrated using flow cytometry.

Furthermore the analysis of ESTA-1-MSV by Fourier transform infrared spectroscopy (FTIR) differed significantly from spectra of ESTA-1 and MSV alone and exhibited the appearance of a characteristic peak corresponding to P=O bending (1060 cm$^{-1}$) from the DNA and a shift in the C=O stretch form carboxyl (1650 cm$^{-1}$) attributable to the ester formation on conjugation and indicative of a successful conjugation of ESTA-1 to MSV.

The stability of ESTA-1-MSV to serum nucleases was established by incubating the conjugate in freshly isolated mouse serum at 37° C. and measuring the Cy3 fluorescence of ESTA-1-MSV at different time points. No change in the fluorescence intensity was observed for up to a 5-hour incubation. Analysis of these samples by gel electrophoresis and size distribution respectively and both of the materials (i.e., ESTA-1 and MSV) remained stable after serum incubation, indicating that ESTA-1-MSV was stable for up to 5 hours under physiologic conditions.

The ability to incorporate various forms of payload into the porous structure of ESTA-1-MSV, was demonstrated using overlay of green and red fluorescence, suggesting the loading of liposomes (green) into Cy3 ESTA-MSV (red) and confocal microscopy and flow cytometry and the loading of therapeutic paclitaxel encapsulating liposomes (size range 25-35 nm) and amino (PEG) coated Quantum dots (mean diameter 20 nm). The incorporation of amine functionalized superparamagnetic iron oxide nanoparticles (diameter 15 nm) into ESTA-1-MSV was confirmed by Prussian blue staining. These data demonstrate that ESTA-1-MSV can act to target therapeutics (e.g., liposomes) and imaging agents (e.g., Qdot or FeO NPs) to tissue bearing E-selection.

E-selectin inducible human microvascular endothelial cell line (ES-Endo), were induced by treatment with doxycycline to express E-selectin and used to demonstrate the E-selectin selective binding of ESTA-1-MSV. Greater than two fold higher levels of ESTA-1-MSV adhered to the endothelial cell surface than unconjugated MSV (P<0.05). But only if the cells had been induced to express E-selectin with doxycycline, indicating a need for E-selectin expression for enhanced binding of ESTA-1 targeted MSV to occur.

The presence of E-selectin on part of the vessels in BM was confirmed by immunohistochemical staining. The bio-distribution of ESTA-1-MSV was established by intravenously injecting mice with ESTA-1-MSV and harvesting major organs after 5 hours for analysis of silicon content using inductively coupled plasma. The accumulation of ESTA-1-MSV in the BM was 8 times higher than that observed with unconjugated MSV (P<0.05). The accumulation of ESTA-MSV in the bone marrow corresponded to 20% of injected dose/g organ weight. Non-targeted MSV exhibited minimum accumulation in the BM and accumulated primary accumulation in the liver and spleen. Similar findings obtained using histological techniques of analysis confirm that ESTA-1 conjugation to the MSV targeted BM accumulation and also reduced the trapping of MSV in the major RES organs such as liver and spleen.

Example 15

Delivery of Diagnostic and Therapeutic Nanoparticles to Ovarian Tumors

In addition to the evidence that liposomal nanoparticles can be targeted using aptamers that bind E-selectin, other nanoparticle-based delivery systems can be used for the in vivo delivery of imaging agents or therapeutic agents. For example, to establish proof of principle, that nanoparticles coupled to imaging or therapeutic agents and targeted using aptamers that bind E-selectin to direct to deliver the agents to tumors, nude mice bearing human HeyA8 orthotopic ovarian tumors are injected intravenously with ESTA-1-targeted nanoparticles associated with, or coupled to one or more imaging or therapeutic agents. After a predetermined period of time, these aptamer targeted nanoparticles can be imaged, thus identifying the size and location of tumor cells and delivering nanoparticle coupled therapeutic agents to the site of the tumor. This shows that aptamers that bind E-selectin may also be used as diagnostic agents to identify the size and location of tumor cells.

Example 16

Aptamer Therapeutics

In view of the foregoing in vivo evidence that indicate that aptamers that selectively bind E-selectin, such as ESTA-1, can selectively bind and target E-selectin the usefulness of such aptamers to block, image or target E-selectin is apparent. Such applications will result in, inter alia, modulation of E-selectin associated disorders, such as, but not limited to inflammatory responses or cancers and metastasis. While the in vivo data presented in the examples was obtained using mice, it should be understood that these observations will extend to other mammals including humans when the appropriate aptamers, such as ESTA-1, are utilized for targeting of imaging agents as described in the above examples as well as the targeting of therapeutics. The use of other aptamers for drug delivery has been described (see for example, the review by Etgar Levy-Nissenbaum et al., Nanotechnology and aptamers: applications in drug delivery. *Trends in Biotechnology.* 26(8): 442-449: 2008).

When in vivo administration of aptamers that selectively bind E-selectin, such as ESTA-1 is employed, normal dosage amounts may vary from about 10 ng to up to 300 mg, preferably about 1 µg, 2 µg, 3 µg, 4 µg, 5 µg, 8 µg, 10 µg, 20 µg, 40 µg, 60 µg, 80 µg, 100 µg, 200 µg, 400 µg, 600 µg, 800 µg, 1 mg, 2, mg, 3 mg, 4 mg, 5 mg, 6 mg, 7 mg, 8 mg, 9 mg, 10 mg, 12 mg, 14 mg, 16 mg, 18 mg, 20 mg, 22 mg, 24 mg, 25 mg, 26 mg, 28 mg, 30 mg, 40 mg, 45 mg, 50 mg, 55 mg, 60 mg, 65 mg, 70 mg, 75 mg, 80 mg, 85 mg, 90 mg, 100 mg, 110 mg, 120 mg, 140 mg, 160 mg, 180 mg, 200 mg, 220 mg, 240 mg, 260 mg, 280 mg or 300 mg is delivered in a single, or multiple, bolus administrations or alternatively delivered as an infusion at a dose per kg of mammal body weight per day depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compositions and different E-selectin associated disorders or symptoms, that administration targeting one organ or tissue, for example, may necessitate delivery in a manner different from that to another organ or tissue.

When treatment of humans suffering from an E-selectin associated disorder such as, for example, an inflammatory disorder or cancers, is desired a purified preparation comprising aptamers that selectively bind E-selectin, such as ESTA-1, are applied by intravenous infusion over time in the presence of a physiologically acceptable solvent (saline, dextrose solution, etc.) or by bolus injection (subcutaneous, intramuscular, or intraperitoneal) or by placement into the eye or by intravitreal injection. Alternatively, aptamers that selectively bind E-selectin, such as ESTA-1 that target E-selectin and inhibit E-selectin activity can be administered by any of the routes (oral, aerosol, etc.) known to those of skill in the art that effectively deliver the drug to the patient in need of treatment.

Aptamers that selectively bind E-selectin, such as ESTA-1, may be administered daily, every other day, weekly, bi-weekly, monthly, bi-monthly, quarterly or once per year, by any suitable route of administration, including oral, subcutaneous and parenteral administration. Examples of parenteral administration include intravenous, intraarticular, intramuscular, intranasal, intraocular, inhaled and intraperitoneal.

Regardless of the manner of administration, the specific dose may be calculated according to such factors as body weight or body surface and based on finding in drug metabolism and pharmacokinetic (DMPK) analyses. Further refinement of the calculations necessary to determine the appropriate dosage for modulating E-selectin associated disorders and symptoms, inter alia, inflammatory disorders or cancers, can readily be made by those of ordinary skill in the art without undue experimentation.

During the course of treatment, the effects of the E-selectin aptamers on inter alia, inflammatory disorders or cancers can be monitored and evaluated using, for example, CBC and differentials to enumerated blood cells, sedimentation rates, cytokine levels and cell subpopulation analyses done on, peripheral blood or other sample, as appropriate based on symptoms, intuition or the results of other medical laboratory techniques available through most medical facilities and hospitals, such as CBC, FACS and clinical blood chemistry analysis as well as using known imaging and diagnostic technologies.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

We claim:

1. An isolated nucleic acid molecule that selectively binds to an E-selectin protein and comprises a contiguous 29-30 nucleotide sequence that includes at least one monothiophosphate or a dithiophosphate modified nucleotide and which contains at least one motif selected from the group consisting of ACTYCWCYTCAC (SEQ ID NO.: 18), TCCTC (SEQ ID NO.: 50), TCCGTT (SEQ ID NO.: 51), TCCCCK (SEQ ID.: 52), ACCCWM (SEQ ID NO.: 53), ACTHC (SEQ ID NO.: 54), TCCCK (SEQ ID NO.: 55), ATCC (SEQ ID NO.: 56), CCGTY (SEQ ID NO.: 57) and CTTCW (SEQ ID NO.: 58), wherein Y=T or C, W=A or T, K=T or G, and M=A, or C, or has the nucleotide sequence of SEQ ID NO.: 31.

2. The isolated nucleic acid molecule of claim 1, wherein the contiguous 29-30 nucleotide sequence is selected from the group consisting of SEQ ID NO.: 37-49 wherein at least one nucleotide is a monothiophosphate or a dithiophosphate modified nucleotide.

3. The isolated nucleic acid molecule of claim 1, wherein the contiguous 29-30 nucleotide sequence contains at least one deoxyadenosine monothiophosphate.

4. The isolated nucleic acid molecule of claim 1 having a secondary structure with a free energy of folding in the range of about −8.0 to about −10.7 kcal/mol.

5. The isolated nucleic acid molecule of claim 1, wherein said molecule binds to E-selectin with binding affinity ($K_D$) in the nanomolar to picomolar range.

6. The isolated nucleic acid molecule of claim 1 wherein said contiguous 29-30 nucleotide sequence has the nucleotide sequence of SEQ ID NO.: 37, SEQ ID NO.: 44 or SEQ ID NO.: 48.

7. The isolated nucleic acid molecule of claim 1, wherein said contiguous 29-30 nucleotide sequence is disposed between SEQ ID NO.: 59 at the 5' end and SEQ ID NO.: 60 at the 3' end.

8. The isolated nucleic acid molecule of claim 1, having the sequence of SEQ ID NO.: 1.

9. The isolated nucleic acid molecule of claim 1, comprising double-stranded stem structures at the 5' and 3' ends.

10. A composition comprising the isolated nucleic acid molecule of claim 1 and a pharmaceutically acceptable salt.

11. The composition of claim 10, wherein said isolated nucleic acid molecule is coupled to a therapeutic agent or an imaging agent, or both.

12. The composition of claim 11, comprising a conjugate containing a particle coupled to said nucleic acid molecule.

13. A method of inhibiting an E-selectin mediated interaction with a natural E-selectin ligand, comprising:
    selectively binding the isolated nucleic acid molecule of claim 1 to an E-selectin protein on a target tissue; and
    exposing said target tissue to said natural E-selectin ligand.

14. The method of claim 13, wherein said target tissue comprises a vessel wall and said exposing said target tissue to the natural E-selectin ligand comprises exposing the vessel wall to leukocytes, to block E-selectin-mediated leukocyte rolling and/or adhesion.

15. A method of delivering an imaging agent to a target tissue bearing E-selectin, comprising selectively binding to an E-selectin protein on said target tissue the composition of claim 11, wherein said isolated nucleic acid molecule is coupled to said imaging agent.

16. A method of delivering a therapeutic agent to an individual suffering from an E-selectin associated disorder, comprising:
    administering to said individual the composition of claim 10 comprising a therapeutic agent coupled to said isolated nucleic acid molecule.

17. The method of claim 16, wherein said isolated nucleic acid molecule coupled to said therapeutic agent targets a tissue expressing E-selectin in the individual, and enhances therapeutic activity of the therapeutic agent and/or reduces an adverse reaction associated with toxicity of the therapeutic agent.

18. The method of claim 17, wherein said E-selectin associated disorder comprises inflamed vasculature in the individual, and wherein said administering comprises:
- administering intravenously to an individual in need thereof, said composition, wherein said composition comprises said nucleic acid molecule coupled to a particle containing said therapeutic agent;
- causing said particle-coupled nucleic acid molecule to selectively bind to E-selectin on said inflamed vasculature; and
- causing said therapeutic agent to be released from the E-selectin-bound nucleic acid molecule-coupled particle to treat said inflamed vasculature.

19. A method of imaging inflamed vasculature, comprising:
- administering intravenously to an individual in need of such imaging the composition of claim 12, wherein said conjugate includes said imaging agent;
- causing said conjugate to selectively bind to E-selectin on said inflamed vasculature; and
- visualizing the imaging agent bound to said E-selectin on the inflamed vasculature, to identify a location of inflamed vasculature in said individual.

20. The method of claim 19 wherein said inflamed vasculature comprises tumor vasculature in the individual.

* * * * *

UNITED STATES PATENT AND TRADEMARK OFFICE
CERTIFICATE OF CORRECTION

PATENT NO. : 8,658,614 B2  
APPLICATION NO. : 13/209866  
DATED : February 25, 2014  
INVENTOR(S) : David G. Gorenstein et al.

Page 1 of 1

It is certified that error appears in the above-identified patent and that said Letters Patent is hereby corrected as shown below:

On the Title page, item (73) Assignee, change "The University of Texas Heal Science Center, Houston, TX (US)" to --The Board of Regents of the University of Texas System, Austin, TX (US).--

Signed and Sealed this  
Thirteenth Day of May, 2014

Michelle K. Lee  
*Deputy Director of the United States Patent and Trademark Office*